United States Patent
Remenar et al.

(10) Patent No.: US 7,186,863 B2
(45) Date of Patent: Mar. 6, 2007

(54) SERTRALINE COMPOSITIONS

(75) Inventors: Julius Remenar, Framingham, MA (US); Michael MacPhee, Pawtucket, RI (US); Matthew Lynn Peterson, Hopkinton, MA (US); Mark Tawa, Brighton, MA (US)

(73) Assignee: TransForm Pharmaceuticals, Inc., Lexington, MA (US)

( * ) Notice: Subject to any disclaimer, the term of this patent is extended or adjusted under 35 U.S.C. 154(b) by 406 days.

(21) Appl. No.: 10/851,382

(22) Filed: May 21, 2004

(65) Prior Publication Data

US 2005/0014829 A1    Jan. 20, 2005

Related U.S. Application Data

(60) Provisional application No. 60/492,868, filed on Aug. 6, 2003, provisional application No. 60/492,141, filed on Aug. 1, 2003, provisional application No. 60/472,939, filed on May 23, 2003.

(51) Int. Cl.
*A61K 31/135* (2006.01)
*C07C 211/00* (2006.01)

(52) U.S. Cl. ............... 564/308; 564/428; 514/657
(58) Field of Classification Search .......... 564/453, 564/457, 462, 308, 427; 514/657
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,536,518 A | 8/1985 | Welch et al. | |
| 5,059,595 A | 10/1991 | LeGrazie | |
| 5,073,543 A | 12/1991 | Marshall et al. | |
| 5,120,548 A | 6/1992 | McClelland et al. | |
| 5,248,699 A | 9/1993 | Sysko et al. | |
| 5,354,556 A | 10/1994 | Sparks et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,733,566 A | 3/1998 | Lewis | |
| 5,734,083 A | 3/1998 | Wilson et al. | |
| 6,132,420 A | 10/2000 | Dionne et al. | |
| 6,245,357 B1 | 6/2001 | Edgren et al. | |
| 6,262,308 B1 | 7/2001 | Bigot | |
| 6,270,787 B1 | 8/2001 | Ayer | |
| 6,283,953 B1 | 9/2001 | Ayer et al. | |
| 6,287,295 B1 | 9/2001 | Chen et al. | |
| 6,333,050 B2 | 12/2001 | Wong et al. | |
| 6,342,249 B1 | 1/2002 | Wong et al. | |
| 6,365,185 B1 | 4/2002 | Ritschel et al. | |
| 6,368,626 B1 | 4/2002 | Bhatt et al. | |
| 6,375,978 B1 | 4/2002 | Kleiner et al. | |
| 6,452,054 B2 | 9/2002 | Aronhime et al. | |
| 6,495,721 B1 | 12/2002 | Schwartz et al. | |
| 6,500,987 B1 * | 12/2002 | Schwartz et al. | 564/308 |
| 6,517,866 B1 | 2/2003 | Am Ende et al. | |
| 2002/0048610 A1 | 4/2002 | Cima et al. | |
| 2002/0183555 A1 | 12/2002 | Schwartz et al. | |
| 2003/0023117 A1 | 1/2003 | Aronhime et al. | |

FOREIGN PATENT DOCUMENTS

| | | |
|---|---|---|
| WO | WO 00/21521 | 4/2000 |
| WO | WO 00/32551 | 6/2000 |
| WO | WO 01/32601 | 5/2001 |
| WO | WO 01/45692 | 6/2001 |
| WO | WO 01/90049 | 11/2001 |
| WO | WO 02/096859 | 12/2002 |

OTHER PUBLICATIONS

Almarsson et al., "High-Throughput Surveys of Crystal Form Diversity of Highly Polymorphic Pharmaceutical Compounds", Crystal Growth and Design, 3 (6), pp. 927-933 (2003).
Kim, Cherng-Ju, Controlled Release Dosage Form Design, Technomic Publishing Co., Lancaster, PA, pp. 231-238 (2000).

* cited by examiner

*Primary Examiner*—Samuel Barts
(74) *Attorney, Agent, or Firm*—Paul Burgess

(57) ABSTRACT

An acid salt of sertraline, wherein the acid is citric acid, fumaric acid, malic acid, maleic acid, malonic acid, phosphoric acid, succinic acid, sulfuric acid, L-tartaric acid, HBr, acetic acid, benzoic acid, benzenesulfonic acid, ethanesulfonic acid, lactic acid, methanesulfonic acid or toluenesulfonic acid. Similarly, a solvate of sertraline HCl, wherein the solvent is methanol, ethanol, n-propanol, isopropanol, n-butanol, isobutanol, t-butanol, acetic acid, ethyl acetate, or propylene glycol.

7 Claims, 44 Drawing Sheets

SERTRALINE COMPOSITIONS

RELATED APPLICATIONS

This application claims the benefit of priority of U.S. Provisional Application No. 60/472,939 filed on May 23, 2003, U.S. Provisional Application No. 60/492,141 filed on Aug. 1, 2003 and U.S. Provisional Application No. 60/492,868 filed on Aug. 6, 2003.

FIELD OF THE INVENTION

The present invention relates to drug-containing compositions, pharmaceutical compositions comprising such drugs, and methods for preparing same.

BACKGROUND OF THE INVENTION

Drugs in pharmaceutical compositions can be prepared in a variety of different forms. Such drugs can be prepared so as to have a variety of different chemical forms including chemical derivatives or salts. Such drugs can also be prepared to have different physical forms. For example, the drugs may be amorphous or may have different crystalline polymorphs, perhaps existing in different salvation or hydration states. By varying the form of a drug, it is possible to vary the physical properties thereof. For example, crystalline polymorphs typically have different solubilities from one another, such that a more thermodynamically stable polymorph is less soluble than a less thermodynamically stable polymorph. Pharmaceutical polymorphs can also differ in properties such as shelf-life, bioavailability, morphology, vapor pressure, density, color, and compressibility.

Sertraline ((1S,4S)-4-(3,4-Dichlorophenyl)-1,2,3,4-tetrahydro-N-methyl-1-naphthalenamine) (CAS Registry Number: 79617-96-2) is represented by structure (I):

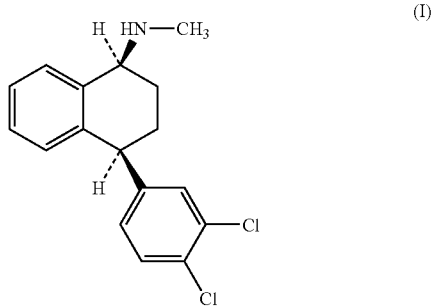

It would be advantageous to have new forms of sertraline that have improved properties, in particular, as oral formulations. Specifically, it is desirable to identify improved forms of the drug that exhibit significantly increased aqueous solubilities, stability, hygroscopicity and decreased form polymorphism. It is also desirable to increase the dissolution rate of drug-containing pharmaceutical compositions in water, increase the bioavailability of orally-administered compositions, and provide a more rapid onset to therapeutic effect. It is also desirable to have a form of the drug which, when administered to a subject, reaches a peak plasma level faster and/or has a longer lasting plasma concentration and higher overall exposure at high doses when compared to equivalent amounts of the drug in its presently-known form.

SUMMARY OF THE INVENTION

It has now been found that new salt forms of sertraline can be obtained which have different properties as compared to the converted forms of the drug.

Accordingly, in a first aspect, the present invention provides an acid salt of sertraline, wherein the acid is citric acid, fumaric acid, malic acid, maleic acid, malonic acid, phosphoric acid, succinic acid, sulfuric acid, L-tartaric acid, HBr, acetic acid, benzoic acid, benzenesulfonic acid, ethanesulfonic acid, lactic acid, methanesulfonic acid or toluenesulfonic acid.

The invention further provides a pharmaceutical composition comprising an acid salt of sertraline. Typically, the pharmaceutical composition further comprises one or more pharmaceutically-acceptable carriers, diluents or excipients. Pharmaceutical compositions according to the invention are described in further detail below.

In another aspect, an acid salt of sertraline is made by reacting sertraline with an organic or inorganic acid in a crystallization solvent, wherein the acid salt has an aqueous solubility of approximately 5 micrograms/mL to approximately 100 mg/mL.

In a further aspect, the present invention provides a process for the preparation of an acid salt of sertraline, which comprises:
 (a) combining sertraline with an acid to form a mixture;
 (b) subjecting the mixture to conditions which salify the sertraline whereby crystals of a sertraline salt are formed; and
 (c) optionally isolating the salt.

In one arrangement, the sertraline may be mixed with the acid in solution. Any suitable solvent may be used for this step, including organic solvents or mixed solvents. Solvents comprising alcohols are good examples with methanol a preferred alcohol. A water/methanol mixed solvent is also a possibility.

Any conditions which salify the sertraline from solution may be used whereby crystals of the sertraline salt are formed. Conveniently, this step includes evaporation of the solvent so as to concentrate the solute whereby sertraline salt crystals may be precipitated. In a preferred embodiment, the solution is first heated to ensure mixing and salt formation, followed by cooling so as to enable salt crystals to precipitate.

In an alternative embodiment, the sertraline is mixed with the acid in a solid phase. Any suitable means for mixing may be used in this step, including commercially-available solid mixers. The solid mixture thus formed is preferably heated so as to cause salification of the sertraline with the acid. In this step it is possible that salt crystals may form spontaneously upon heating. It is preferred in this embodiment to ensure that the solid mixture is comminuted, typically by grinding the mixture prior to heating so as to facilitate salification.

The salt, typically in the form of crystals, may be isolated by any conventional techniques.

In a further aspect, the present invention provides a process for modulating the solubility of sertraline for use in a pharmaceutical composition, which process comprises:
 (a) combining sertraline with an acid to form a mixture; and
 (b) salifying the sertraline with the acid so that the solubility of the sertraline is modulated, wherein the acid is citric acid, fumaric acid, malic acid, maleic acid, malonic acid, phosphoric acid, succinic acid, sulfuric acid, L-tartaric acid, HBr, acetic acid, benzoic acid, benzenesulfonic acid, ethanesulfonic acid, lactic acid, methanesulfonic acid or toluenesulfonic acid.

In a further aspect, the present invention provides a process for modulating the dose response of sertraline for use in a pharmaceutical composition, which process comprises:

(a) combining sertraline with an acid to form a mixture, and (b) salifying the sertraline with the acid so that the dose response of the sertraline is modulated, wherein the acid is citric acid, fumaric acid, malic acid, maleic acid, malonic acid, phosphoric acid, succinic acid, sulfuric acid, L-tartaric acid, HBr, acetic acid, benzoic acid, benzensulfonic acid, ethanesulfonic acid, lactic acid, methanesulfonic acid or toluenesulfonic acid.

In a further aspect, the present invention provides a solvate of sertraline. In one embodiment, the solvate is a polar organic solvent. In a further embodiment, the solvate is an alcohol. In a further embodiment, the solvate is methanol, ethanol, n-propanol, isopropanol, n-butanol, isobutanol, t-butanol, acetic acid, ethyl acetate, glycerol, or propylene glycol.

The invention further provides a pharmaceutical composition comprising a solvate of sertraline. In one embodiment, the pharmaceutical composition further comprises one or more pharmaceutically-acceptable carriers, diluents, or excipients. In another embodiment, a pharmaceutical composition comprising a sertraline HCl acetic acid solvate is provided. In another embodiment, a pharmaceutical composition comprising a sertraline HCl ethyl acetate hemisolvate is provided.

In a further aspect, the present invention provides a process for the preparation of a solvate of sertraline, which comprises:

(a) combining sertraline with a solvent to form a mixture;

(b) subjecting the mixture to conditions whereby crystals of a sertraline solvate are formed; and (c) optionally isolating the solvate.

In a further embodiment, the process for the preparation of a sertraline solvate comprises mixing sertraline with a polar organic solvent. In another embodiment, the preparation of a sertraline solvate comprises mixing sertraline with an alcohol. In another embodiment, the preparation of a sertraline solvate comprises mixing sertraline with methanol, ethanol, n-propanol, isopropanol, n-butanol, isobutanol, t-butanol, acetic acid, ethyl acetate, glycerol, or propylene glycol.

The processes according to the present invention may each comprise a further step or steps in which the sertraline salt produced thereby is incorporated into a pharmaceutical composition.

In a still further aspect of the invention, a method is provided for treating a subject, preferably a human subject, with a mood or psychological or other disorder where sertraline is an effective active pharmaceutical for said disorder. The method comprises administering to the subject a therapeutically-effective amount of an acid salt, acid salt solvate, free form solvate, or co-crystal solvate of sertraline. Such disorders include depression, PTSD, panic disorder, OCD, and premenstrual dysmorphic disorder, and other disorders susceptible to treatment with a selective serotonin reuptake inhibitor (SSRI).

DETAILED DESCRIPTION OF THE INVENTION

Figure 1A:
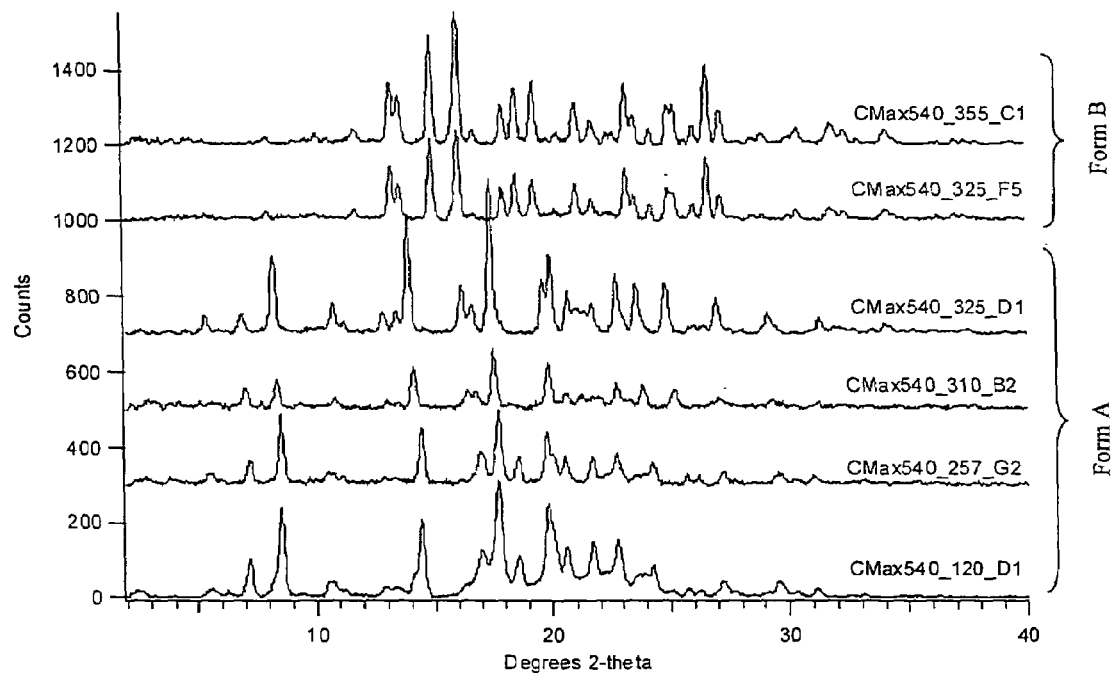
FIG. 1A—Compilation of PXRD data for sertraline benzoate salts

The present invention relates to sertraline salts, solvates, and methods of making and using the same. The sertraline salts of the present invention are made by combining an acid with sertraline. In one embodiment, the acid is an organic acid. In another non-limiting embodiment, the acid is selected from citric acid, fumaric acid, malic acid, maleic acid, malonic acid, phosphoric acid, succinic acid, sulfuric acid, L-tartaric acid, HBr, acetic acid, benzoic acid, benzensulfonic acid, ethanesulfonic acid, lactic acid, methanesulfonic acid or toluenesulfonic acid. The sertraline solvates of the present invention are made by combining a solvent with sertraline, a sertraline salt, or a sertraline co-crystal. In one embodiment, the solvent is an organic solvent. In another non-limiting embodiment, the solvent is methanol, ethanol, n-propanol, isopropanol, n-butanol, isobutanol, t-butanol, acetic acid, ethyl acetate, glycerol, or propylene glycol.

In one embodiment, an acid salt of sertraline is made by reacting sertraline with an organic or inorganic acid in a crystallization solvent, wherein the form has an aqueous solubility of approximately 5 micrograms/mL to approximately 100 mg/mL.

The preparation of a sertraline salt comprises combining sertraline and an acid. In one embodiment, the sertraline and the acid are heated. In another embodiment, the sertraline and the acid are heated, then cooled to room temperature for a time, and then cooled below room temperature. The resultant sertraline salt crystals can be collected via filtration or another technique known to one skilled in the art.

The amount of acid used to make sertraline salts is typically about 0.5–1 equivalents of acid for each equivalent of sertraline. These mole ratios are found when a sertraline salt is prepared according to methods described herein. Other mole ratios can also be used in various methods known in the art. The physical form of the acid salt is preferably compatible with its ability to be formed as a pharmaceutical composition readily. It is preferred that the acid salt is in a crystalline form and such crystalline forms are readily preparable according to the methods known in the art and described herein.

Several of the aforementioned salts have been observed to crystallize with more than one crystal structure. In fact, each of the sertraline benzoate, esylate, and mesylate salts have been found to form at least two polymorphs. Additionally, there is evidence to suggest the sertraline lactate salt is also polymorphic. The recognition of such polymorphs is of vital importance to the preparation of stable and consistent formulations comprising said sertraline salts. The existence of crystalline forms such as solvates and hydrates are equally important to investigate.

Sertraline solvates can be formed using various methods known in the art. Crystalline sertraline can be in the form of a free base, a salt, or a co-crystal. Free base sertraline can be crystallized in the presence of an appropriate solvent in order to form a sertraline solvate. In addition, sertraline acid salts (e.g. HCl, HBr, benzoic acid) can also be used in the preparation of solvates. For example, sertraline HCl forms a solvate with acetic acid and a hemi-solvate with ethyl acetate. Similarly, solvates of sertraline co-crystals can also be prepared.

The solvate molecules are incorporated into the crystal structure of solvates of sertraline, solvates of sertraline acid salts, and solvates of sertraline co-crystals via hydrogen bonding, van der Waals forces, or dispersion forces, or a combination of any two or all three forces. In another embodiment, the crystal structure of a monoclinic acetic acid solvate is attained predominantly by hydrogen bonds between the carboxylic acid group of acetic acid and the protonated secondary amine of sertraline HCl through the chloride ions.

The amount of solvent used to make sertraline solvates is typically about 1 equivalent of solvent for each equivalent of sertraline, however more or less solvent may be used. The mole ratios are found when a sertraline solvate is prepared according to methods described herein. Other mole ratios can also be used in various methods known in the art. The physical form of the solvate is preferably compatible with its ability to be formed as a pharmaceutical composition readily. It is preferred that the solvate is in crystalline form and such crystalline forms are readily preparable according to the methods known in the art and described herein.

In accordance with the present invention, these new crystalline forms of sertraline salts and solvates prepared by the new methods disclosed herein may be prepared as pharmaceutical compositions that are particularly useful for the treatment of depression, obsessive-compulsive disorder, and panic disorder. Such compositions comprise one of the new crystalline forms of sertraline salts or solvates with pharmaceutically acceptable carriers and/or excipients known to one of skill in the art.

For example, these compositions may be prepared as medicaments to be administered orally, parenterally, rectally, transdermally, bucally, or nasally. Suitable forms for oral administration include tablets, compressed or coated pills, dragees, sachets, hard or gelatin capsules, sub-lingual tablets, syrups and suspensions. Suitable forms of parenteral administration include an aqueous or non-aqueous solution or emulsion, while for rectal administration suitable forms for administration include suppositories with hydrophilic or hydrophobic vehicles. For topical administration the invention provides suitable transdermal delivery systems known in the art, and for nasal delivery there are provided suitable aerosol delivery systems known in the art.

Excipients employed in pharmaceutical compositions of the present invention can be solids, semi-solids, liquids or combinations thereof. Preferably, excipients are solids. Compositions of the invention containing excipients can be prepared by known technique of pharmacy that comprises admixing an excipient with a drug or therapeutic agent. A pharmaceutical composition of the invention contains a desired amount of drug per dose unit and, if intended for oral administration, can be in the form, for example, of a tablet, a caplet, a pill, a hard or soft capsule, a lozenge, a cachet, a dispensable powder, granules, a suspension, an elixir, a liquid, or any other form reasonably adapted for such administration. If intended for parenteral administration, it can be in the form, for example, of a suspension or transdermal patch. If intended for rectal administration, it can be in the form, for example, of a suppository. Presently preferred are oral dosage forms that are discrete dose units each containing a predetermined amount of the drug, such as tablets or capsules.

Non-limiting examples follow of excipients that can be used to prepare pharmaceutical compositions of the invention.

Pharmaceutical compositions of the invention optionally comprise one or more pharmaceutically acceptable carriers or diluents as excipients. Suitable carriers or diluents illustratively include, but are not limited to, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of alpha- and amorphous cellulose (e.g., RexcelJ), powdered cellulose, hydroxypropylcellulose (HPC) and hydroxypropylmethylcellulose (HPMC); calcium carbonate; glycine; bentonite; block co-polymers; polyvinylpyrrolidone; and the like. Such carriers or diluents, if present, constitute in total about 5% to about 99%, preferably about 10% to about 85%, and more preferably about 20% to about 80%, of the total weight of the composition. The carrier, carriers, diluent, or diluents selected preferably exhibit suitable flow properties and, where tablets are desired, compressibility.

Lactose, mannitol, dibasic sodium phosphate, and microcrystalline cellulose (particularly Avicel PH microcrystalline cellulose such as Avicel PH 101), either individually or in combination, are preferred diluents. These diluents are chemically compatible with drugs. The use of extragranular microcrystalline cellulose (that is, microcrystalline cellulose added to a granulated composition) can be used to improve hardness (for tablets) and/or disintegration time. Lactose, especially lactose monohydrate, is particularly preferred. Lactose typically provides compositions having suitable release rates of drugs, stability, pre-compression flowability, and/or drying properties at a relatively low diluent cost. It provides a high density substrate that aids densification during granulation (where wet granulation is employed) and therefore improves blend flow properties and tablet properties.

Pharmaceutical compositions of the invention optionally comprise one or more pharmaceutically acceptable disintegrants as excipients, particularly for tablet formulations. Suitable disintegrants include, but are not limited to, either individually or in combination, starches, including sodium starch glycolate (e.g., Explotab™ of PenWest) and pregelatinized corn starches (e.g., National™ 1551 of National Starch and Chemical Company, National™ 1550, and Colocorn™ 1500), clays (e.g., Veegum™ HV of R.T. Vanderbilt), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, locust bean, karaya, pectin and tragacanth gums.

Disintegrants may be added at any suitable step during the preparation of the composition, particularly prior to granulation or during a lubrication step prior to compression. Such disintegrants, if present, constitute in total about 0.2% to about 30%, preferably about 0.2% to about 10%, and more preferably about 0.2% to about 5%, of the total weight of the composition.

Croscarmellose sodium is a preferred disintegrant for tablet or capsule disintegration, and, if present, preferably constitutes about 0.2% to about 10%, more preferably about 0.2% to about 7%, and still more preferably about 0.2% to about 5%, of the total weight of the composition. Croscarmellose sodium confers superior intragranular disintegration capabilities to granulated pharmaceutical compositions of the present invention.

Pharmaceutical compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Such binding agents may also prevent or inhibit crystallization or recrystallization of a drug of the present invention once the salt has been dissolved in a solution. Suitable binding agents and adhesives include, but are not limited to, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™ of Aqualon); and ethylcellulose (e.g., Ethocel™ of the Dow Chemical Company). Such binding agents and/or adhesives, if present, constitute in total about 0.5% to about 25%, preferably about 0.75% to about 15%, and more preferably about 1% to about 10%, of the total weight of the pharmaceutical composition.

Many of the binding agents are polymers comprising amide, ester, ether, alcohol or ketone groups and, as such, are preferably included in pharmaceutical compositions of the present invention. Polyvinylpyrrolidones such as povidone K-30 are especially preferred. Polymeric binding agents can have varying molecular weight, degrees of crosslinking, and grades of polymer. Polymeric binding agents can also be copolymers, such as block co-polymers that contain mixtures of ethylene oxide and propylene oxide units. Variation in these units' ratios in a given polymer affects properties and performance. Examples of block co-polymers with varying compositions of block units are Poloxamer 188 and Poloxamer 237 (BASF Corporation).

Pharmaceutical compositions of the invention optionally comprise one or more pharmaceutically acceptable wetting agents as excipients. Such wetting agents are preferably selected to maintain the drug in close association with water, a condition that is believed to improve bioavailability of the composition.

Non-limiting examples of surfactants that can be used as wetting agents in pharmaceutical compositions of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefosse), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefosse), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, preferably about 0.4% to about 10%, and more preferably about 0.5% to about 5%, of the total weight of the pharmaceutical composition.

Wetting agents that are anionic surfactants are preferred. Sodium lauryl sulfate is a particularly preferred wetting agent. Sodium lauryl sulfate, if present, constitutes about 0.25% to about 7%, more preferably about 0.4% to about 4%, and still more preferably about 0.5% to about 2%, of the total weight of the pharmaceutical composition.

Pharmaceutical compositions of the invention optionally comprise one or more pharmaceutically acceptable lubricants (including anti-adherents and/or glidants) as excipients. Suitable lubricants include, but are not limited to, either individually or in combination, glyceryl behapate (e.g., Compritol™ 888 of Gattefosse); stearic acid and salts thereof, including magnesium, calcium and sodium stearates; hydrogenated vegetable oils (e.g., Sterotex™ of Abitec); colloidal silica; talc; waxes; boric acid; sodium benzoate; sodium acetate; sodium fumarate; sodium chloride; DL-leucine; PEG (e.g., Carbowax™ 4000 and Carbowax™ 6000 of the Dow Chemical Company); sodium oleate; sodium lauryl sulfate; and magnesium lauryl sulfate. Such lubricants, if present, constitute in total about 0.1% to about 10%, preferably about 0.2% to about 8%, and more preferably about 0.25% to about 5%, of the total weight of the pharmaceutical composition.

Magnesium stearate is a preferred lubricant used, for example, to reduce friction between the equipment and granulated mixture during compression of tablet formulations.

Suitable anti-adherents include, but are not limited to, talc, cornstarch, DL-leucine, sodium lauryl sulfate and metallic stearates. Talc is a preferred anti-adherent or glidant used, for example, to reduce formulation sticking to equipment surfaces and also to reduce static in the blend. Talc, if present, constitutes about 0.1% to about 10%, more preferably about 0.25% to about 5%, and still more preferably about 0.5% to about 2%, of the total weight of the pharmaceutical composition.

Glidants can be used to promote powder flow of a solid formulation. Suitable glidants include, but are not limited to, colloidal silicon dioxide, starch, talc, tribasic calcium phosphate, powdered cellulose and magnesium trisilicate. Colloidal silicon dioxide is particularly preferred.

Other excipients such as colorants, flavors and sweeteners are known in the pharmaceutical art and can be used in pharmaceutical compositions of the present invention. Tablets can be coated, for example with an enteric coating, or uncoated. Compositions of the invention can further comprise, for example, buffering agents.

Optionally, one or more effervescent agents can be used as disintegrants and/or to enhance organoleptic properties of pharmaceutical compositions of the invention. When present in pharmaceutical compositions of the invention to promote dosage form disintegration, one or more effervescent agents are preferably present in a total amount of about 30% to about 75%, and preferably about 45% to about 70%, for example about 60%, by weight of the pharmaceutical composition.

According to a particularly preferred embodiment of the invention, an effervescent agent, present in a solid dosage form in an amount less than that effective to promote disintegration of the dosage form, provides improved dispersion of the drug in an aqueous medium. Without being bound by theory, it is believed that the effervescent agent is effective to accelerate dispersion of the drug, from the dosage form in the gastrointestinal tract, thereby further enhancing absorption and rapid onset of therapeutic effect. When present in a pharmaceutical composition of the invention to promote intragastrointestinal dispersion but not to enhance disintegration, an effervescent agent is preferably present in an amount of about 1% to about 20%, more preferably about 2.5% to about 15%, and still more preferably about 5% to about 10%, by weight of the pharmaceutical composition.

An "effervescent agent" herein is an agent comprising one or more compounds which, acting together or individually, evolve a gas on contact with water. The gas evolved is generally oxygen or, most commonly, carbon dioxide. Preferred effervescent agents comprise an acid and a base that react in the presence of water to generate carbon dioxide gas. Preferably, the base comprises an alkali metal or alkaline earth metal carbonate or bicarbonate and the acid comprises an aliphatic carboxylic acid.

Non-limiting examples of suitable bases as components of effervescent agents useful in the invention include carbonate salts (e.g., calcium carbonate), bicarbonate salts (e.g., sodium bicarbonate), sesquicarbonate salts, and mixtures thereof. Calcium carbonate is a preferred base.

Non-limiting examples of suitable acids as components of effervescent agents and/or solid acids useful in the invention include citric acid, tartaric acid (as D-, L-, or D/L-tartaric acid), malic acid, maleic acid, fumaric acid, adipic acid, succinic acid, acid anhydrides of such acids, acid salts of such acids, and mixtures thereof. Citric acid is a preferred acid.

In a preferred embodiment of the invention, where the effervescent agent comprises an acid and a base, the weight ratio of the acid to the base is about 1:100 to about 100:1, more preferably about 1:50 to about 50:1, and still more preferably about 1:10 to about 10:1. In a further preferred embodiment of the invention, where the effervescent agent comprises an acid and a base, the ratio of the acid to the base is approximately stoichiometric.

Excipients which solubilize metal salts of drugs typically have both hydrophilic and hydrophobic regions, or are preferably amphiphilic or have amphiphilic regions. One type of amphiphilic or partially-amphiphilic excipient comprises an amphiphilic polymer or is an amphiphilic polymer. A specific amphiphilic polymer is a polyalkylene glycol, which is commonly comprised of ethylene glycol and/or propylene glycol subunits. Such polyalkylene glycols can be esterified at their termini by a carboxylic acid, ester, acid anhyride or other suitable moiety. Examples of such excipients include poloxamers (symmetric block copolymers of ethylene glycol and propylene glycol; e.g., poloxamer 237), polyalkyene glycolated esters of tocopherol (including esters formed from a di- or multi-functional carboxylic acid; e.g., d-alpha-tocopherol polyethylene glycol-1000 succinate), and macrogolglycerides (formed by alcoholysis of an oil and esterification of a polyalkylene glycol to produce a mixture of mono-, di- and tri-glycerides and mono- and di-esters; e.g., stearoyl macrogol-32 glycerides). Such pharmaceutical compositions are advantageously administered orally.

Pharmaceutical compositions of the present invention can comprise about 10% to about 50%, about 25% to about 50%, about 30% to about 45%, or about 30% to about 35% by weight of drug; about 10% to about 50%, about 25% to about 50%, about 30% to about 45%, or about 30% to about 35% by weight of a an excipient which inhibits crystallization; and about 5% to about 50%, about 10% to about 40%, about 15% to about 35%, or about 30% to about 35% by weight of a binding agent. In one example, the weight ratio of the drug to the excipient which inhibits crystallization to binding agent is about 1 to 1 to 1.

Solid dosage forms of the invention can be prepared by any suitable process, not limited to processes described herein.

An illustrative process comprises (a) a step of blending a salt of the invention with one or more excipients to form a blend, and (b) a step of tableting or encapsulating the blend to form tablets or capsules, respectively.

In a preferred process, solid dosage forms are prepared by a process comprising (a) a step of blending a drug salt of the invention with one or more excipients to form a blend, (b) a step of granulating the blend to form a granulate, and (c) a step of tableting or encapsulating the blend to form tablets or capsules respectively. Step (b) can be accomplished by any dry or wet granulation technique known in the art, but is preferably a dry granulation step. A salt of the present invention is advantageously granulated to form particles of about 1 micrometer to about 100 micrometer, about 5 micrometer to about 50 micrometer, or about 10 micrometer to about 25 micrometer. One or more diluents, one or more disintegrants and one or more binding agents are preferably added, for example in the blending step, a wetting agent can optionally be added, for example in the granulating step, and one or more disintegrants are preferably added after granulating but before tableting or encapsulating. A lubricant is preferably added before tableting. Blending and granulating can be performed independently under low or high shear. A process is preferably selected that forms a granulate that is uniform in drug content, that readily disintegrates, that flows with sufficient ease so that weight variation can be reliably controlled during capsule filling or tableting, and that is dense enough in bulk so that a batch can be processed in the selected equipment and individual doses fit into the specified capsules or tablet dies.

In an alternative embodiment, solid dosage forms are prepared by a process that includes a spray drying step, wherein the drug is suspended with one or more excipients in one or more sprayable liquids, preferably a non-protic (e.g., non-aqueous or non-alcoholic) sprayable liquid, and then is rapidly spray dried over a current of warm air.

A granulate or spray dried powder resulting from any of the above illustrative processes can be compressed or molded to prepare tablets or encapsulated to prepare capsules. Conventional tableting and encapsulation techniques known in the art can be employed. Where coated tablets are desired, conventional coating techniques are suitable.

Excipients for tablet compositions of the invention are preferably selected to provide a disintegration time of less than about 30 minutes, preferably about 25 minutes or less, more preferably about 20 minutes or less, and still more preferably about 15 minutes or less, in a standard disintegration assay.

Uses for sertraline are well known in the art and include the treatment of major depressive disorder, panic disorder, posttraumatic stress disorder, premenstrual dysphoric disorder and obsessive-compulsive disorder. The dosage and administration for sertraline compositions of the present invention can be determined using routine methods in the art but will generally fall between 10 mg to 200 mg/day with an initial dose in adults of about 25–50 mg/day.

Pharmaceutically acceptable salts and solvates of sertraline can be administered by controlled- or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Chemg-ju, Controlled Release Dosage Form Design, 2 Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the sertraline salts, sertraline solvates, and compositions of the invention. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of sertraline and thus effect controlled delivery of the drug. Examples of specific anion exchangers include, but are not limited to, Duolite® A568 and Duolite® AP143 (Rohm&Haas, Spring House, Pa. USA).

One embodiment of the invention encompasses a unit dosage form which comprises a pharmaceutically acceptable salt of sertraline (e.g., a benzoate, HBr, or lactate salt), or a polymorph, solvate, hydrate, dehydrate, co-crystal, anhydrous, or amorphous form thereof, and one or more pharmaceutically acceptable excipients or diluents, wherein the pharmaceutical composition or dosage form is formulated for controlled-release. Specific dosage forms utilize an osmotic drug delivery system.

A particular and well-known osmotic drug delivery system is referred to as OROS® (Alza Corporation, Mountain View, Calif. USA). This technology can readily be adapted for the delivery of compounds and compositions of the invention. Various aspects of the technology are disclosed in U.S. Pat. Nos. 6,375,978 B1; 6,368,626 B1; 6,342,249 B1; 6,333,050 B2; 6,287,295 B1; 6,283,953 B1; 6,270,787 B1; 6,245,357 B1; and 6,132,420; each of which is incorporated herein by reference. Specific adaptations of OROS® that can be used to administer compounds and compositions of the invention include, but are not limited to, the OROS® Push-Pull™, Delayed Push-Pull™, Multi-Layer Push-Pull™, and Push-Stick™ Systems, all of which are well known. See, e.g., http://www.alza.com. Additional OROS® systems that can be used for the controlled oral delivery of compounds and compositions of the invention include OROS®-CT and L-OROS®. Id.; see also, Delivery Times, vol. II, issue II (Alza Corporation).

Conventional OROS® oral dosage forms are made by compressing a drug powder (e.g. sertraline salt or sertraline solvate) into a hard tablet, coating the tablet with cellulose derivatives to form a semi-permeable membrane, and then drilling an orifice in the coating (e.g., with a laser). (Kim, Chemg-ju, Controlled Release Dosage Form Design, 231–238 Technomic Publishing, Lancaster, Pa.: 2000). The advantage of such dosage forms is that the delivery rate of the drug is not influenced by physiological or experimental conditions. Even a drug with a pH-dependent solubility can be delivered at a constant rate regardless of the pH of the delivery medium. But because these advantages are provided by a build-up of osmotic pressure within the dosage form after administration, conventional OROS® drug delivery systems cannot be used to effectively delivery drugs with low water solubility. Id. at 234. This invention does, however, encompass the incorporation of sertraline, and non-salt isomers and isomeric mixtures thereof, into OROS® dosage forms.

A specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a dry or substantially dry state drug layer located within the cavity adjacent the exit orifice and in direct or indirect contacting relationship with the expandable layer; and a flow-promoting layer interposed between the inner surface of the wall and at least the external surface of the drug layer located within the cavity, wherein the drug layer comprises a salt of sertraline, or a polymorph, solvate, hydrate, dehydrate, co-crystal, anhydrous, or amorphous form thereof. See U.S. Pat. No. 6,368,626, the entirety of which is incorporated herein by reference.

Another specific dosage form of the invention comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being adapted to resist compaction forces sufficient to form a compacted drug layer without significant exudation of the liquid, active agent formulation, the dosage form optionally having a placebo layer between the exit orifice and the drug layer, wherein the active agent formulation comprises a salt of sertraline, or a polymorph, solvate, hydrate, dehydrate, co-crystal, anhydrous, or amorphous form thereof. See U.S. Pat. No. 6,342,249, the entirety of which is incorporated herein by reference.

The present invention is also directed to a method for treating anorexia in a subject suffering from anorexia or the symptoms of anorexia comprising administering to said subject an effective amount of an acid salt or solvate of sertraline. The present invention is also directed to methods for treating impulse disorders such as trichotillomania, pathological gambling, kleptomania and pyromania in a subject suffering from one of said impulse disorders comprising administering to said subject an effective amount of an acid salt or solvate of sertraline. The present invention is also directed to methods for treating onychophagia in a subject suffering from onychophagia comprising administering to said subject an effective amount of an acid salt or solvate of sertraline. The present invention is also directed to methods for treating premenstrual syndrome (also referred to herein as "premenstrual dysphoric disorder") in a subject suffering from premenstrual syndrome comprising administering to said subject an effective amount of an acid salt or solvate of sertraline. The present invention is also directed to methods for treating psychotic disorders of the schizophrenic type in a subject suffering from said psychotic disorders or suffering from such symptoms as anxiety, agitation, tension, excessive aggression, social withdrawal or emotional withdrawal comprising administering to said subject an effective amount of an acid salt or solvate of sertraline. The present invention is also directed to methods for treating inflammatory disorders such as psoriasis and arthritis in a subject suffering from an inflammatory disorder or inflammatory disorders comprising administering to said subject an effective amount of an acid salt or solvate of sertraline. The present invention is also directed to methods for treating conciftions characterized by a hyperactive immune system such as rheumatoid arthritis and lupus in a subject suffering from said conditions comprising administering to said subject an effective amount of an acid salt or solvate of sertraline. The present invention is also directed to methods for treating mental depression in a mentally-depressed subject comprising administering to said subject an effective amount of an acid salt or solvate of sertraline. The present invention is also directed to methods for treating anxiety-related disorders such as panic disorder, generalized anxiety disorder, agoraphobia, simple phobias, social phobia, posttraumatic stress disorder, obsessive-compulsive disorder and avoidant personality disorder in a subject suffering from one or more of said anxiety-related disorders comprising administering to said subject an effective amount of an acid salt or solvate of sertraline.

The present invention is particularly directed to methods for treating anxiety related disorders as described in the previous paragraph wherein said anxiety-related disorder is obsessive-compulsive disorder. The present invention is also directed to methods for treating chemical dependency in a subject suffering from chemical dependency comprising administering to said subject an effective amount of an acid salt or solvate of sertraline.

According to the present invention, the packaging of pharmaceutical compositions can be accomplished via a container for containing the pharmaceutical compositions and may also include divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle which is in turn contained within a box.

An example of such a container is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

The invention will now be described in further detail, by way of example, with reference to the accompanying drawings.

EXAMPLES

Analytical Methods

DSC analysis of the samples was performed using a Q1000 Differential Scanning Calorimeter (TA Instruments, New Castle, Del., U.S.A.), which uses Advantage for QW-Series, version 1.0.0.78, Thermal Advantage Release 2.0 (2001 TA Instruments-Water LLC). In addition, the analysis software used was Universal Analysis 2000 for Windows 95/95/2000/NT, version 3.1E;Build 3.1.0.40 (2001 TA Instruments-Water LLC).

For the DSC analysis, the purge gas used was dry nitrogen, the reference material was an empty aluminum pan that was crimped, and the sample purge was 50 mL/minute.

DSC analysis of the sample was performed by placing the sertraline salt sample in an aluminum pan with a crimped pan closure. The starting temperature was typically 20° C. with a heating rate of 10° C./minute, and the ending temperature was 200° C. All reported DSC transitions represent the temperature of endothermic or exothermic transition at their respective peaks with an error of +/−2 degrees C., unless otherwise indicated.

TGA analysis of samples was performed using a Q500 Thermogravimetric Analyzer (TA Instruments, New Castle, Del., U.S.A.), which uses Advantage for QW-Series, version 1.0.0.78, Thermal Advantage Release 2.0 (2001 TA Instruments-Water LLC). In addition, the analysis software used was Universal Analysis 2000 for Windows 95/95/2000/NT, version 3.1E;Build 3.1.0.40 (2001 TA Instruments-Water LLC).

For the TGA experiments, the purge gas used was dry nitrogen, the balance purge was 40 mL/minute $N_2$, and the sample purge was 60 mL/minute $N_2$.

TGA of the sample was performed by placing the sertraline salt sample in a platinum pan. The starting temperature was typically 20° C. with a heating rate of 10° C./minute, and the ending temperature was 300° C.

A powder X-ray diffraction pattern for the samples was obtained using a D/Max Rapid, Contact (Rigaku/MSC, The Woodlands, Tex., U.S.A.), which uses as its control software RINT Rapid Control Software, Rigaku Rapid/XRD, version 1.0.0 (1999 Rigaku Co.). In addition, the analysis software used were RINT Rapid display software, version 1.18 (Rigaku/MSC), and JADE XRD Pattern Processing, versions 5.0 and 6.0 ((1995–2002, Materials Data, Inc.).

For the PXRD analysis, the acquisition parameters were as follows: source was Cu with a K line at 1.5406 Å; x-y stage was manual; collimator size was 0.3 mm; capillary tube (Charles Supper Company, Natick, Mass., U.S.A.) was 0.3 mm ID; reflection mode was used; the power to the X-ray tube was 46 kV; the current to the X-ray tube was 40 mA; the omega-axis was oscillating in a range of 0–5 degrees at a speed of 1 degree/minute; the phi-axis was spinning at an angle of 360 degrees at a speed of 2 degrees/second; 0.3 mm collimator; the collection time was 60 minutes; the temperature was room temperature; and the heater was not used. The sample was presented to the X-ray source in a boron rich glass capillary.

In addition, the analysis parameters were as follows: the integration 2-theta range was 2–60 degrees; the integration chi range was 0–360 degrees; the number of chi segments was 1; the step size used was 0.02; the integration utility was cylint; normalization was used; dark counts were 8; omega offset was 180; and chi and phi offsets were 0.

The relative intensity of peaks in a diffractogram is not necessarily a limitation of the PXRD pattern because peak intensity can vary from sample to sample, e.g., due to crystalline impurities. Further, the angles of each peak can vary by about +/−0.1 degrees, preferably ±0.05. The entire pattern or most of the pattern peaks may also shift by about +/−0.1 degree due to differences in calibration, settings, and other variations from instrument to instrument and from operator to operator.

For PXRD data herein, including Table and Figures, each composition of the present invention may be characterized by any one, any two, any three, any four, any five, any six, any seven, any eight or more of the 2 theta angle peaks. Any one, two, three, four, five, or six DSC transitions can also be used to characterize the compositions of the present invention. The different combinations of the PXRD peaks and the DSC transitions can also be used to characterized the compositions.

The procedures for Raman acquisition, and filtering and binning are discussed below.

Acquisition

The sample was either left in the glass vial in which it was processed or an aliquot of the sample was transferred to a glass slide. The glass vial or slide was positioned in the sample chamber. The measurement was made using an Almega™ Dispersive Raman (Almega™ Dispersive Raman, Thermo-Nicolet, 5225 Verona Road, Madison, Wis. 53711-4495) system fitted with a 785 nm laser source. The sample was manually brought into focus using the microscope portion of the apparatus with a 10× power objective (unless otherwise noted), thus directing the laser onto the surface of the sample. The spectrum was acquired using the parameters outlined in Table I. (Exposure times and number of exposures may vary; changes to parameters will be indicated for each acquisition.)

Filtering and Binning

Each spectrum in a set was filtered using a matched filter of feature size 25 to remove background signals, including glass contributions and sample fluorescence. This is particularly important as large background signal or fluorescence limit the ability to accurately pick and assign peak positions in the subsequent steps of the binning process. Filtered spectra were binned using the peak pick and bin algorithm with the parameters given in Table II. The sorted cluster diagrams for each sample set and the corresponding cluster assignments for each spectral file were used to identify groups of samples with similar spectra, which was used to identify samples for secondary analyses.

TABLE I

Raman Spectral acquisition parameters

| Parameter | Setting Used |
|---|---|
| Exposure time (s) | 2.0 |
| Number of exposures | 10 |
| Laser source wavelength (nm) | 785 |
| Laser power (%) | 100 |
| Aperture shape | pin hole |
| Aperture size (um) | 100 |
| Spectral range ($cm^{-1}$) | 104–3428 |
| Grating position | Single |
| Temperature at acquisition (degrees C.) | 24.0 |

TABLE II

Raman Filtering and Binning Parameters

| Parameter | Setting Used |
|---|---|
| Filtering Parameters | |
| Filter type | Matched |
| Filter size | 25 |
| QC Parameters | |
| Peak Height Threshold | 1000 |
| Region for noise test ($cm^{-1}$) | 0–10000 |
| RMS noise threshold | 10000 |

TABLE II-continued

Raman Filtering and Binning Parameters

| Parameter | Setting Used |
|---|---|
| Automatically eliminate failed spectra | Yes |
| Region of Interest | |
| Include (cm$^{-1}$) | 104–3428 |
| Exclude region I (cm$^{-1}$) | |
| Exclude region II (cm$^{-1}$) | |
| Exclude region III (cm$^{-1}$) | |
| Exclude region IV (cm$^{-1}$) | |
| Peak Pick Parameters | |
| Peak Pick Sensitivity | Variable |
| Peak Pick Threshold | 100 |
| Peak Comparison Parameters | |
| Peak Window (cm$^{-1}$) | 2 |
| Analysis Parameters | |
| Number of clusters | Variable |

Methods of Making Sertraline Salts

The sertraline salts were made in CrystalMax™ (U.S. Pat. App. 20020048610, incorporated herein in its entirety) by the following procedure: A 100 mg/mL solution of sertraline free base in methanol was prepared. 20.0 microliters of the solution (2.0 mg of solid) was dispensed into vials and the solvent was evaporated under nitrogen. 0.5–0.55 and 1.0–1.1 equiv of each salt former was then dispensed into the vials from solvent (0.65 M salt former in methanol or THF), and the solvent was again evaporated. One or two appropriate solvents (e.g., methanol) were then dispensed into each vial. Each vial was crimp-sealed immediately following solvent addition. For combinations, the solvents were mixed together in a ratio of 3:7, unless otherwise indicated. Total solvent volume was about 52 microliters for samples with 0.5 equivalents of acid and about 46 microliters for samples with 1 equivalent of the salt former. All samples were heated at 60 degrees C. for 2 hours, cooled to 25 degrees C. for 1 week, and then cooled to 5 degrees C. Most samples crystallized at 60 degrees C., others at 25 degrees C., and still others at 5 degrees C.

Sertraline Benzoate Salts

There are two unique forms of the benzoate salt shown in FIG. 1A. There are some shifts in the bottom 4 patterns (Form A), which may indicate solvate formation or preferred orientation effects.

Figure 1B:
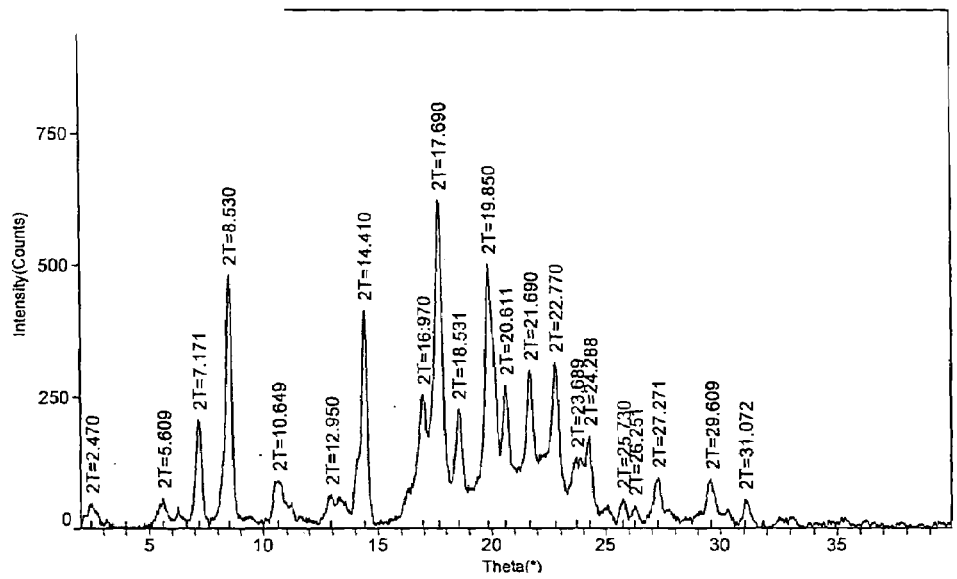
FIG. 1B—PXRD diffractogram of sertraline benzoate salt Form A
Figure 1C:
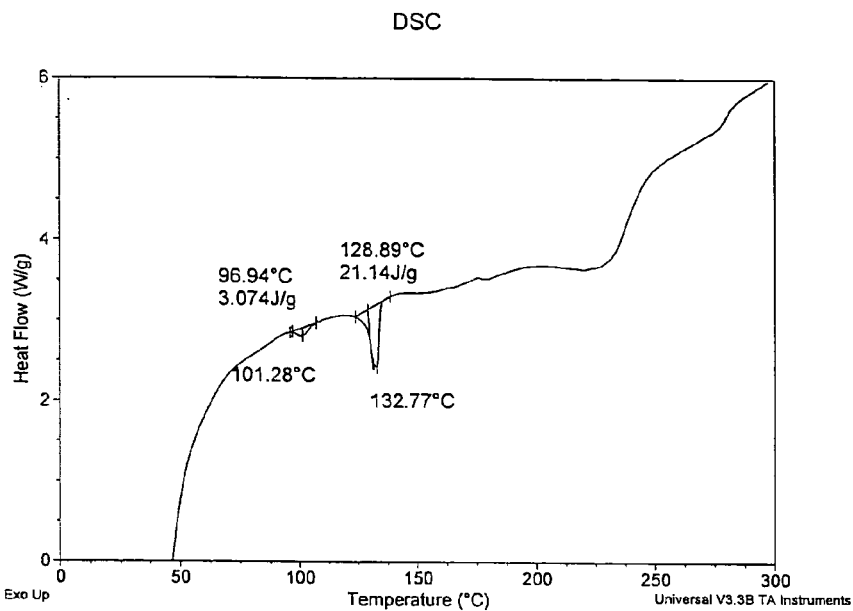
FIG. 1C—DSC thermogram of sertraline benzoate salt Form A

Form A can be characterized by PXRD peaks at 2-theta values of about 7.1, 8.5, 14.3, 17.6, and 19.9 degrees. DSC of form A showed an endotherm at about 133 degrees C. (See FIG. 1C). Form A of sertraline benzoate can be characterized by any one, any two, any three, any four, any five, or any six or more of the peaks in the PXRD diffractogram in FIG. 1B including, but not limited to, 7.17, 8.53, 14.41, 16.97, 17.69, 18.53, 19.85, 20.61, 21.69, and 22.77 degrees 2-theta.

Figure 1D:
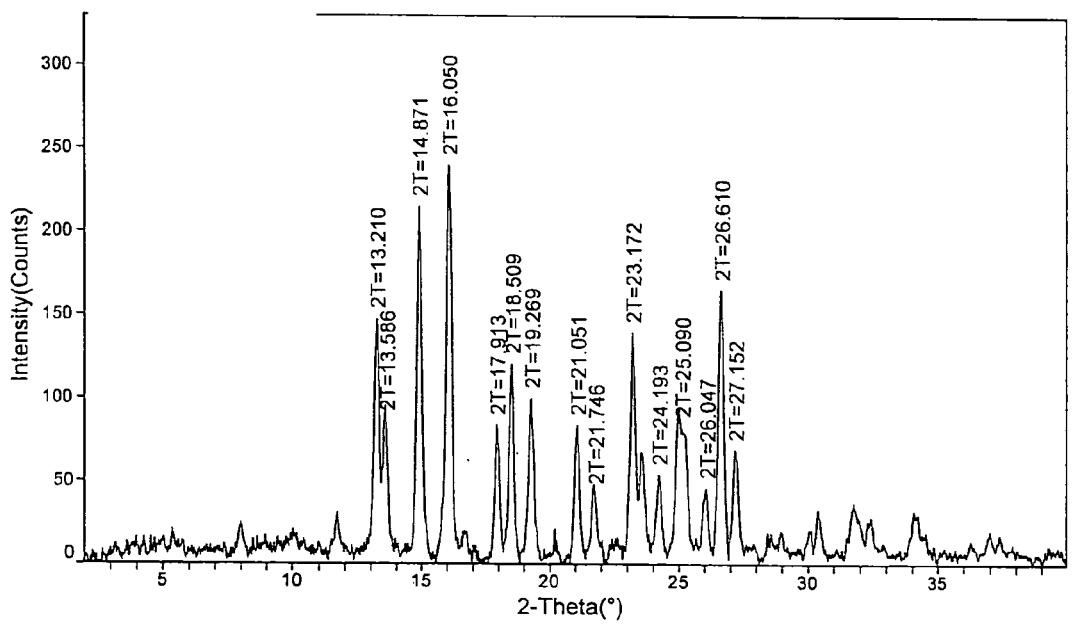
FIG. 1D—PXRD diffractogram of sertraline benzoate salt Form B
Figure 1E:
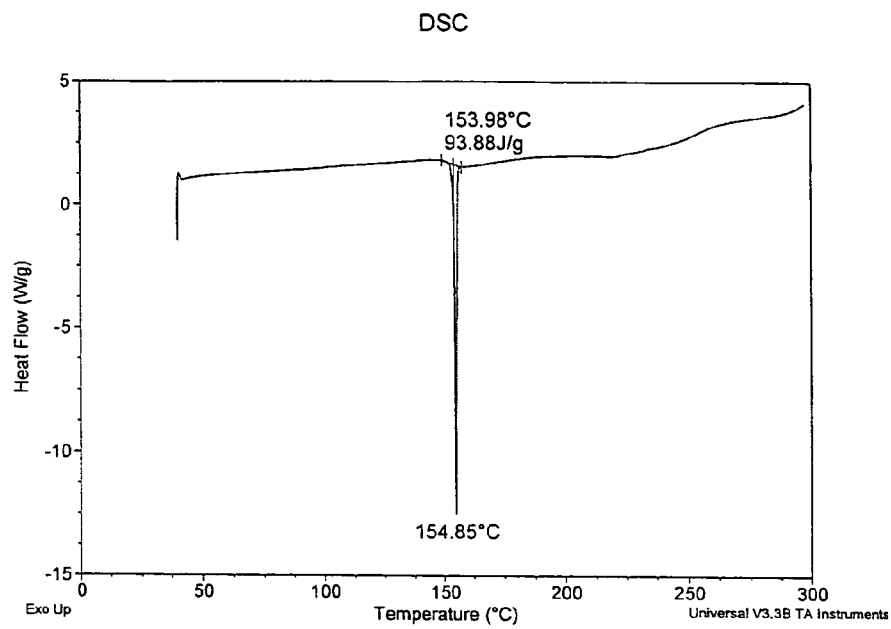
FIG. 1E—DSC thermogram of sertraline benzoate salt Form B

Form B (Solubility=0.4 mg/mL) can be characterized by PXRD peaks at about 2-theta values of 13.2, 14.9, 16.1, 18.5, 23.2, and 26.6 degrees. DSC of form B showed an endotherm at about 155 degrees C. (See FIG. 1E). Form B is the more stable form of the benzoate salts. Form B of sertraline benzoate can be characterized by any one, any two, any three, any four, any five, or any six or more of the peaks in the PXRD diffractogram in FIG. 1D including, but not limited to, 13.21, 14.87, 16.05, 17.91, 18.51, 19.27, 21.05, 23.17, and 26.61 degrees 2-theta.

Crystallization of sertraline benzoate was completed in several solvent systems. All binary solvent systems were prepared in a 34:14 volume ratio. Sample 540__120_D1 was crystallized in a water:acetonitrile mixture. Sample 540__257_G2 was crystallized in acetonitrile. Sample 540__310_B2 was crystallized in water. Sample 540__325_D1 was crystallized in an isopropyl acetate:n-heptane mixture. Sample 540__325_F5 was crystallized in an acetonitrile:tetrahydrofuran mixture. Sample 540__355_C1 was crystallized in an n-heptane:water mixture.

Sertraline HBr Salts

Figure 2A:
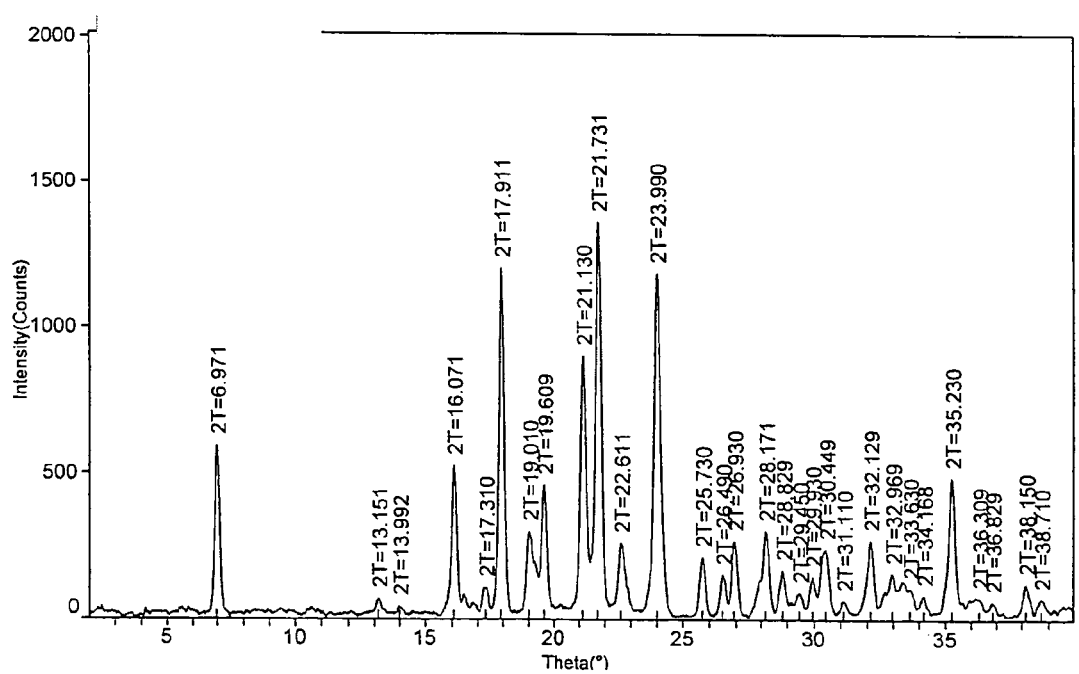
FIG. 2A—PXRD diffractogram of sertraline HBr salt
Figure 2B:
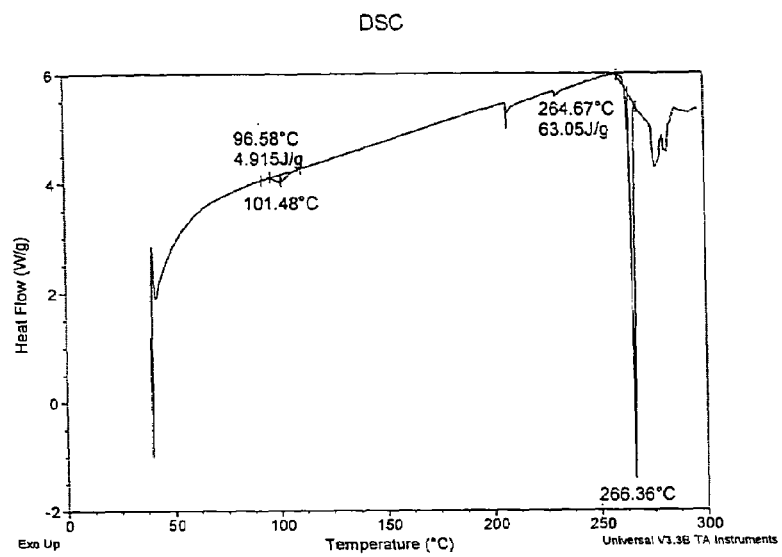
FIG. 2B—DSC thermogram of sertraline HBr salt

Characteristic PXRD peaks of sertraline HBr salt (Solubility=0.6 mg/mL) can include 2-theta values of 7.0, 16.1, 17.9, 21.2, 21.7, 24.0, and 35.2 degrees. The compound has an endothermic transition at 266 degrees C. (See FIG. 2B). No sertraline HBr salt polymorphism was observed. Sertraline HBr can be characterized by any one, any two, any three, any four, any five, or any six or more of the peaks in the PXRD diffractogram in FIG. 2A including, but not limited to, 6.97, 16.07, 17.91, 19.61, 21.13, 21.73, 23.99, and 35.23 degrees 2-theta.

Crystallization of sertraline HBr was completed in several solvent systems. All binary solvent systems were prepared in a 34:14 volume ratio. Solvent systems used include a tetrahydrofuran:acetonitrile mixture, a tetrahydrofuran:ethanol mixture, a tetrahydrofuran:n-heptane mixture, an iso-butanol:n-heptane mixture, a propylene glycol:2-propanol mixture, a propylene glycol:acetonitrile mixture, water, 2-propanol, an n-heptane:ethanol mixture, a propylene glycol:n-heptane mixture, and a propylene glycol: iso-butanol mixture.

Sertraline Esylate Salts

Figure 3A:
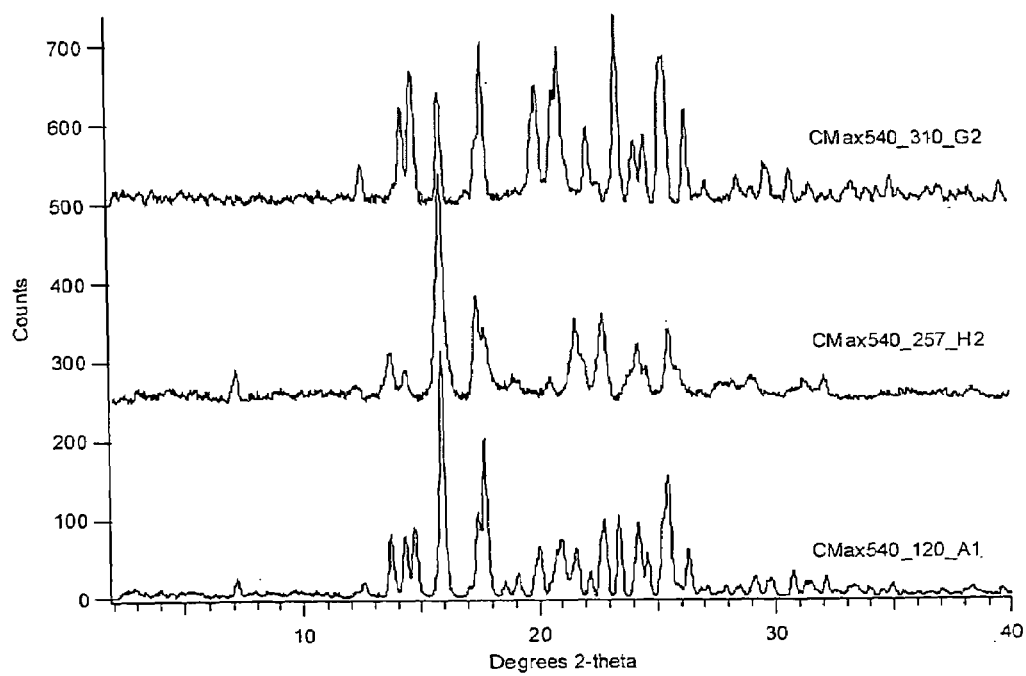
FIG. 3A—Compilation of PXRD data for sertraline esylate salts
Figure 3B:
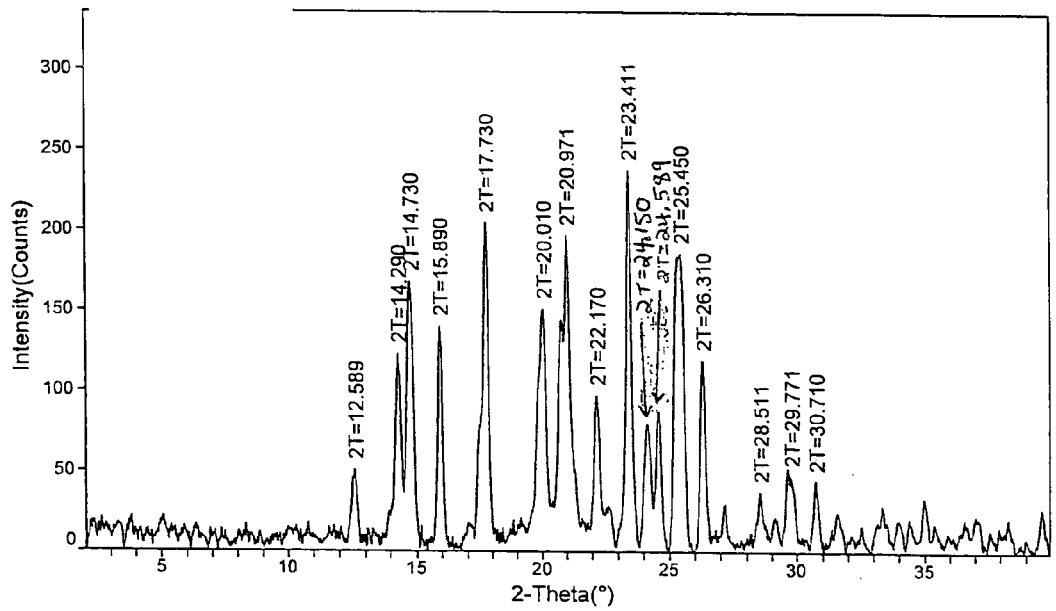
FIG. 3B—PXRD diffractogram of sertraline esylate salt Form A
Figure 3C:
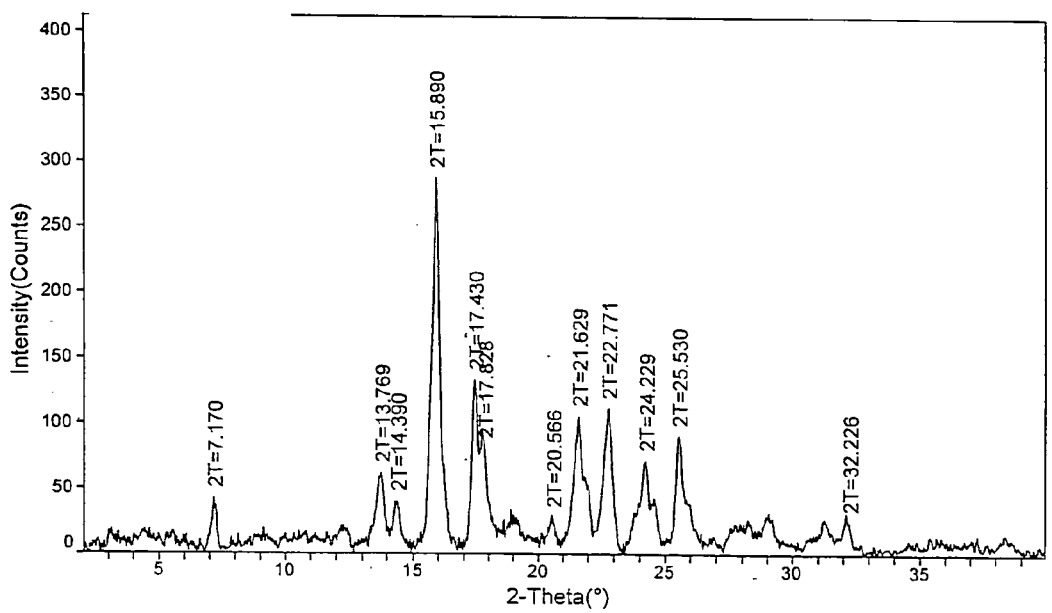
FIG. 3C—PXRD diffractogram of sertraline esylate salt Form B
Figure 3D:
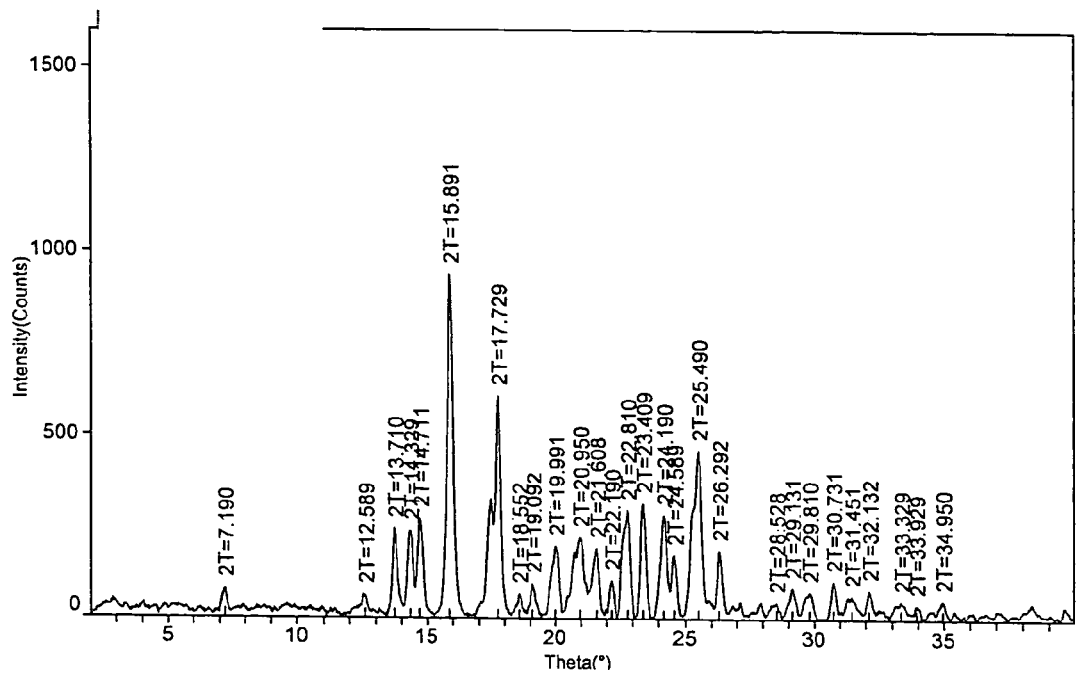
FIG. 3D—PXRD diffractogram of sertraline esylate salt Forms A and B mixture
Figure 3E:
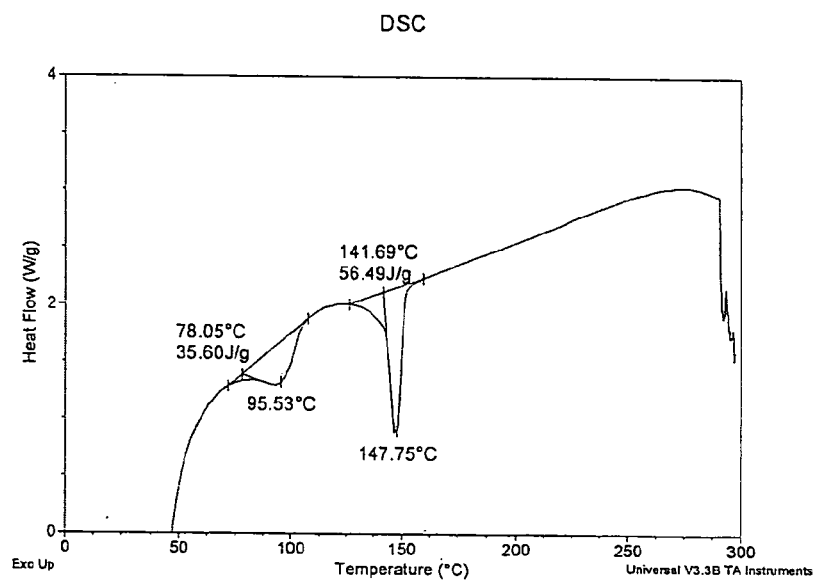
FIG. 3E—DSC thermogram of sertraline esylate salt Forms A and B mixture

Two polymorphs of sertraline esylate salt are evident from the PXRD data. The first is represented by 540__310_G2 (Form A). The second is represented by 540__257_H2 (Form B). Sample 540__120_A1 is most likely a mixture of the two polymorphs. The DSC transitions of 540__120_A1 (See FIG. 3E) most likely correspond to the endothermic transitions of the two polymorphs. These transitions occurred at about 96 and 148 degrees C. Sertraline esylate Form A (Solubility=1.7 mg/mL) can be characterized by any one, any two, any three, any four, any five, or any six or more of the peaks in the PXRD diffractogram in FIG. 3B including, but not limited to, 12.59, 14.29, 14.73, 15.89, 17.73, 20.01, 20.97, 22.17, 23.41, 24.15, 24.59, 25.45, and 26.31 degrees 2-theta. Sertraline esylate Form B can be characterized by any one, any two, any three, any four, any five, or any six or more of the peaks in the PXRD diffractogram in FIG. 3C including, but not limited to, 7.17, 13.77, 15.89, 17.43, 21.63, 22.77, 24.23, and 25.53 degrees 2-theta.

Crystallization of sertraline esylate was completed in several solvent systems. Sample 540__120_A1 was crystallized in n-heptane. Sample 540__257_H2 was crystallized in isopropyl acetate. Sample 540__310_G2 was crystallized in isopropyl acetate.

Sertraline Lactate Salts

Figure 4A:
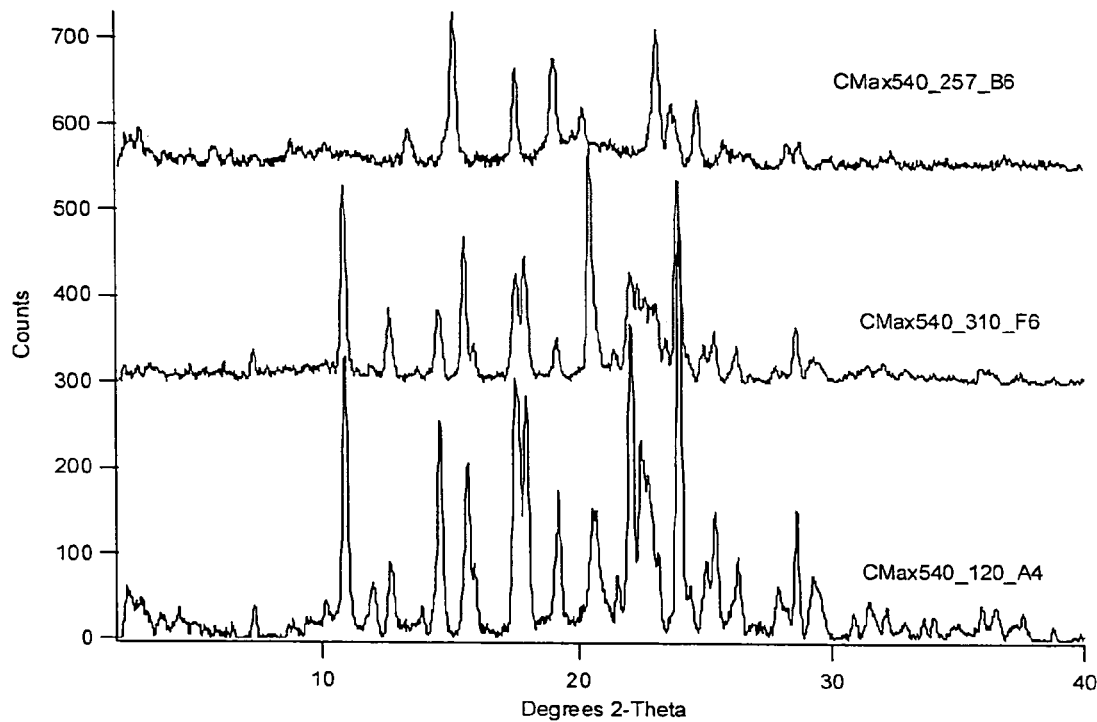
FIG. 4A—Compilation of PXRD data for sertraline lactate salts
Figure 4B:
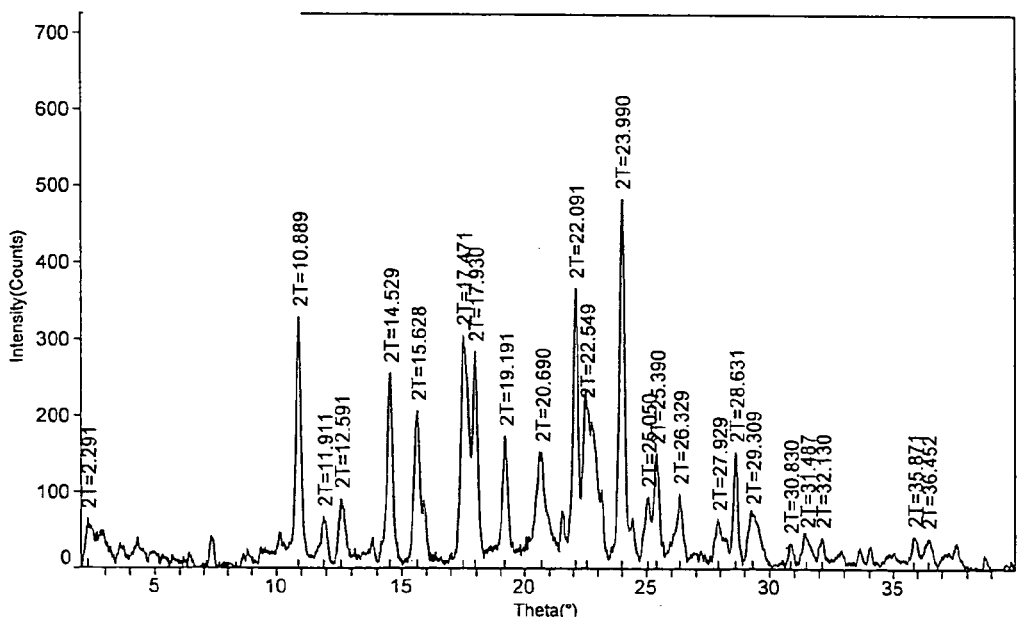
FIG. 4B—PXRD diffractogram of sertraline lactate salt Form A
Figure 4C:
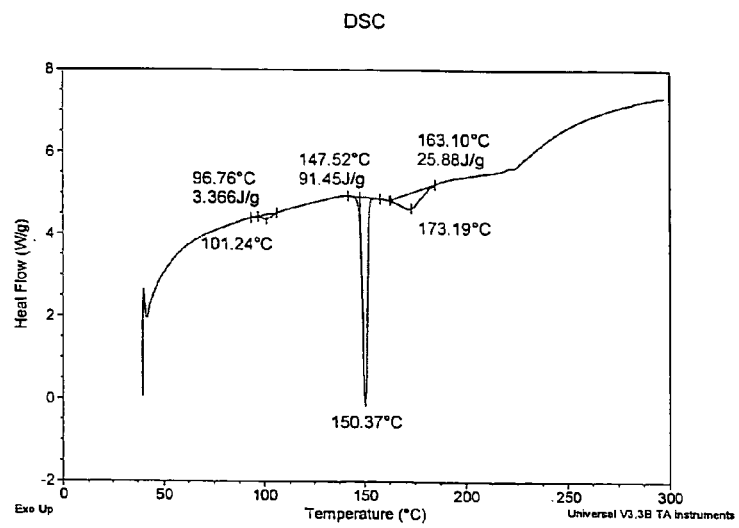
FIG. 4C—DSC thermogram of sertraline lactate salt Form A
Figure 4D:
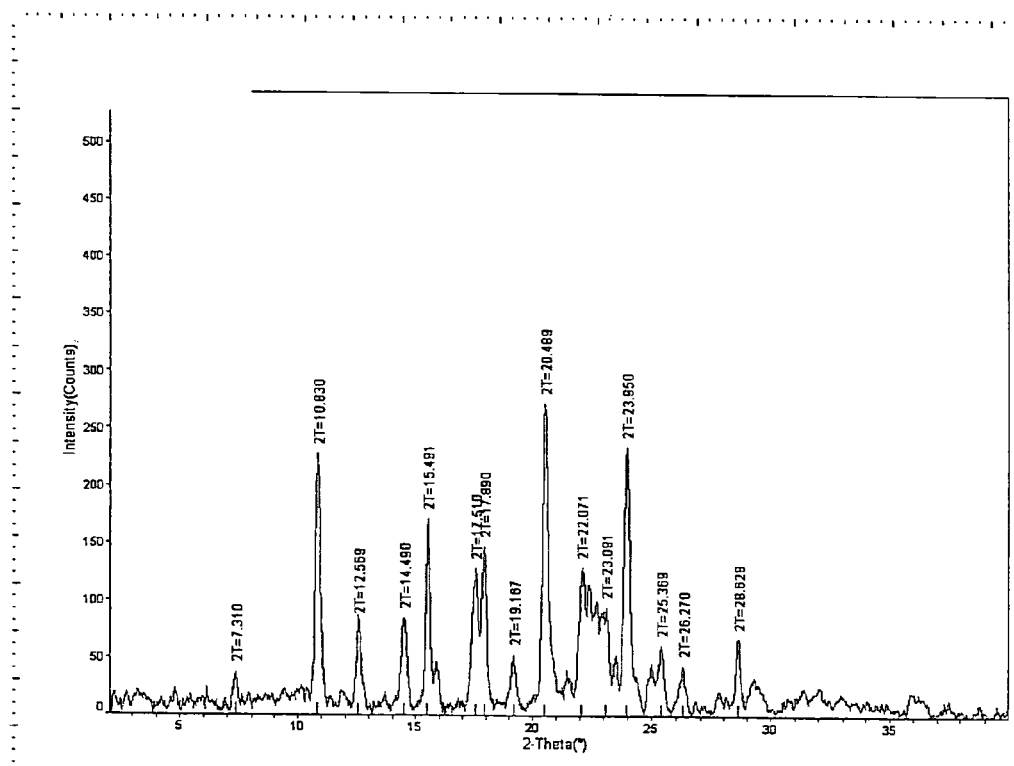
FIG. 4D—PXRD diffractogram of sertraline lactate salt Form B
Figure 4E:
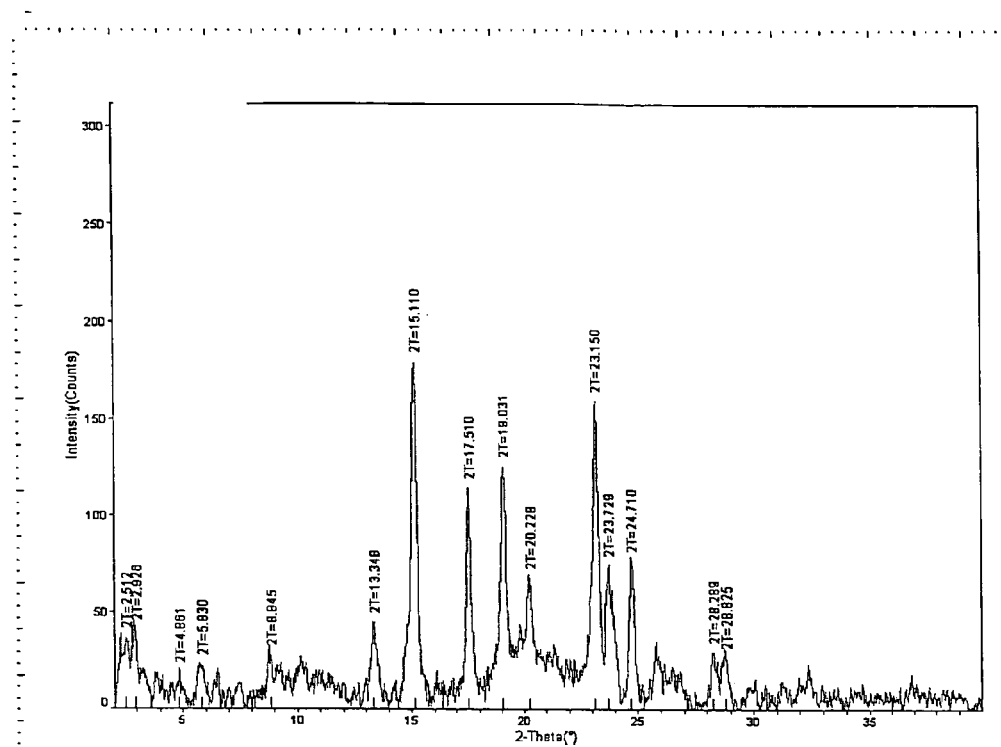
FIG. 4E—PXRD diffractogram of sertraline lactate salt hydrate

Two polymorphs of sertraline lactate salt are evident from the PXRD data. Samples 540__120_A4 and 540__310_F6 show PXRD data which, upon comparison, display differences in peak intensity as well as a distinctive feature at about 11.9 degrees 2-theta (See FIG. 4A). Sample 540__257_B6 may be a hydrate of sertraline lactate salt. Sertraline lactate Form A (Solubility=1.9 mg/mL) can be characterized by any one, any two, any three, any four, any five, or any six or more of the peaks in the PXRD diffractogram in FIG. 4B including, but not limited to, 10.89, 14.53, 15.63, 17.47, 17.93, 19.19, 20.69, 22.09, and 23.99 degrees 2-theta. DSC of sertraline lactate Form A showed an endothermic transition at about 150 degrees C. (See FIG. 4C). Sertraline lactate Form B can be characterized by any one, any two, any three, any four, any five, or any six or more of the peaks in the PXRD diffractogram in FIG. 4D including, but not limited to, 10.83, 12.57, 14.49, 15.49, 17.51, 17.89, 20.49, 22.07, and 23.95 degrees 2-theta. A hydrate of sertraline lactate can be characterized by any one, any two, any three, any four, any five, or any six or more of the peaks in the PXRD diffractogram in FIG. 4E including, but not limited to, 13.35, 15.11, 17.51, 19.03, 20.23, 23.15, 23.73, and 24.71 degrees 2-theta.

Crystallization of sertraline lactate was completed in several solvent systems. All binary solvent systems were prepared in a 34:14 volume ratio. Sertraline lactate form A was crystallized in an acetonitrile:propylene glycol mixture. Sertraline lactate form B was crystallized in acetonitrile. The hydrate of sertraline lactate was crystallized in water.

Sertraline Besylate Salts

Figure 5A:
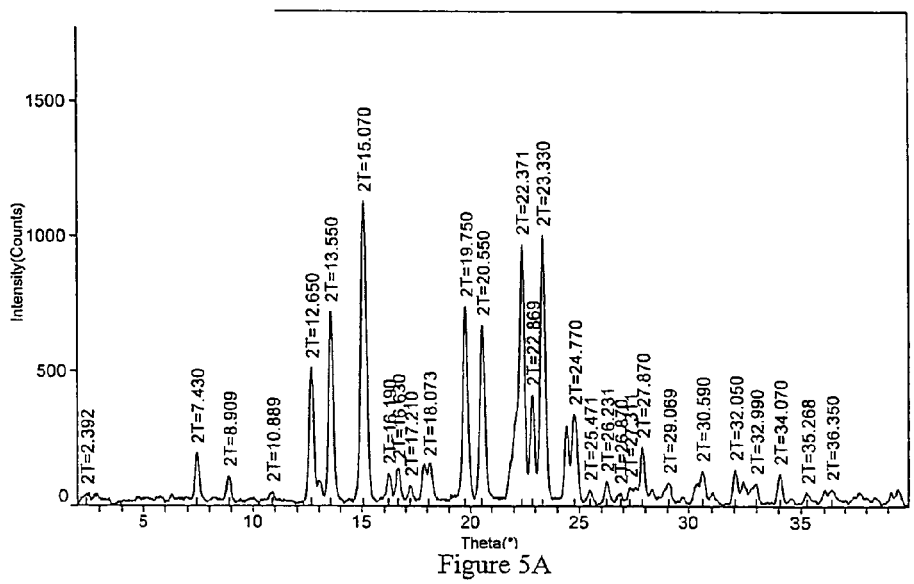
FIG. 5A—PXRD diffractogram of sertraline besylate salt
Figure 5B:
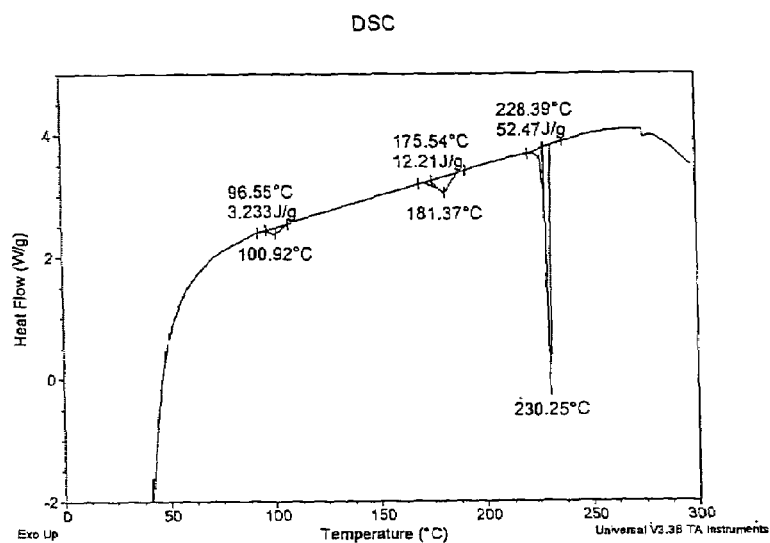
FIG. 5B—DSC thermogram of sertraline besylate salt

Sertraline besylate salt (Solubility=0.3 mg/mL) was prepared according to the methods described herein and was characterized by PXRD and DSC. Sertraline besylate salt can be characterized by any one, any two, any three, any four, any five, or any six or more of the peaks in the PXRD diffractogram in FIG. 5A including, but not limited to, 7.43, 12.65, 13.55, 15.07, 19.75, 20.55, 22.37, 23.33, 24.77, and 27.87 degrees 2-theta. DSC of sertraline besylate showed an endothermic transition at about 230 degrees C. (See FIG. 5B).

Crystallization of sertraline besylate was completed in several solvent systems. All binary solvent systems were prepared in a 34:14 volume ratio. Sertraline besylate was crystallized in a 2-propanol: tetrahydrofuran mixture, in ethanol, in water, and in acetonitrile.

Sertraline p-Tosylate Salt

Figure 6A:
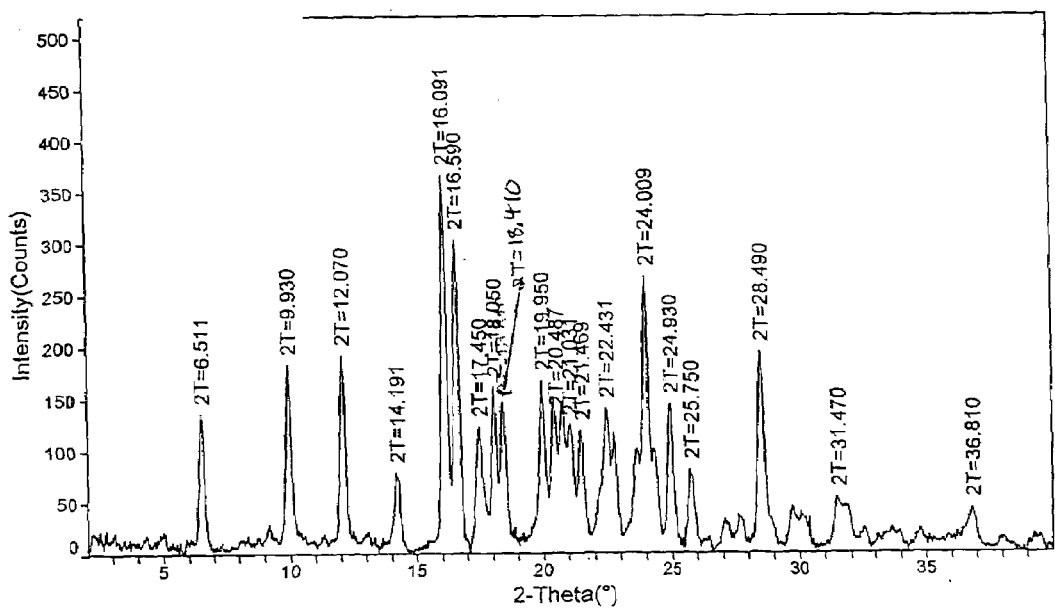
FIG. 6A—PXRD diffractogram of sertraline p-tosylate salt
Figure 6B:
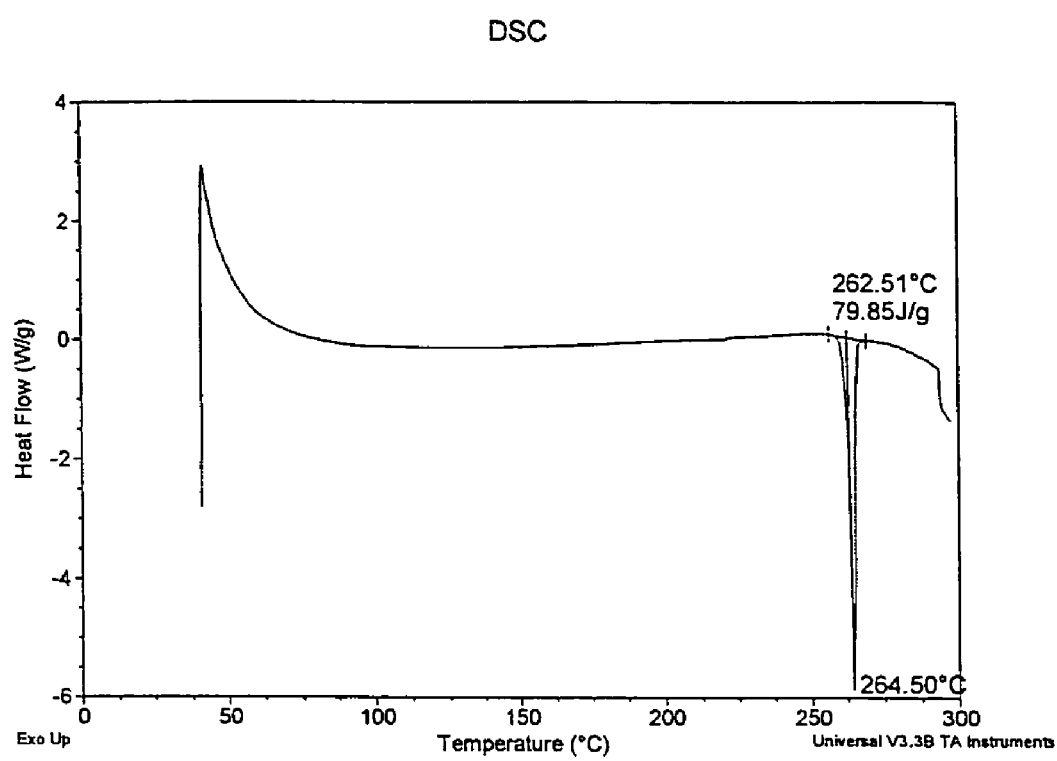
FIG. 6B—DSC thermogram of sertraline p-tosylate salt

Polymorphism was not observed in the sertralinep-tosylate salt. Sertralinep-tosylate salt (Solubility=0.1 mg/mL) can be characterized by any one, any two, any three, any four, any five, or any six or more of the peaks in the PXRD diffractogram in FIG. 6A including, but not limited to, 6.51, 9.93, 12.07, 16.09, 16.59, 18.05, 19.95, 20.49, 21.03, 21.47, 22.43, 24.01, 24.93, and 28.49 degrees 2-theta. DSC of sertralinep-tosylate salt showed an endothermic transition at about 265 degrees C. (See FIG. 6B).

Crystallization of sertralinep-tosylate was completed from several solvent systems. All binary solvent systems were prepared in a 34:14 volume ratio. Sample 540_257_B3 was crystallized from ethanol. Sample 540_257_H11 was crystallized from a 2-propanol:n-heptane mixture. Sample 540_257_H12 was crystallized from an n-heptane:acetonitrile mixture. Sample 540_310_E3 was crystallized from isopropyl acetate.

Sertraline Mesylate Salt

Figure 7A:
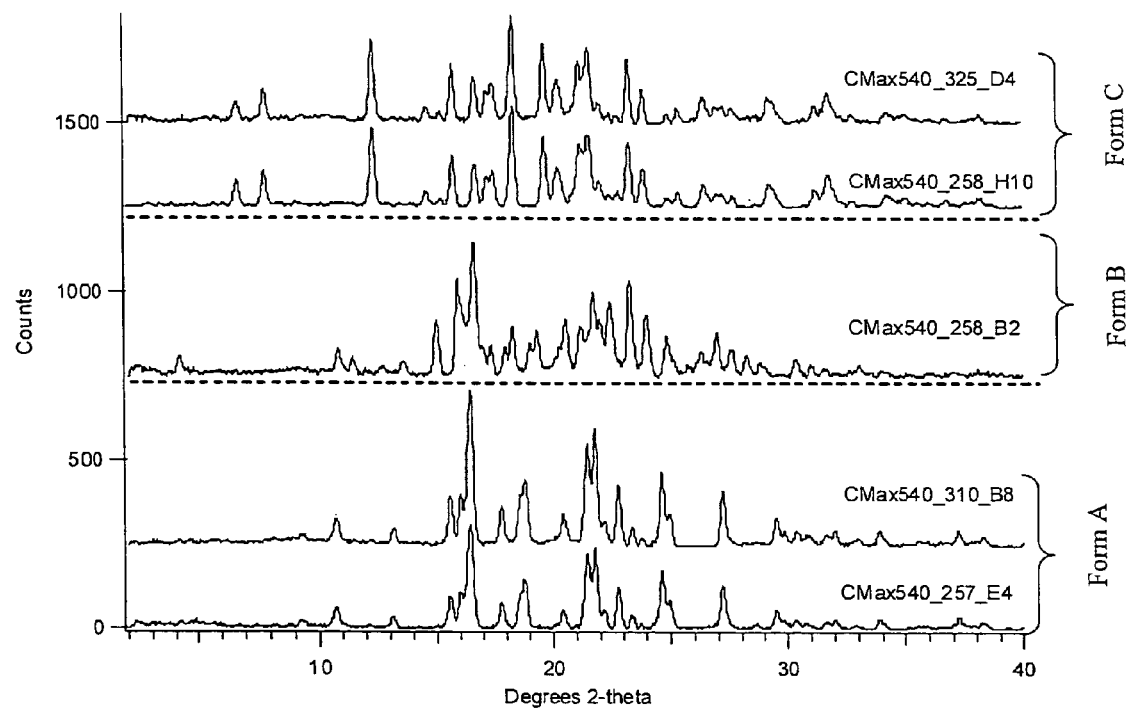
FIG. 7A—Compilation of PXRD data for sertraline mesylate salts
Figure 7B:
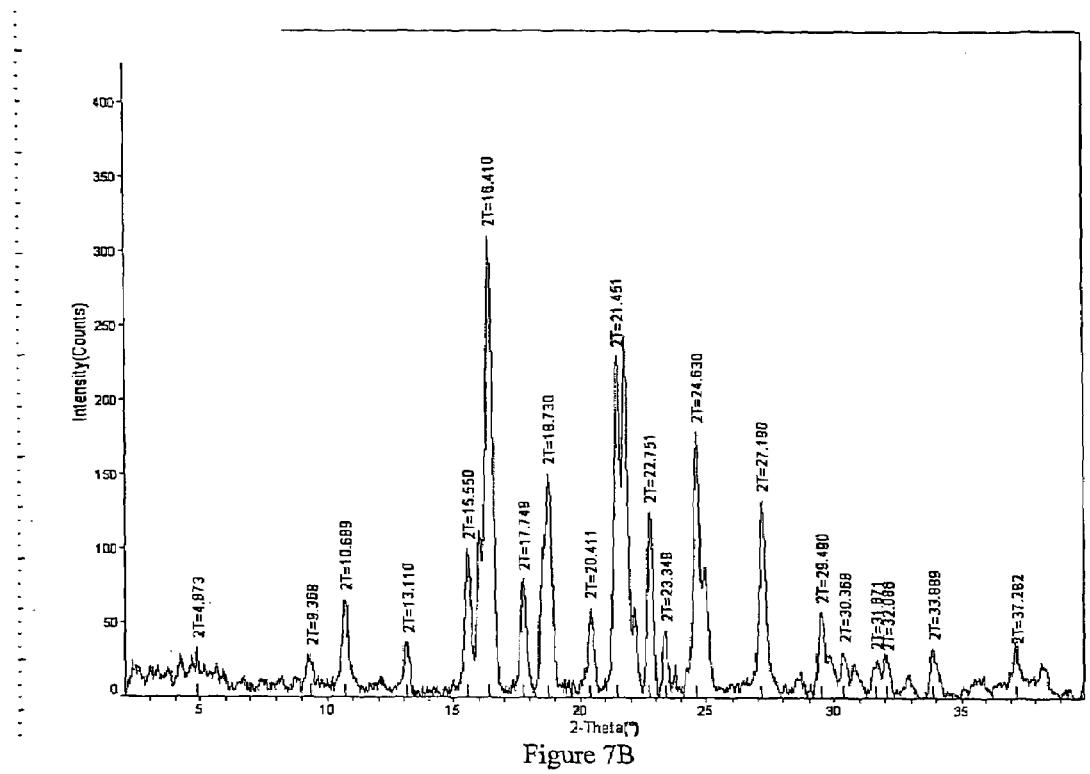
FIG. 7B—PXRD diffractogram of sertraline mesylate salt Form A
Figure 7C:
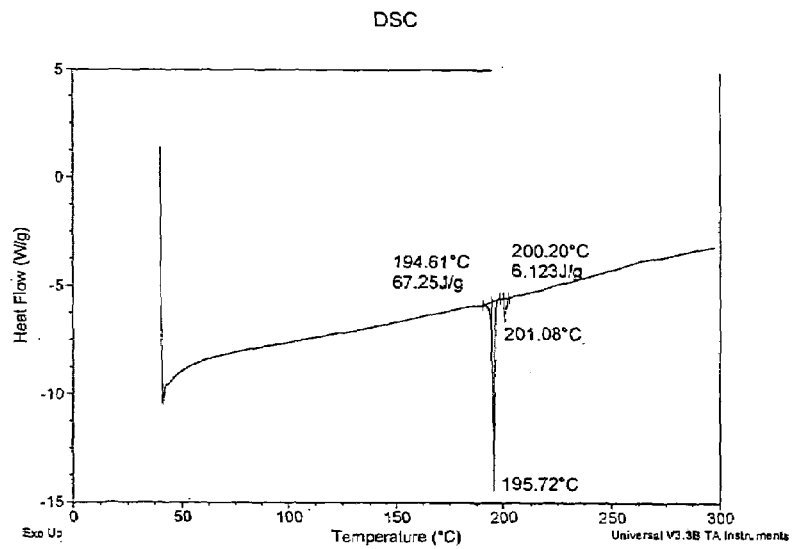
FIG. 7C—DSC thermogram of sertraline mesylate salt Form A
Figure 7D:
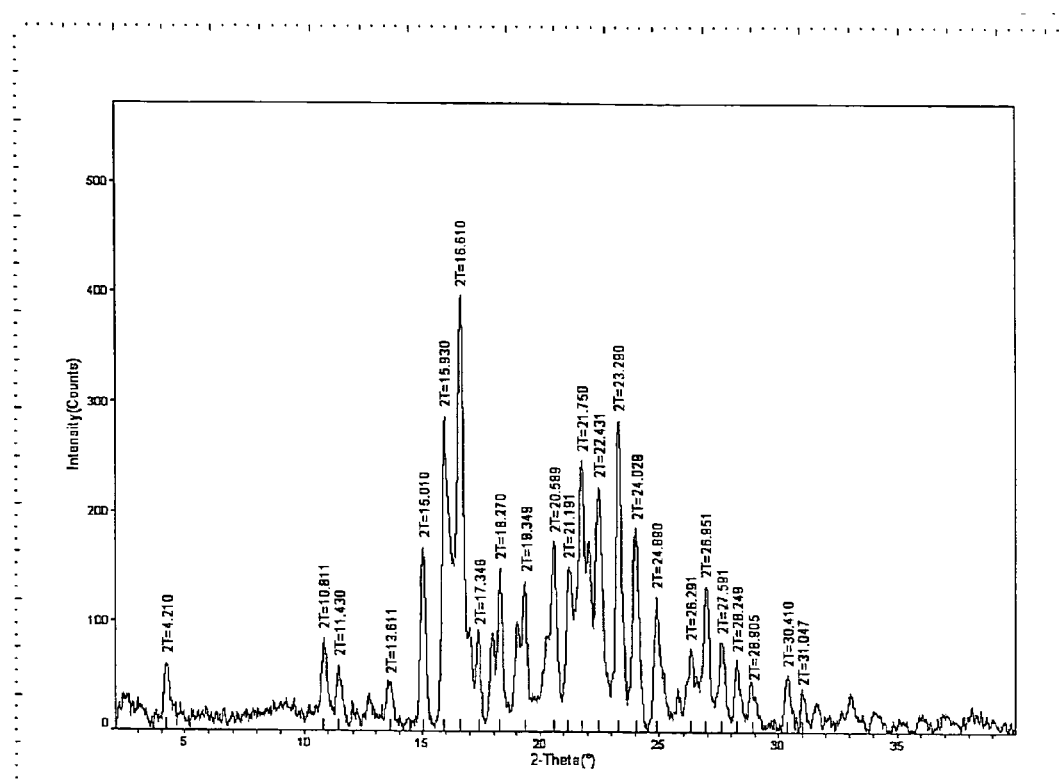
FIG. 7D—PXRD diffractogram of sertraline mesylate salt Form B
Figure 7E:
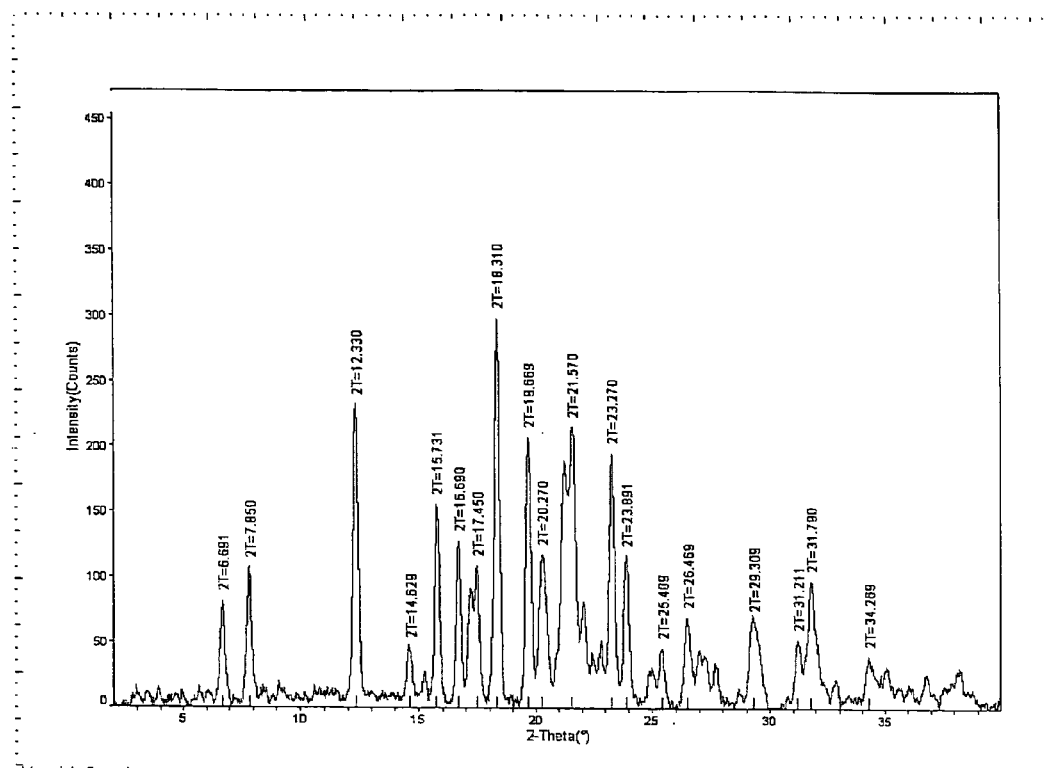
FIG. 7E—PXRD diffractogram of sertraline mesylate salt Form C
Figure 7F:
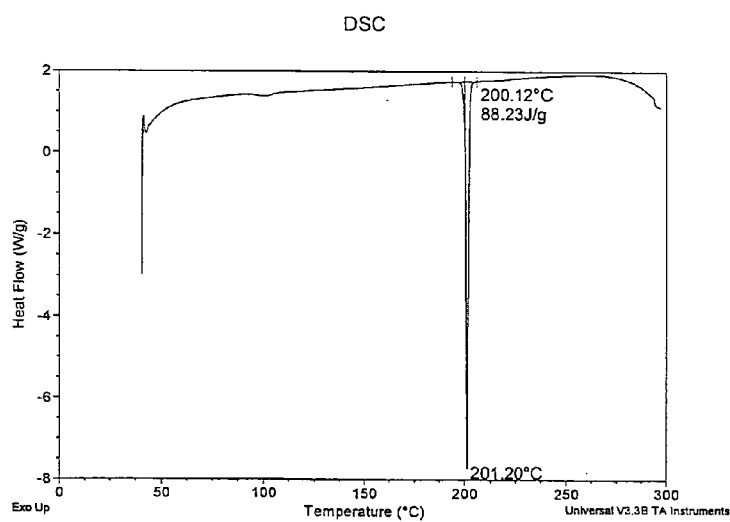
FIG. 7F—DSC thermogram of sertraline mesylate salt Form C

Three polymorphs were observed for sertraline mesylate salt. Sertraline mesylate Form A can be characterized by PXRD peaks at 10.7, 16.4, 18.7, 21.5, 24.6, and 27.2 degrees 2-theta. DSC of the sertraline mesylate Form A showed an endotherm at about 196 degrees C. (See FIG. 7C). A small endotherm at about 201 degrees C. in the DSC trace of sample 540_257_E4 indicates the presence of a small amount of form C. Form B can be characterized by PXRD peaks at 11.4, 15.0, 15.9, 16.6, 18.3, 19.3, 20.6, 23.3, and 24.9 degrees 2-theta. Form C (Solubility=4.2 mg/mL) can be characterized by PXRD peaks at 6.7, 7.9, 12.3, 15.7, 18.1, 19.7, 21.6, 23.3, and 31.8 degrees 2-theta. DSC of the sertraline mesylate Form C showed an endotherm at about 201 degrees C. (See FIG. 7F). Sertraline mesylate Form A can be characterized by any one, any two, any three, any four, any five, or any six or more of the peaks in the PXRD diffractogram in FIG. 7B including, but not limited to, 10.69, 16.41, 17.75, 18.73, 21.45, 22.75, 24.63, and 27.19 degrees 2-theta. Sertraline mesylate Form B can be characterized by any one, any two, any three, any four, any five, or any six or more of the peaks in the PXRD diffractogram in FIG. 7D including, but not limited to, 15.01, 15.93, 16.61, 18.27, 19.35, 20.59, 21.19, 21.75, 22.43, 23.29, 24.03, 24.89, and 26.95 degrees 2-theta. Sertraline mesylate Form C can be characterized by any one, any two, any three, any four, any five, or any six or more of the peaks in the PXRD diffractogram in FIG. 7E including, but not limited to, 6.69, 7.85, 12.33, 15.73, 16.69, 17.45, 18.31, 19.67, 20.27, 21.57, 23.27, 23.89, and 31.79 degrees 2-theta.

Crystallization of sertraline mesylate was completed from several solvent systems. All binary solvent systems were prepared in a 34:14 volume ratio. Sample 540_257_E4 (Form A) was crystallized from isopropyl acetate. Sample 540_310_B8 (Form A) was crystallized from a tetrahydrofuran:2-propanol mixture. Sample 540_258_B2 (Form B) was crystallized from a propylene glycol:water mixture. Sample 540_258_H10 (Form C) was crystallized from a 2-propanol:acetonitrile mixture. Sample 540_325_D4 (Form C) was crystallized from an n-heptane:ethanol mixture.

Sertraline Fumarate Salt

Several polymorphs of sertraline fumarate salt have been discovered. Forms A–F each yield distictive PXRD peaks. Several of these polymorphs also exhibit distinctive thermal behavior in DSC analysis. Form A can be characterized by peaks at 6.45, 8.85, 15.15, 16.04, 19.59, and 22.33 degrees 2-theta. Form B can be characterized by peaks at 12.34, 13.61, 14.38, 16.26, 17.52, and 24.26 degrees 2-theta. Form C can be characterized by peaks at 7.89, 10.81, 14.81, 15.59, 18.61, and 21.41 degrees 2-theta. Form D can be characterized by peaks at 13.85, 15.47, 16.15, 16.95, 19.19, and 22.17 degrees 2-theta. Form E can be characterized by peaks at 12.21, 12.47, 13.53, 13.87, 14.38, 16.26, 17.52, and 24.26 degrees 2-theta. Form F can be characterized by peaks at 6.95, 9.54, 11.36, 12.07, 12.9, 14.37, 17.10, and 24.14 degrees 2-theta. Forms C, E, and F may be alcohol solvates or desolvates.

Figure 8A:
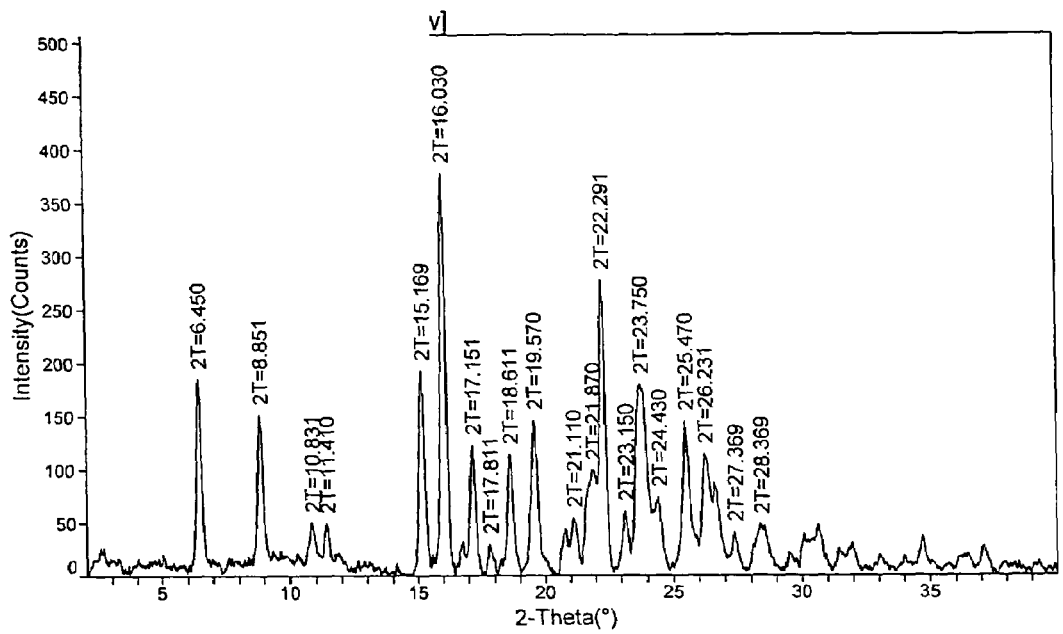
FIG. 8A—PXRD diffractogram of sertraline fumarate salt Form A
Figure 8B:
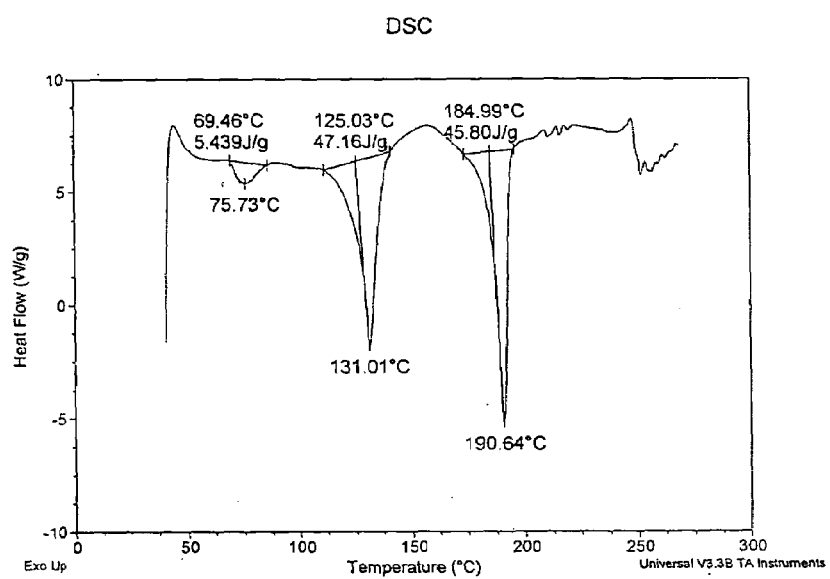
FIG. 8B—DSC thermogram of sertraline fumarate salt Form A
Figure 8C:
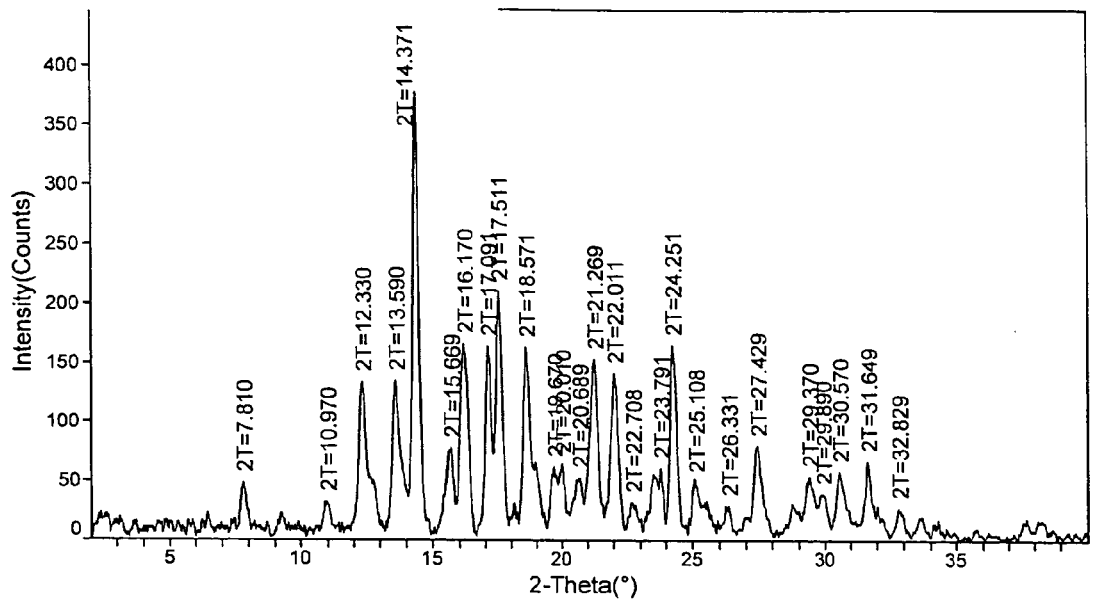
FIG. 8C—PXRD diffractogram of sertraline fumarate salt Form B FIG. 8D—DSC thermogram of sertraline fumarate salt Form B FIG. 8E—PXRD diffractogram of sertraline fumarate salt Form C FIG. 8F—PXRD diffractogram of sertraline fumarate salt Form D FIG. 8G—DSC thermogram of sertraline fumarate salt Form D FIG. 8H—PXRD diffractogram of sertraline fumarate salt Form E FIG. 8I—PXRD diffractogram of sertraline fumarate salt Form F FIG. 9A—PXRD diffractogram of sertraline citrate salt Form A FIG. 9B—DSC thermogram of sertraline citrate salt Form A FIG. 9C—PXRD diffractogram of sertraline citrate salt Form B FIG. 9D—PXRD diffractogram of sertraline citrate salt Form C FIG. 9E—PXRD diffractogram of sertraline citrate salt Form D FIG. 9F—DSC thermogram of sertraline citrate salt Form A FIG. 10A—PXRD diffractogram of sertraline sulfate salt Form A FIG. 10B—PXRD diffractogram of sertraline sulfate salt Form B FIG. 10C—PXRD diffractogram of sertraline sulfate salt Form C FIG. 11A—PXRD diffractogram of sertraline phosphate salt Form A FIG. 11B—DSC thermogram of sertraline phosphate salt Form A FIG. 11C—PXRD diffractogram of sertraline phosphate salt Form B FIG. 11D—PXRD diffractogram of sertraline phosphate salt Form C FIG. 11E—DSC thermogram of sertraline phosphate salt Form C FIG. 12A—PXRD diffractogram of sertraline succinate salt Form A FIG. 12B—DSC thermogram of sertraline succinate salt Form A FIG. 12C—PXRD diffractogram of sertraline succinate salt Form B FIG. 12D—PXRD diffractogram of sertraline succinate salt Form C FIG. 13A—PXRD diffractogram of sertraline malonate salt Form A FIG. 13B—DSC thermogram of sertraline malonate salt Form A FIG. 13C—PXRD diffractogram of sertraline malonate salt Form A FIG. 13D—DSC thermogram of sertraline malonate salt Form A FIG. 13E—PXRD diffractogram of sertraline malonate salt Form B FIG. 13F—PXRD diffractogram of sertraline malonate salt Form C FIG. 14A—PXRD diffractogram of sertraline L-tartrate salt Form A FIG. 14B—DSC thermogram of sertraline L-tartrate salt Form A FIG. 14C—PXRD diffractogram of sertraline L-tartrate salt Form B FIG. 14D—DSC thermogram of sertraline L-tartrate salt Form B FIG. 15A—PXRD diffractogram of sertraline maleate salt Form A FIG. 15B—DSC thermogram of sertraline maleate salt Form A FIG. 15C—PXRD diffractogram of sertraline maleate salt Form B FIG. 15D—PXRD diffractogram of sertraline maleate salt Form C FIG. 15E—PXRD diffractogram of sertraline maleate salt Form D FIG. 16A—TGA thermogram of sertraline HCl acetic acid solvate FIG. 16B—PXRD diffractogram of sertraline HCl acetic acid solvate FIG. 16C—DSC thermogram of sertraline HCl acetic acid solvate FIG. 16D—Raman spectrum of sertraline HCl acetic acid solvate FIG. 17A—TGA thermogram of sertraline HCl ethyl acetate hemisolvate FIG. 17B—PXRD diffractogram of sertraline HCl ethyl acetate hemisolvate FIG. 17C—DSC thermogram of sertraline HCl ethyl acetate hemisolvate
Figure 8D:
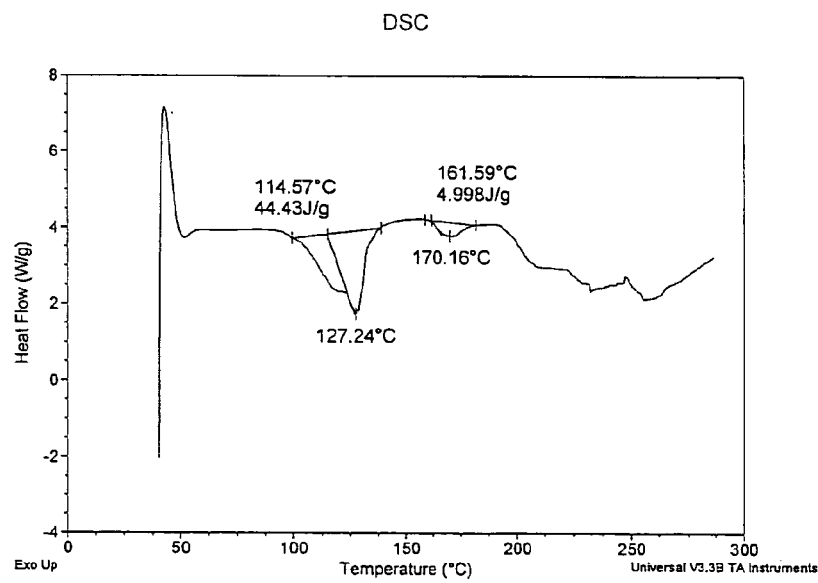
Figure 8E:
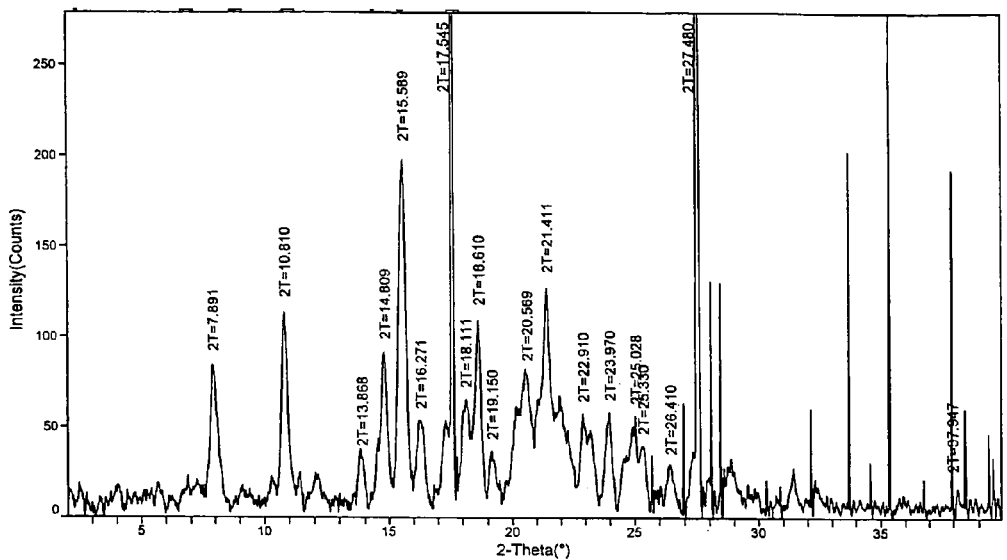
Figure 8F:
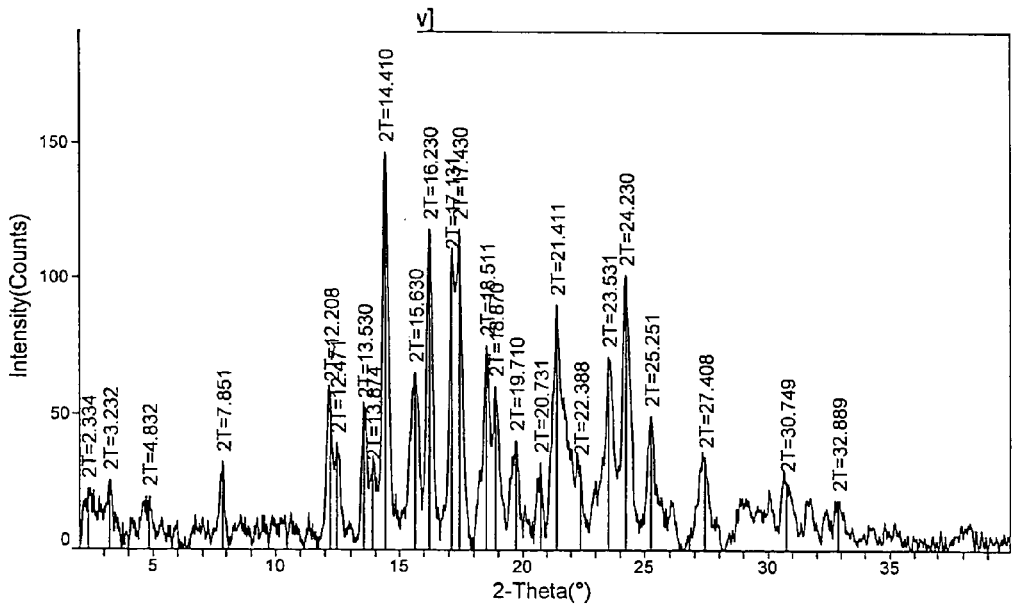
Figure 8G:
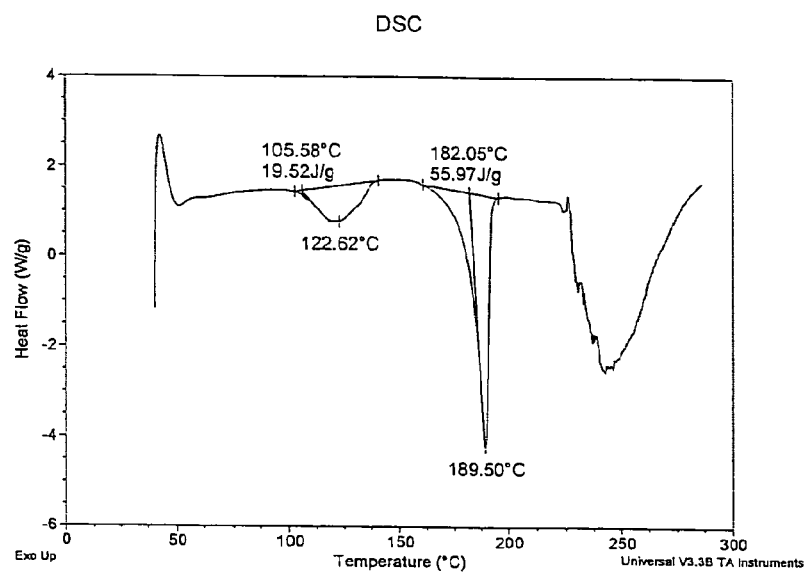
Figure 8H:
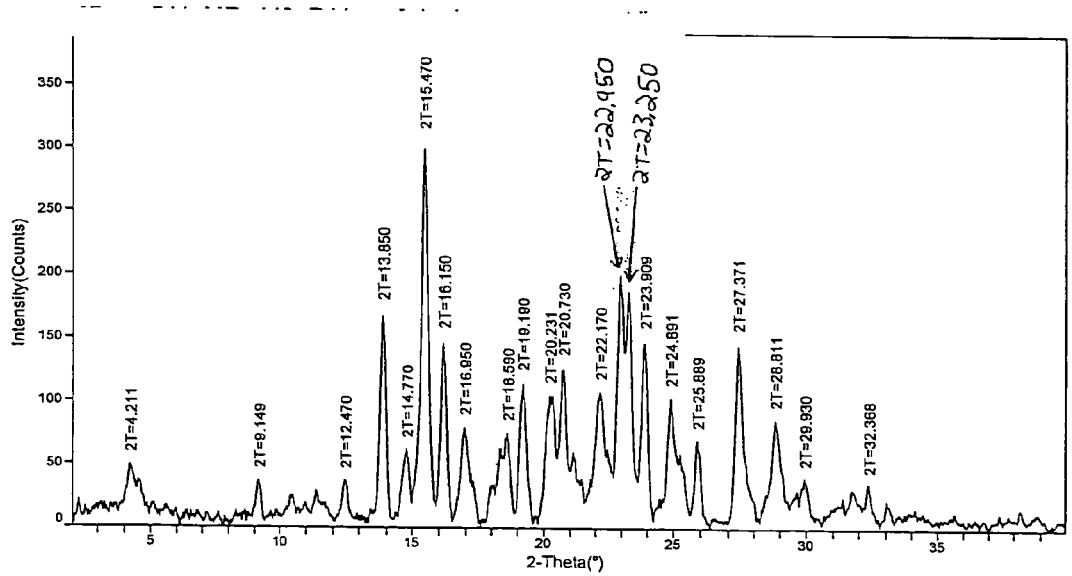
Figure 8I:
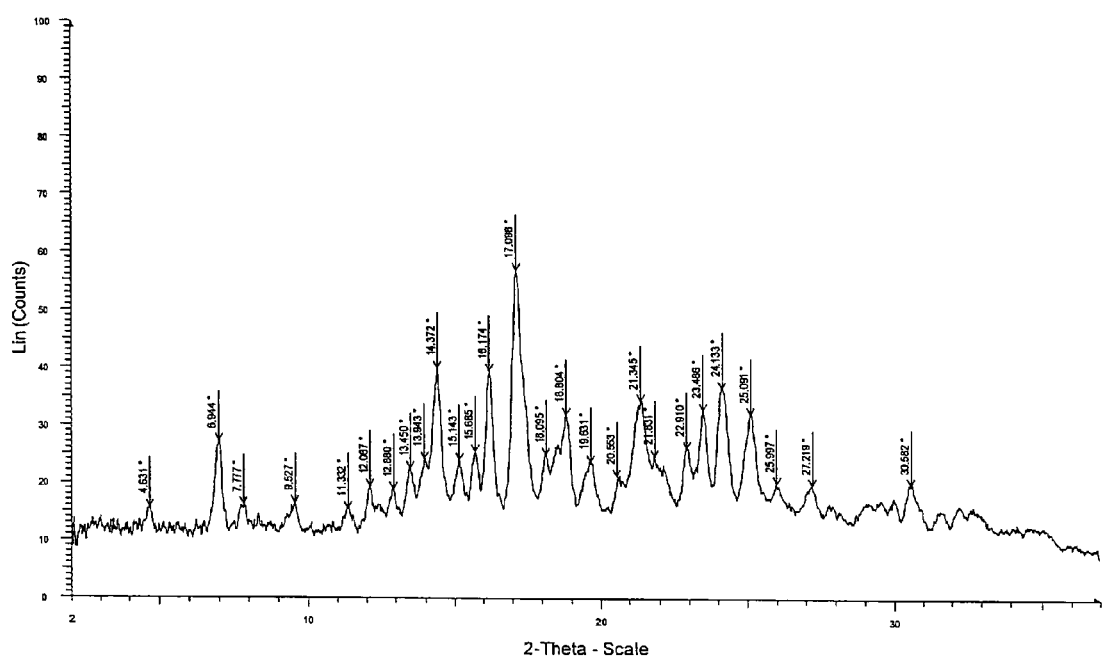

Sertraline fumarate Form A can be characterized by any one, any two, any three, any four, any five, or any six or more of the peaks in the PXRD diffractogram in FIG. 8A including, but not limited to, 6.45, 8.85, 15.17, 16.03, 17.15, 18.61, 19.57, 22.29, 23.75, 25.47, and 26.23 degrees 2-theta. Sertraline fumarate Form B can be characterized by any one, any two, any three, any four, any five, or any six or more of the peaks in the PXRD diffractogram in FIG. 8C including, but not limited to, 12.33, 13.59, 14.37, 16.17, 17.09, 17.51, 18.57, 21.27, 22.01, 24.25, and 27.43 degrees 2-theta. Sertraline fumarate Form C can be characterized by any one, any two, any three, any four, any five, or any six or more of the peaks in the PXRD diffractogram in FIG. 8E including, but not limited to, 7.89, 10.81, 14.81, 15.5917.55, 18.61, 20.57, 21.41, and 27.48 degrees 2-theta. Sertraline fumarate Form D can be characterized by any one, any two, any three, any four, any five, or any six or more of the peaks in the PXRD diffractogram in FIG. 8F including, but not limited to, 12.21, 14.41, 15.63, 16.23, 17.43, 18.51, 21.41, 23.53, 24.23, and 25.25 degrees 2-theta. Sertraline fumarate Form E can be characterized by any one, any two, any three, any four, any five, or any six or more of the peaks in the PXRD diffractogram in FIG. 8H including, but not limited to, 13.85, 15.47, 16.15, 19.19, 20.23, 20.73, 22.17, 22.95, 23.91, 24.89, and 27.37 degrees 2-theta. Sertraline fumarate Form F can be characterized by any one, any two, any three, any four, any five, or any six or more of the peaks in the PXRD diffractogram in FIG. 8I including, but not limited to, 6.94, 12.07, 13.45, 14.37, 16.17, 17.10, 18.80, 19.63, 21.35, 23.49, 24.13, and 25.09 degrees 2-theta.

DSC analysis of the sertraline fumarate polymorphs was also completed. The DSC thermogram of form A shows several endothermic transitions at about 76 degrees C., about 131 degrees C., and about 191 degrees C. Form B shows two endotherms, one at about 127 degrees C. and another at about 170 degrees C. Form D shows two endotherms, one at about 123 degrees C., and another at about 190 degrees C.

Sertraline fumarate Form A was crystallized from mixed solvents of tetrahydrofuran:acetonitrile, tetrahydrofuran:isopropyl acetate, tetrahydrofuran:acetonitrile, and 1:1 tetrahydrofuran:n-heptane. Sertraline fumarate Form B was crystallized from 2-propanol:ethanol and n-heptane:2-propanol. Sertraline fumarate Form C was crystallized from 2-propanol:iso-butanol. Sertraline fumarate Form D was crystallized from tetrahydrofuran:n-heptane. Sertraline fumarate Form E was crystallized from ethanol:isopropyl acetate. Sertraline fumarate Form F was crystallized from tetrahydrofuran:acetonitrile and tetrahydrofuran:isopropyl acetate.

Sertraline Citrate Salt

Several polymorphs of sertraline citrate salt have been discovered. Forms A–D each yield distinctive PXRD diffractograms. Form A can be characterized by PXRD peaks at 4.83, 15.15, 15.70, 16.31, and 17.70 degrees 2-theta. Form B can be characterized by PXRD peaks at 4.07, 10.69, 15.63, 16.89, 19.63, and 24.29 degrees 2-theta. Form C can be characterized by PXRD peaks at 2.4, 14.6, 16.0, 22.2, and 24.9 degrees 2-theta. Form D is an amorphous structure.

Figure 9A:
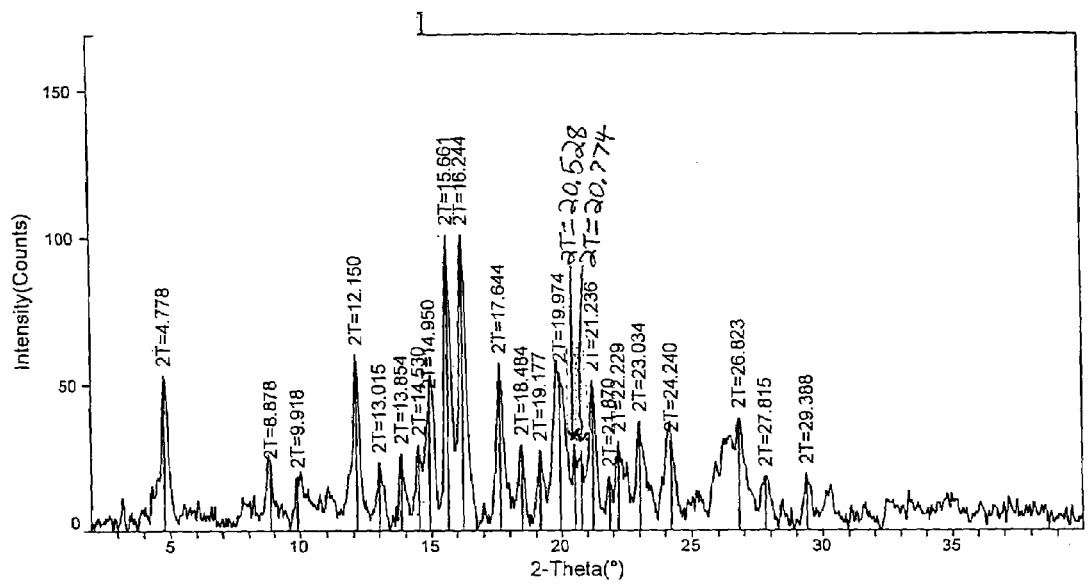
Figure 9B:
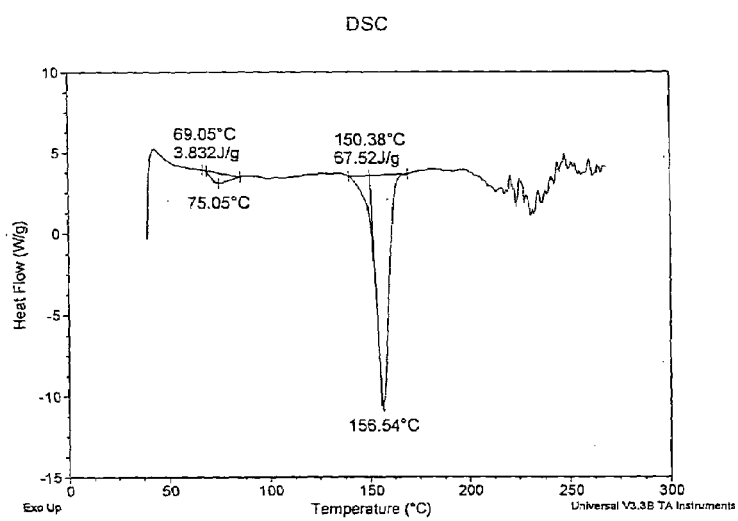
Figure 9C:
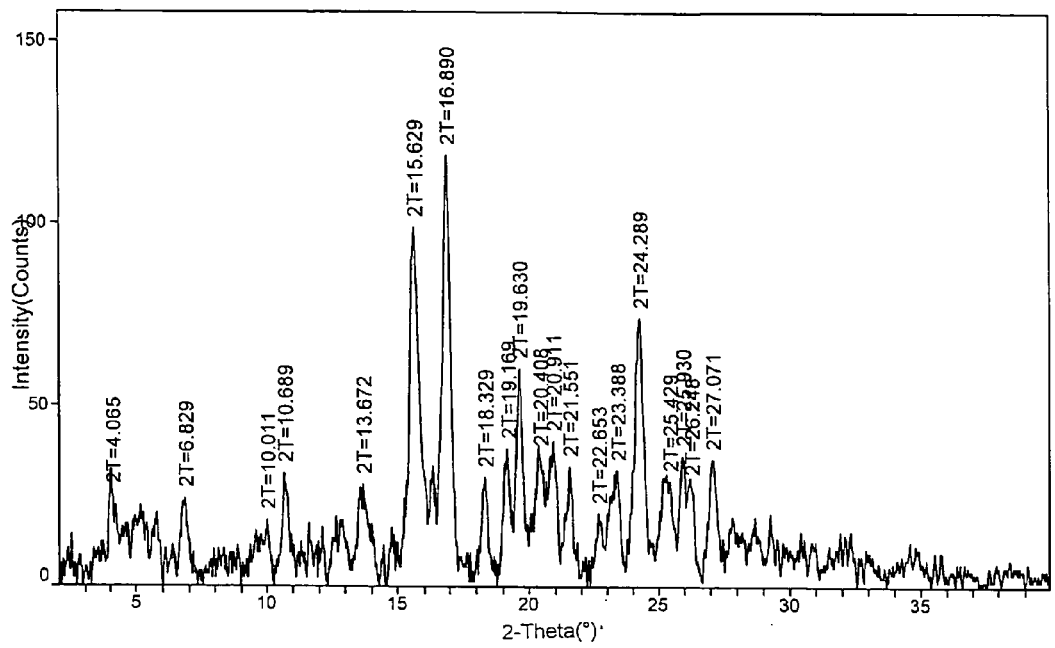
Figure 9D:
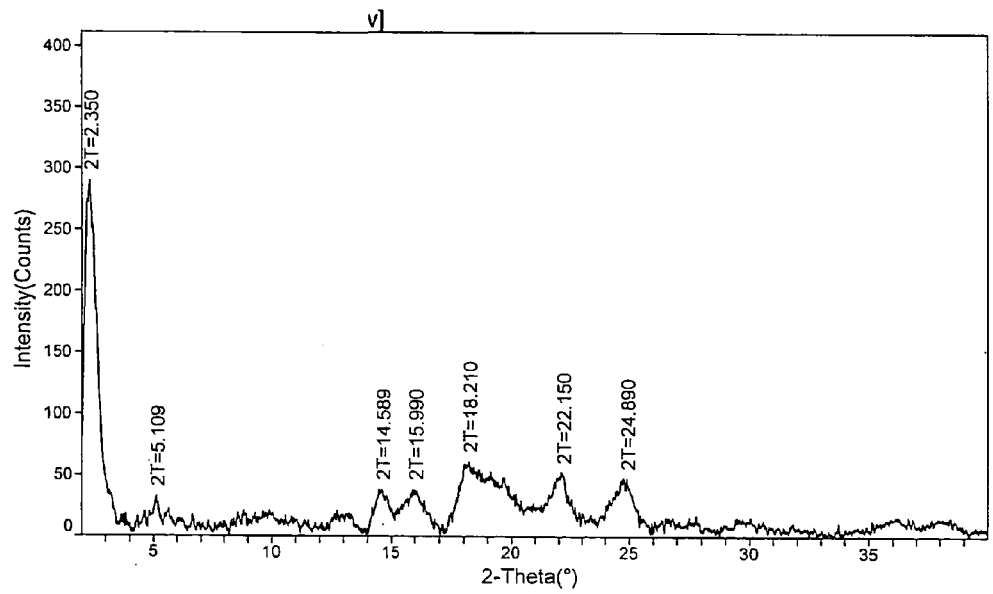
Figure 9E:
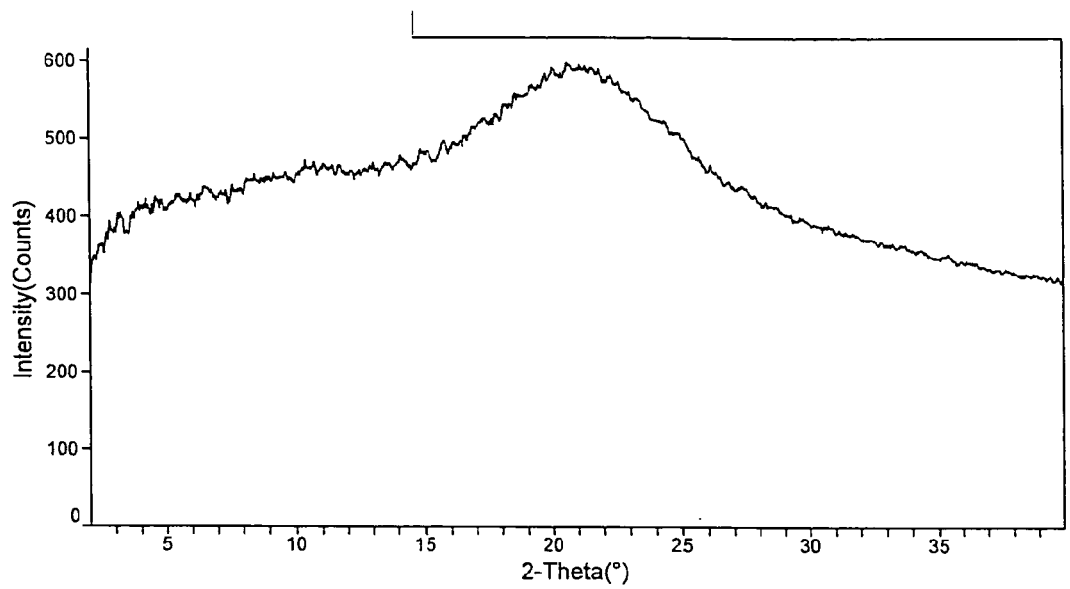

Sertraline citrate Form A can be characterized by any one, any two, any three, any four, any five, or any six or more of the peaks in the PXRD diffractogram in FIG. 9A including, but not limited to, 4.78, 12.15, 14.95, 15.66, 16.24, 17.64, 19.97, 21.24, 23.03, 24.24, and 26.82 degrees 2-theta. Sertraline citrate Form B can be characterized by any one, any two, any three, any four, any five, or any six or more of the peaks in the PXRD diffractogram in FIG. 9C including, but not limited to, 6.83, 10.69, 13.67, 15.63, 16.89, 18.33, 19.17, 19.63, 20.41, 20.91, 21.55, 23.39, 24.29, and 27.07 degrees 2-theta. Sertraline citrate Form C can be characterized by any one, any two, any three, any four, any five, or any six or more of the peaks in the PXRD diffractogram in FIG. 9D including, but not limited to, 2.35, 5.11, 14.59, 15.99, 18.21, 22.15, and 24.89 degrees 2-theta. Amorphous sertraline citrate (Form D) was observed and the PXRD diffractogram is shown in FIG. 9E.

Figure 9F:
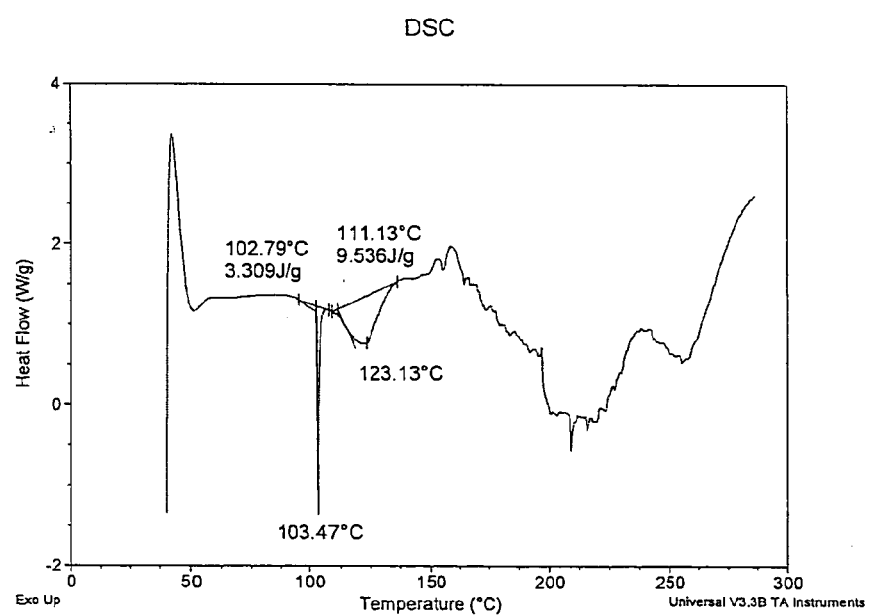

DSC analysis of the sertraline citrate polymorphs was also completed. The DSC thermogram of a sample of form A shows two endothermic transitions, one at about 75 degrees C., and another at about 157 degrees C. (See FIG. 9B). However, another sample of form A shows two endothermic transitions, one at about 103 degrees C., and another at about 123 degrees C. (See FIG. 9F). This suggests that there may be residual solvent altering the DSC data for one or both of these samples.

Sertraline citrate form A was crystallized from ethanol, acetonitrile:propanol, ethanol:tetrahydrofuran, ethanol:isopropyl acetate, ethanol:acetonitrile, and acetonitrile:tetrahydrofuran. Sertraline citrate form B was crystallized from water. Sertraline citrate form C was crystallized from 13:32 n-heptane:tetrahydrofuran. Amorphous sertraline citrate (form D)was crystallized from 15:36 iso-butanol:water.

Sertraline Sulfate Salt

Several polymorphs of sertraline sulfate salt have been discovered. Forms A-C each yield distinctive PXRD diffractograms. Form A can be characterized by PXRD peaks at 11.67, 14.74, 16.17, 16.75, 17.29, and 18.57 degrees 2-theta. Form B can be characterized by PXRD peaks at 10.8, 13.81, 17.69, 19.42, 20.67, 26.97, and 28.23 degrees 2-theta. Form C can be characterized by PXRD peaks at 11.23, 16.25, 17.47, 23.55, and 25.30 degrees 2-theta. Form B has many peaks in common with form A, and may contain some form A as an impurity.

Figure 10A:
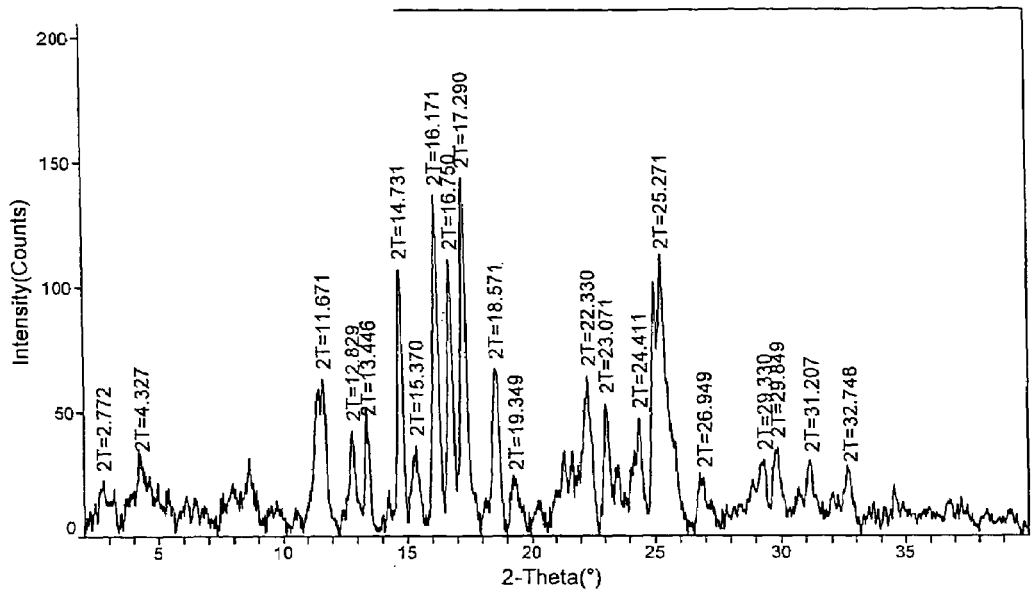
Figure 10B:
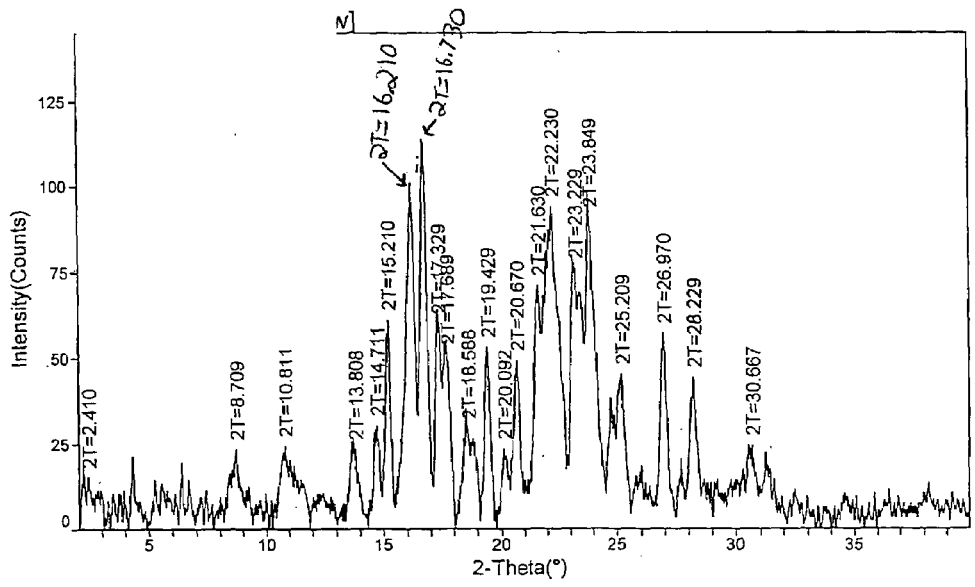
Figure 10C:
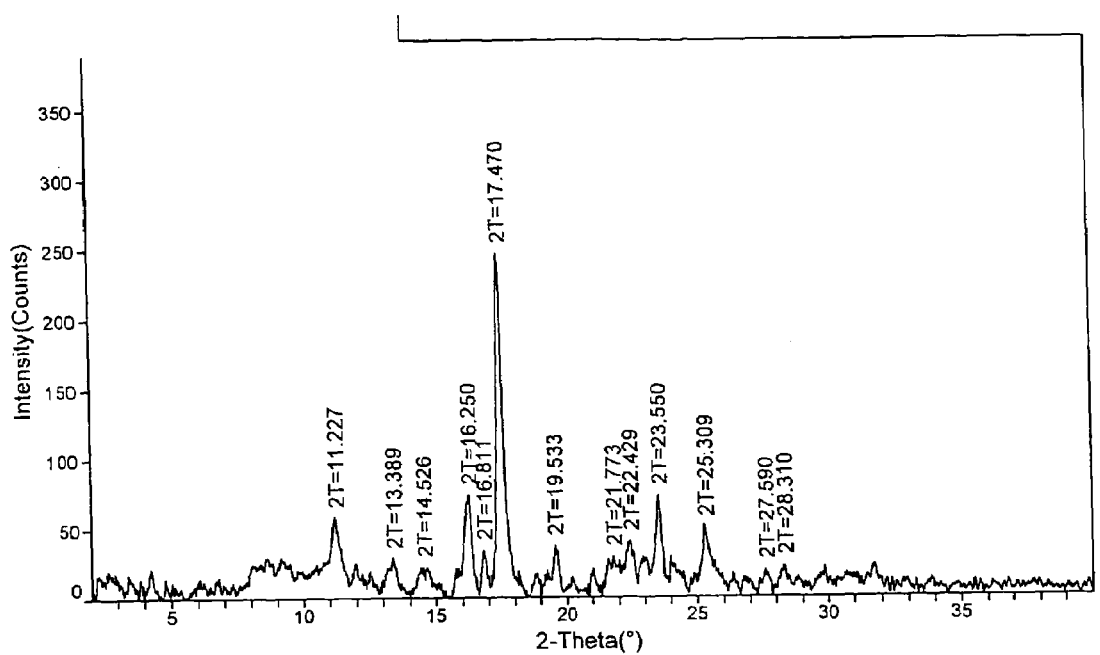

Sertraline sulfate Form A can be characterized by any one, any two, any three, any four, any five, or any six or more of the peaks in the PXRD diffractogram in FIG. 10A including, but not limited to, 11.67, 12.83, 13.45, 14.73, 16.17, 16.75, 17.29, 18.57, 22.33, 23.07, and 25.27 degrees 2-theta. Sertraline sulfate Form B can be characterized by any one, any two, any three, any four, any five, or any six or more of the peaks in the PXRD diffractogram in FIG. 10B including, but not limited to, 8.71, 10.81, 15.21, 16.21, 16.73, 17.33, 19.43, 20.67, 21.63, 22.23, 23.23, 23.85, 25.21, 26.97, and 28.23 degrees 2-theta. Sertraline sulfate Form C can be characterized by any one, any two, any three, any four, any five, or any six or more of the peaks in the PXRD diffractogram in FIG. 10C including, but not limited to, 11.23, 13.39, 14.53, 16.25, 17.47, 19.53, 22.43, 23.55, and 25.31 degrees 2-theta.

Sertraline sulfate form A was crystallized from 36:15 water:acetonitrile. Sertraline sulfate form B was crystallized from acetonitrile. Sertraline sulfate form C was crystallized from 13:32 propylene glycol:water.

Sertraline Phosphate Salt

Several polymorphs of sertraline sulfate salt have been discovered. Forms A–C each yield distinctive PXRD diffractograms. Form A can be characterized by PXRD peaks at 9.25, 15.13, 15.69, 16.51, 17.63, 21.53, and 25.65 degrees 2-theta. Form B can be characterized by PXRD peaks at 8.85, 12.59, 15.91, 17.51, and 24.11 degrees 2-theta. Form C can be characterized by PXRD peaks at 4.85, 12.49, 15.15, 16.29, 22.23, and 23.91 degrees 2-theta.

Figure 11A:
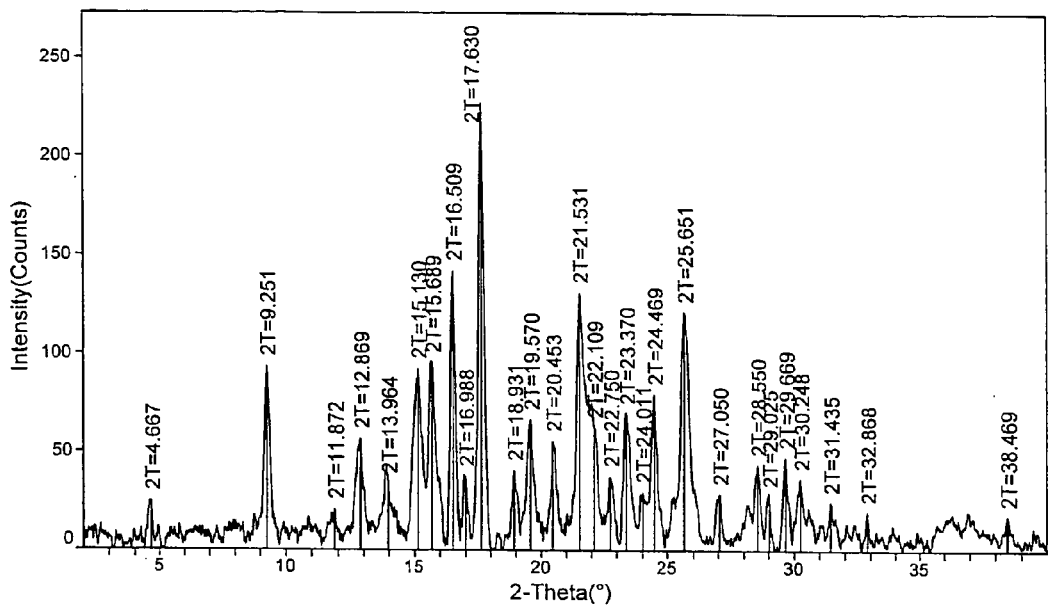
Figure 11B:
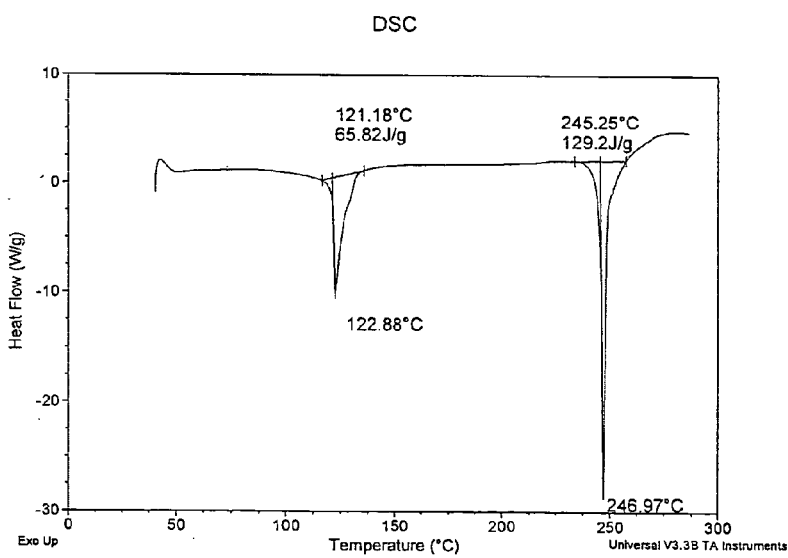
Figure 11C:
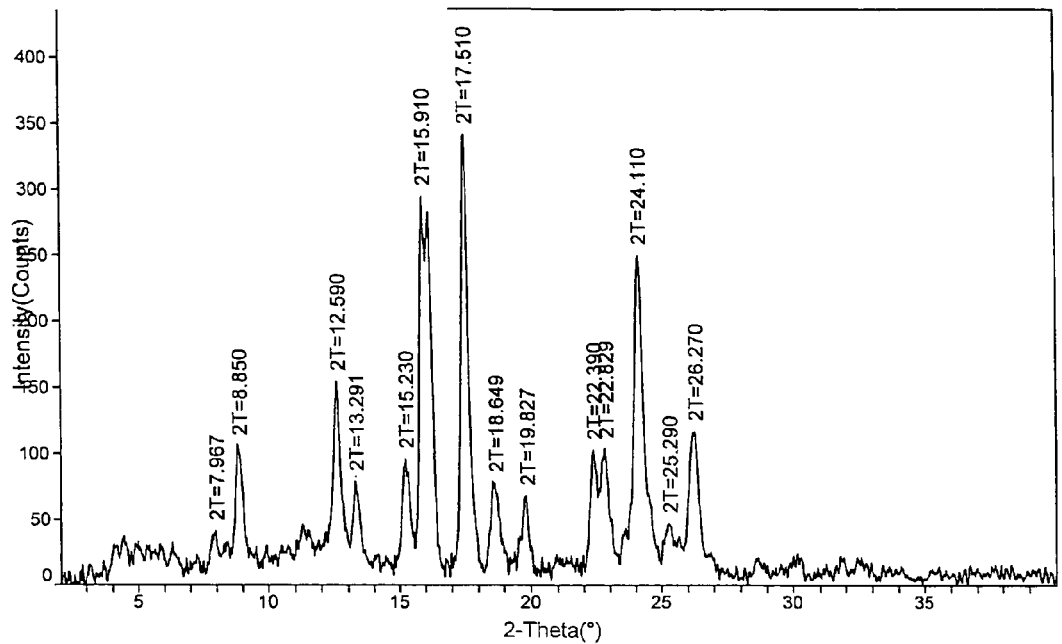
Figure 11D:
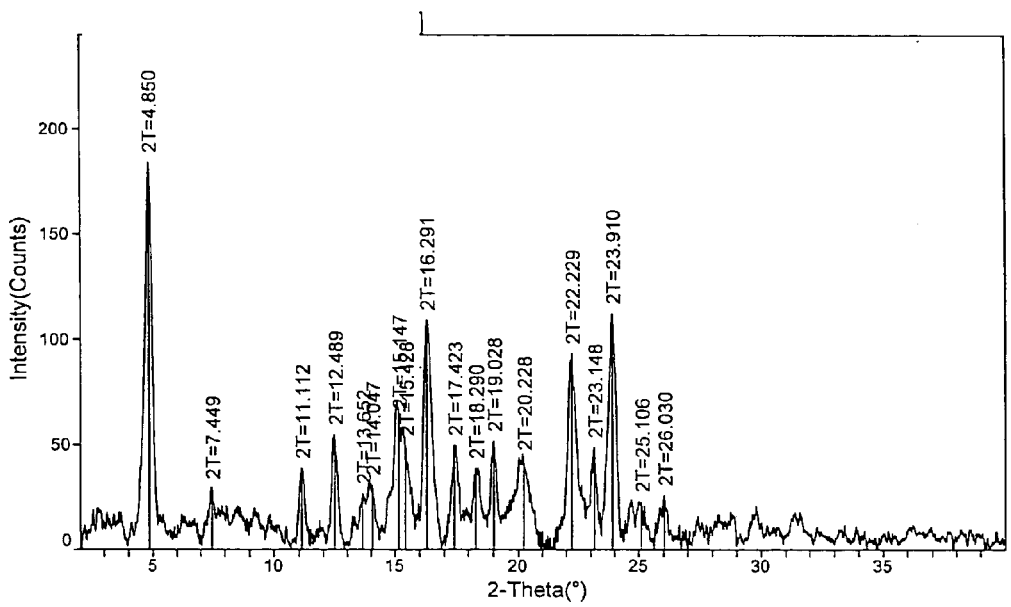

Sertraline phosphate Form A can be characterized by any one, any two, any three, any four, any five, or any six or more of the peaks in the PXRD diffractogram in FIG. 11A including, but not limited to, 9.25, 12.87, 15.13, 15.69, 16.51, 17.63, 19.57, 20.45, 21.53, 23.37, 24.47, 25.65, 28.55, and 29.67 degrees 2-theta. Sertraline phosphate Form B can be characterized by any one, any two, any three, any four, any five, or any six or more of the peaks in the PXRD diffractogram in FIG. 11C including, but not limited to, 8.85, 12.59, 15.91, 17.51, 18.65, 19.83, 22.39, 22.83, 24.11, and 26.27 degrees 2-theta. Sertraline phosphate Form C can be characterized by any one, any two, any three, any four, any five, or any six or more of the peaks in the PXRD diffractogram in FIG. 11D including, but not limited to, 4.85, 11.11, 12.49, 15.15, 16.29, 17.42, 18.29, 19.03, 20.23, 22.23, and 23.91 degrees 2-theta.

DSC analysis was performed on form A and form C. Form A showed two endothermic transitions, one at about 123 degrees C., and another at about 247 degrees C. (See FIG.

Figure 11E:
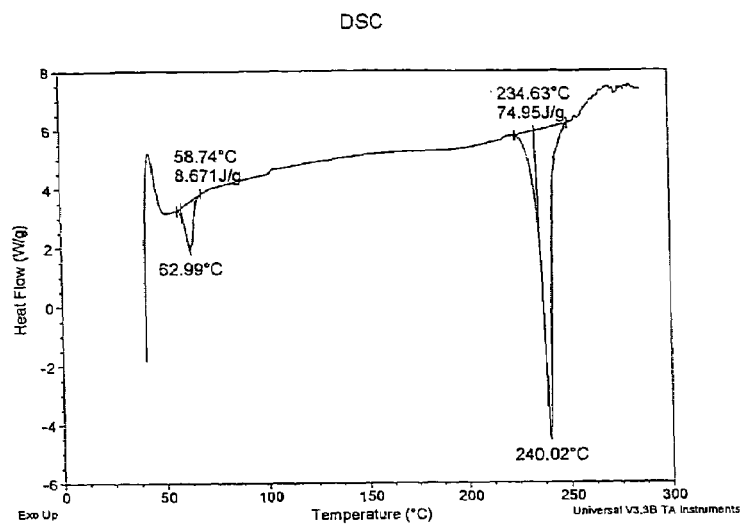

11B). Form C shows two endothermic transitions, one at about 63 degrees C., and another at about 240 degrees C. (See FIG. 11E).

Sertraline phosphate form A was crystallized from water:acetonitrile and ethanol:water. Sertraline phosphate form B was crystallized from 2-propanol:water. Sertraline phosphate form C was crystallized from acetonitrile:propylene glycol, isopropyl acetate:tetrahydrofuran, and 2-propanol:ethanol.

Sertraline Succinate Salt

Several polymorphs of sertraline succinate salt have been discovered. Forms A–C each yield distinctive PXRD diffractograms. Form A can be characterized by PXRD peaks at 3.75, 15.15, 17.51, 22.79, and 25.91 degrees 2-theta. Form B can be characterized by PXRD peaks at 7.23, 7.91, 10.77, 16.53, 17.47, 20.45, 20.91, 21.29, and 23.17 degrees 2-theta. Form C can be characterized by PXRD peaks at 4.43, 16.79, 22.25, and 24.61 degrees 2-theta.

Figure 12A:
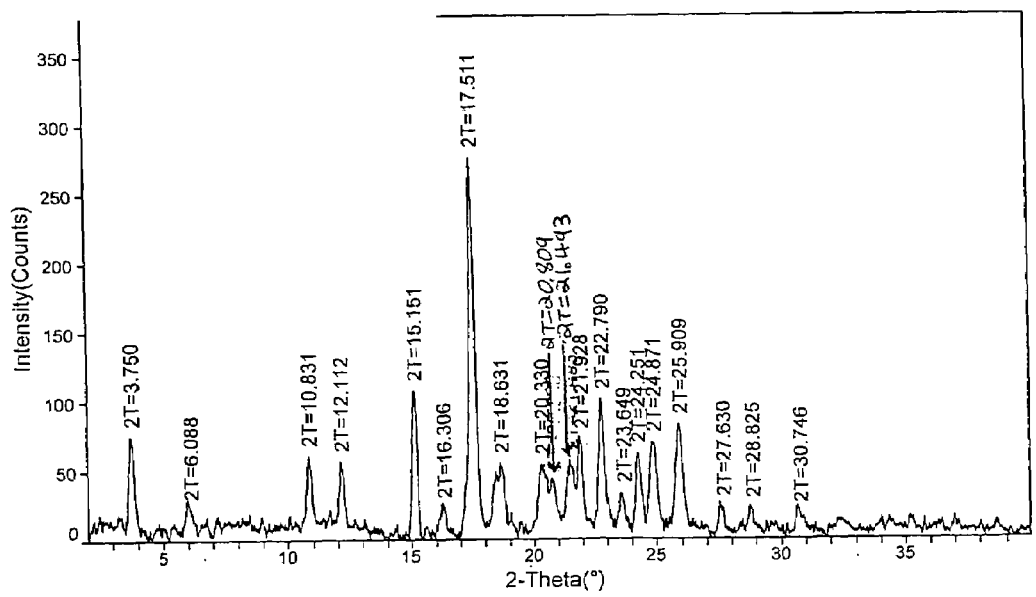
Figure 12B:
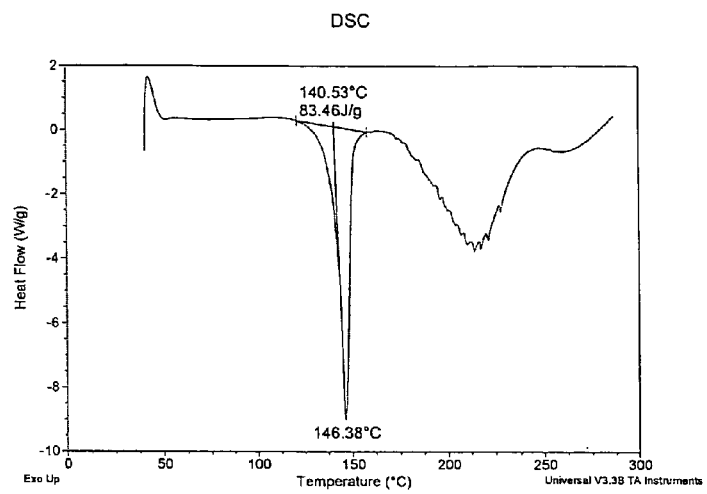
Figure 12C:
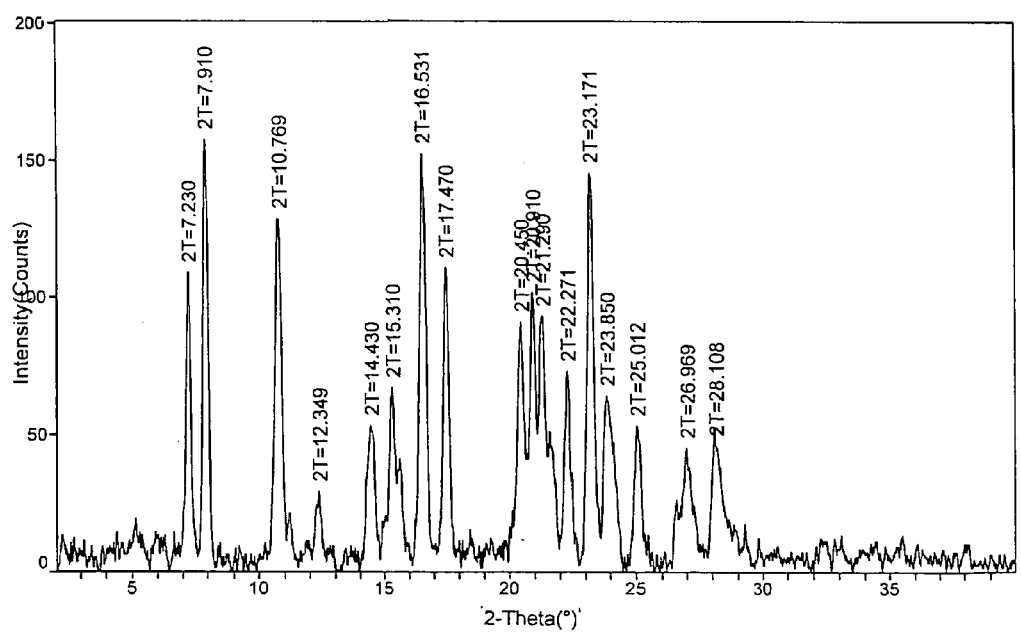
Figure 12D:
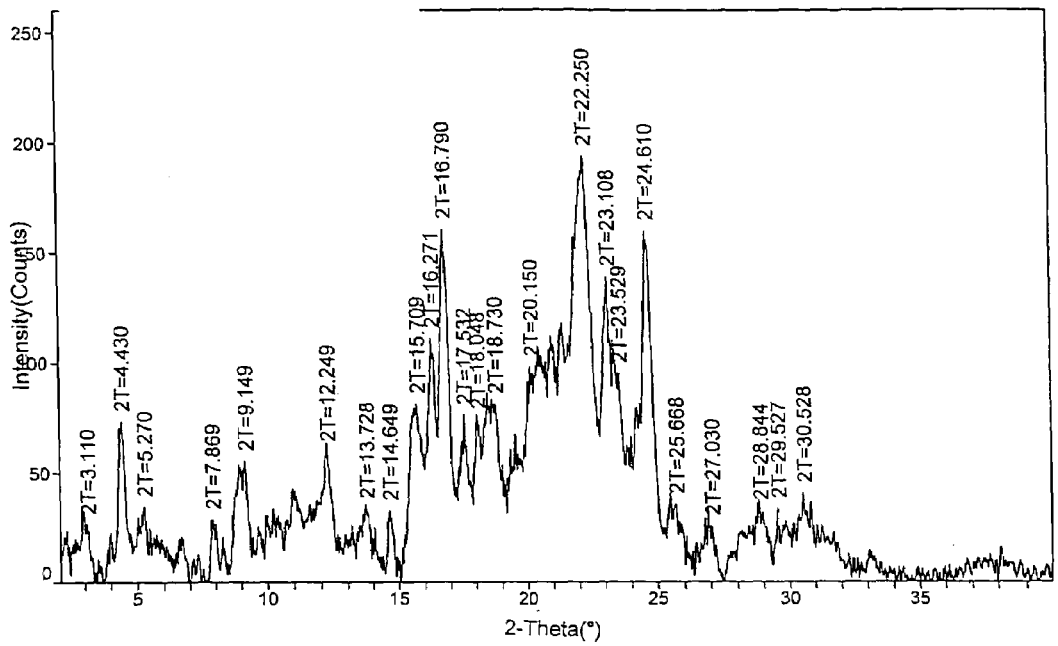

Sertraline succinate Form A can be characterized by any one, any two, any three, any four, any five, or any six or more of the peaks in the PXRD diffractogram in FIG. 12A including, but not limited to, 3.75, 10.83, 12.11, 15.15, 17.51, 18.63, 20.33, 21.93, 22.79, 24.25, 24.87, and 25.91 degrees 2-theta. Sertraline succinate Form B can be characterized by any one, any two, any three, any four, any five, or any six or more of the peaks in the PXRD diffractogram in FIG. 12C including, but not limited to, 7.23, 7.91, 10.77, 14.43, 15.31, 16.53, 17.47, 20.91, 22.27, 23.17, 23.85, 25.01, 26.97, and 28.11 degrees 2-theta. Sertraline succinate Form C can be characterized by any one, any two, any three, any four, any five, or any six or more of the peaks in the PXRD diffractogram in FIG. 12D including, but not limited to, 4.43, 9.15, 12.25, 15.71, 16.27, 16.79, 18.73, 20.15, 22.25, 23.11, and 24.61 degrees 2-theta.

DSC analysis completed on Form A showed an endothermic transition at about 146 degrees C. (See FIG. 12B).

Sertraline succinate Form A was crystallized in ethanol:isopropyl acetate, isopropyl acetate, acetonitrile:tetrahydrofuran, and 32:13 tetrahydrofuran:2-propanol. Sertraline succinate Form B was crystallized in iso-butanol:2-propanol. Sertraline succinate Form C was crystallized in tetrahydrofuran.

Sertraline Malonate Salt

Several polymorphic forms of sertraline malonate salt were found, forms A-C. Form A can be characterized by PXRD peaks at 6.97, 12.25, 14.17, 15.08, 17.25, and 18.75 degrees 2-theta. Form B can be characterized by peaks at 10.51, 12.46, and 20.60 degrees 2-theta. Form C can be characterized by peaks at 8.42, 10.51, 12.45, and 21.34 degrees 2-theta.

Figure 13A:
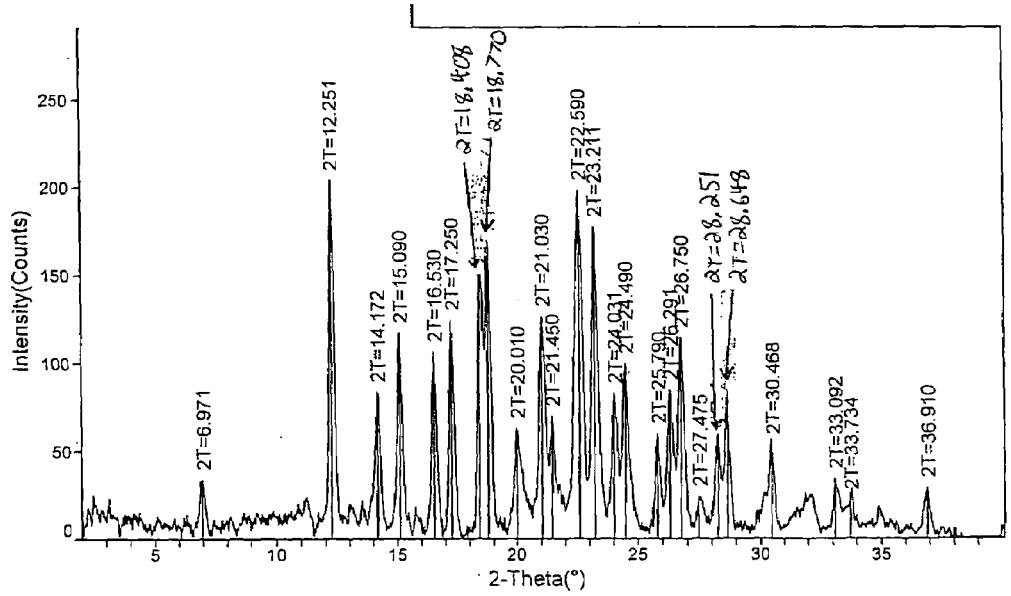
Figure 13B:
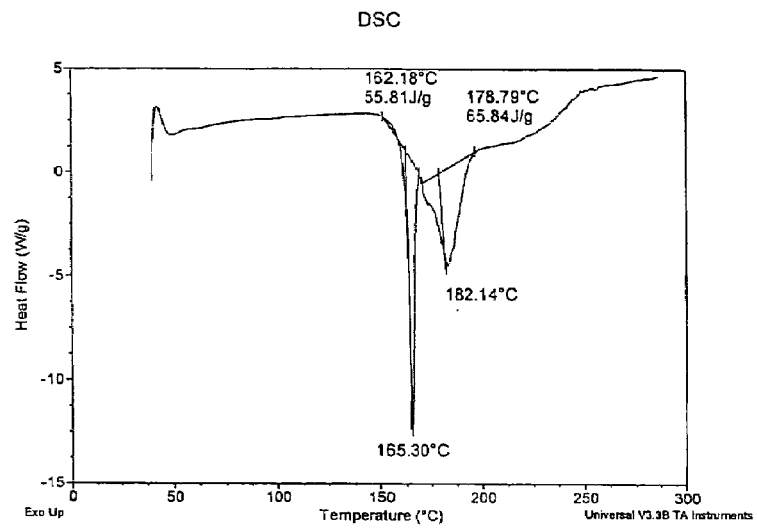
Figure 13C:
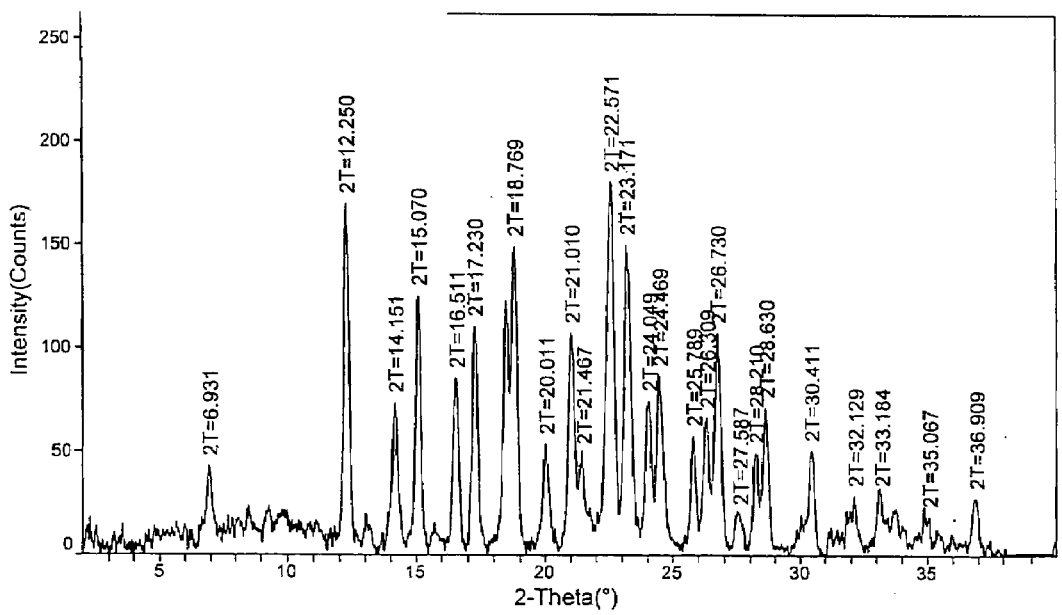

Sertraline malonate Form A can be characterized by any one, any two, any three, any four, any five, or any six or more of the peaks in the PXRD diffractogram in FIG. 13A or 13C including, but not limited to, 6.97, 12.25, 15.09, 16.53, 17.25, 18.41, 18.77, 21.03, 22.59, 23.21, 24.49, 26.75, 28.65, and 30.47 degrees 2-theta. Sertraline malonate Form B can be characterized by any one, any two, any three, any four, any five, or any six or more of the peaks in the PXRD diffractogram in FIG. 13E including, but not limited to, 6.91, 10.51, 12.46, 14.26, 16.89, 20.60, 25.08, and 26.69 degrees 2-theta. Sertraline malonate Form C can be characterized by any one, any two, any three, any four, any five, or any six or more of the peaks in the PXRD diffractogram in FIG. 13F including, but not limited to, 8.42, 10.51, 12.45, 14.27, 16.89, 17.23, 20.57, 21.34, 22.68, 23.67, and 25.09 degrees 2-theta.

TABLE III

PXRD Data for Sertraline Malonate Forms B and C

Figure 13D:
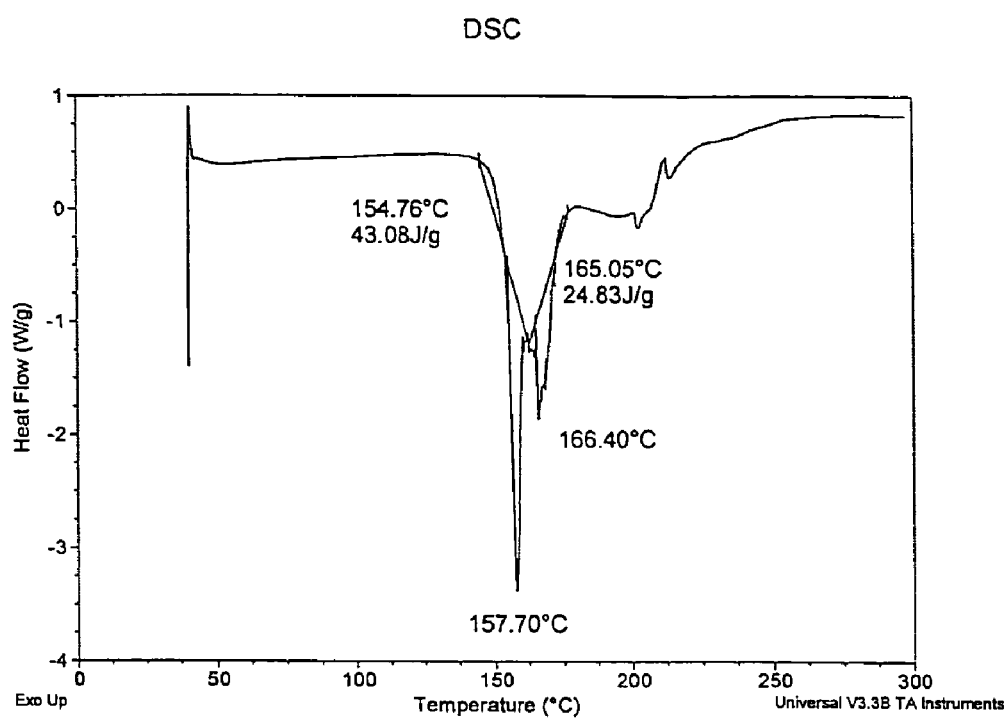
Figure 13E:
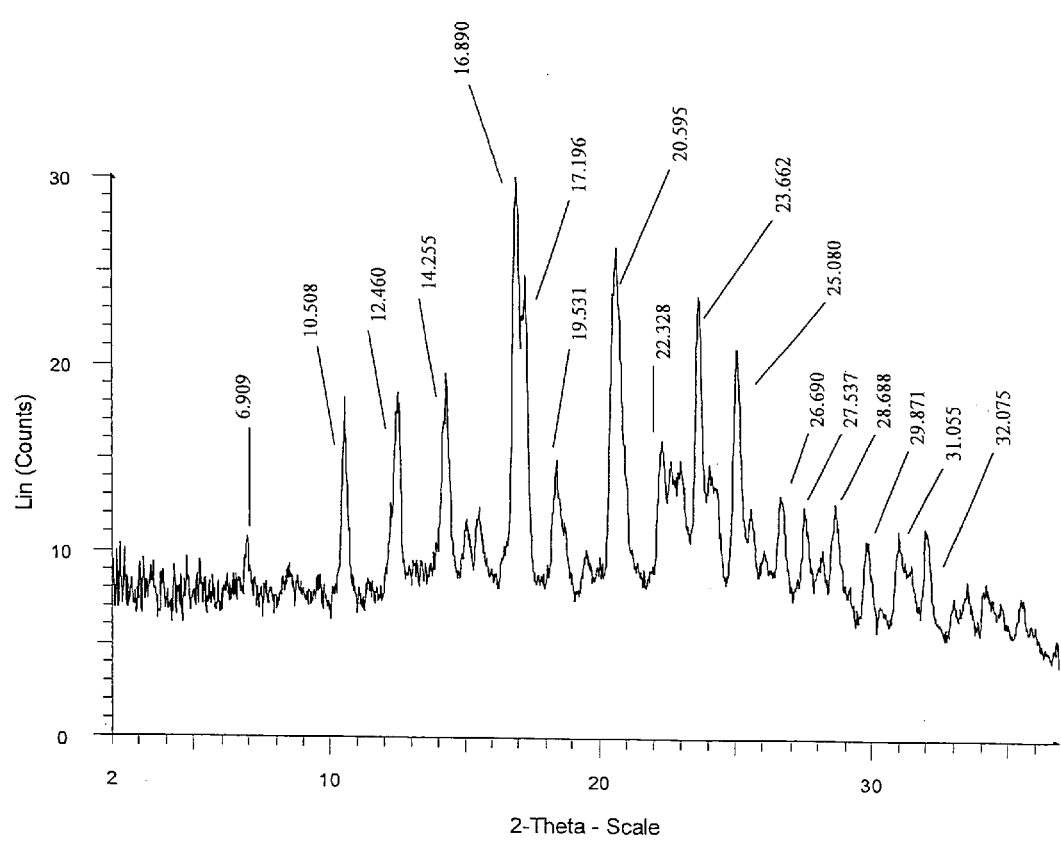
Figure 13F:
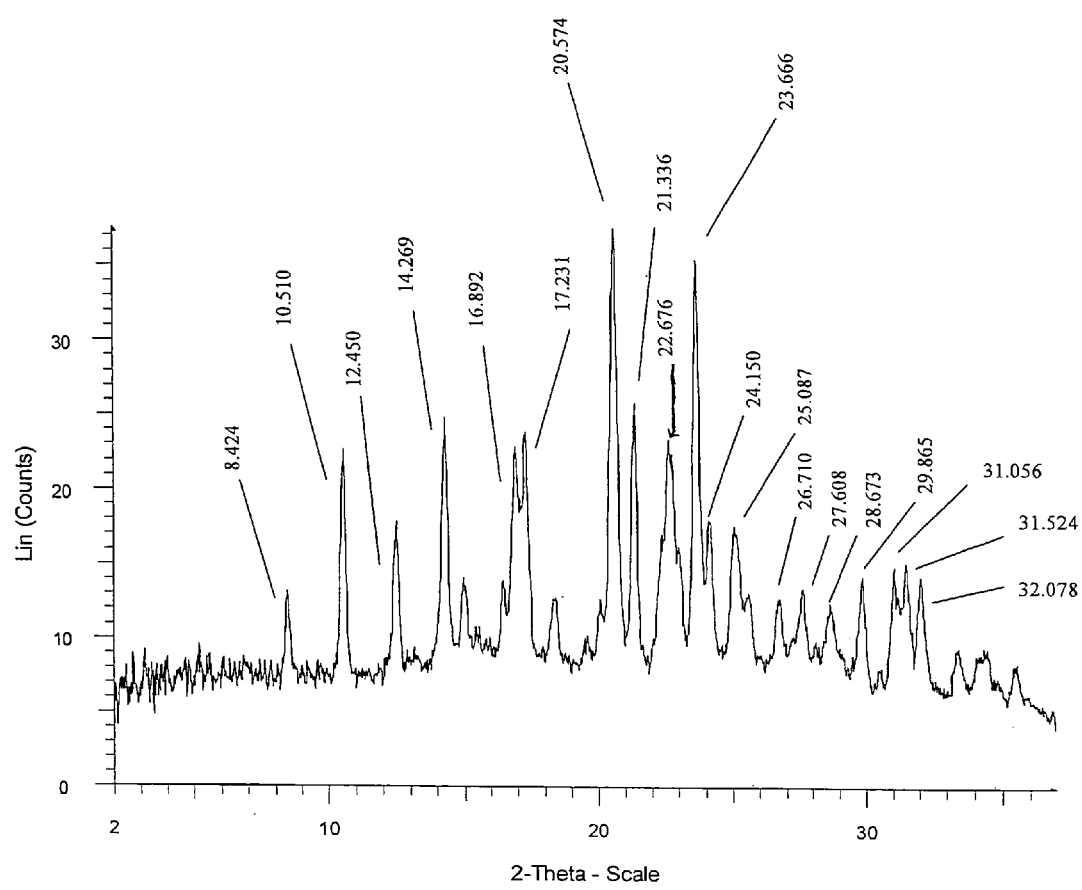

| FIG. 13E | | FIG. 13F | |
|---|---|---|---|
| Angle 2-theta degrees | Intensity percent | Angle 2-theta degrees | Intensity percent |
| 6.909 | 17.3 | 8.424 | 35.0 |
| 10.508 | 49.9 | 10.510 | 60.3 |
| 12.460 | 50.6 | 12.450 | 47.5 |
| 14.255 | 54.6 | 14.269 | 65.9 |
| 15.038 | 19.9 | 14.963 | 37.3 |
| 15.492 | 22.6 | 16.442 | 37.0 |
| 16.890 | 100.0 | 16.892 | 59.8 |
| 17.196 | 76.6 | 17.231 | 63.5 |
| 18.384 | 32.6 | 18.344 | 33.5 |
| 19.531 | 10.7 | 20.083 | 34.3 |
| 20.595 | 81.0 | 20.574 | 100.0 |
| 22.328 | 33.3 | 21.336 | 68.6 |
| 23.662 | 67.4 | 22.340 | 44.6 |
| 24.290 | 22.2 | 22.676 | 62.4 |
| 25.080 | 56.3 | 23.005 | 43.1 |
| 25.600 | 20.6 | 23.666 | 94.6 |
| 26.690 | 26.0 | 24.150 | 47.8 |
| 27.537 | 23.3 | 25.087 | 46.7 |
| 28.688 | 28.1 | 25.564 | 34.7 |
| 29.871 | 19.7 | 26.710 | 33.7 |
| 31.055 | 24.9 | 27.608 | 35.6 |
| 32.075 | 26.2 | 28.673 | 33.0 |
| 35.569 | 14.4 | 29.865 | 37.7 |
| 22.694 | 28.9 | 31.056 | 39.4 |
| 23.000 | 29.2 | 31.524 | 40.1 |
| 26.111 | 12.0 | 32.078 | 37.7 |
| 28.194 | 16.1 | 33.427 | 24.6 |
| 33.528 | 15.5 | 35.522 | 21.4 |

DSC analyses were completed on two different samples of Form A sertraline malonate. The first sample was prepared from isopropyl acetate:acetonitrile and yielded two endothermic transitions, one at about 165 degrees C. and another at about 182 degrees C. (See FIG. 13B). The PXRD for this sample is shown in FIG. 13A. The second sample was prepared from acetonitrile and yielded two endothermic transitions, one at about 158 degrees C., and another at about 166 degrees C. (See FIG. 13D). The PXRD for this sample is shown in FIG. 13C.

Sertraline malonate form A was crystallized from 2-propanol:n-heptane, 2-propanol:isopropyl acetate, propylene glycol:water, isopropyl acetate:acetonitrile, isopropyl acetate, acetonitrile, ethanol:isopropyl acetate, and n-heptane:2-propanol. Sertraline malonate forms B and C were crystallized from ethanol.

Sertraline L-tartrate Salt

Two polymorphs of sertraline L-tartrate salt have been discovered. Forms A and B each yield distinctive PXRD diffractograms. Form A can be characterized by PXRD peaks at 13.61, 14.93, 18.37, 20.47, 22.03, 22.89, and 24.39 degrees 2-theta. Form B can be characterized by PXRD peaks at 11.47, 12.41, 14.39, 16.21, 18.57, 21.51, 22.79, and 26.37 degrees 2-theta.

Figure 14A:
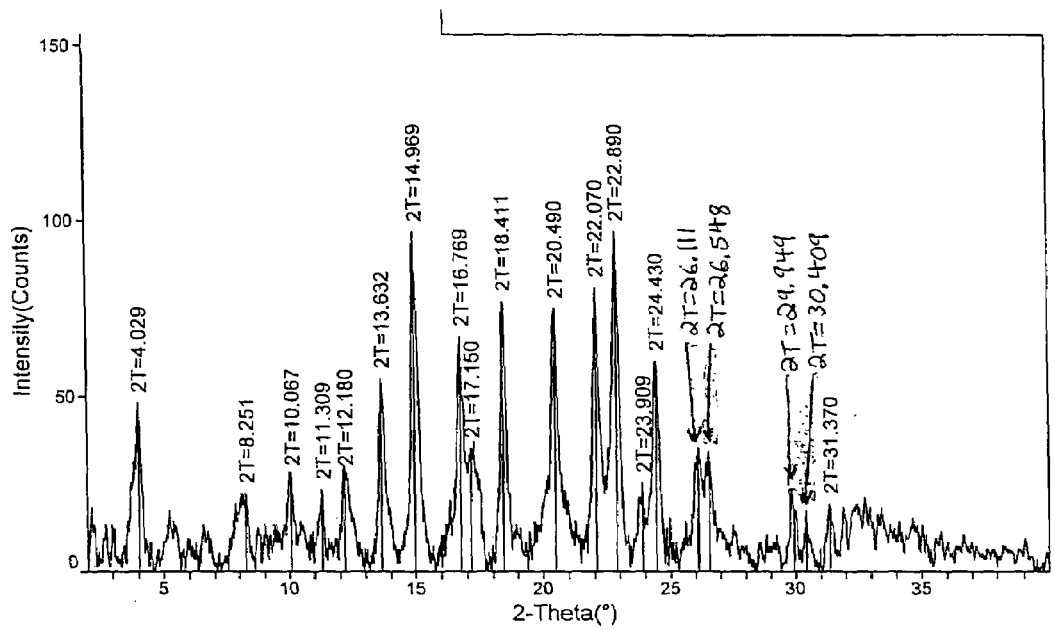
Figure 14B:
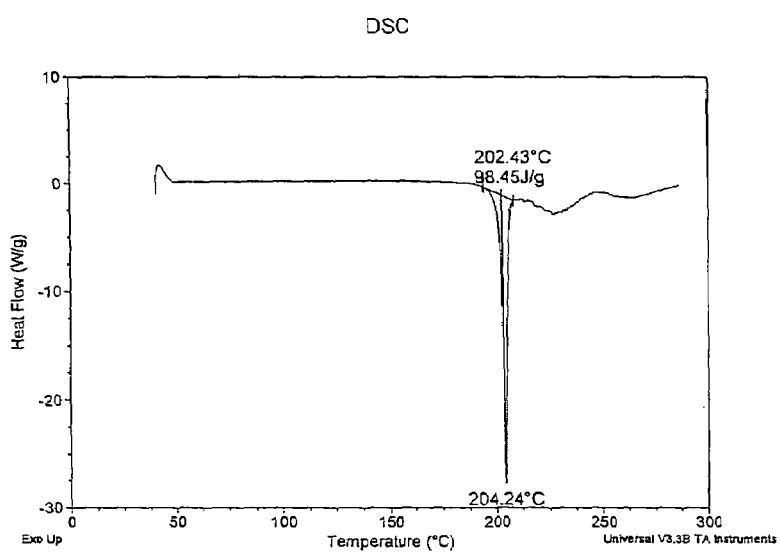
Figure 14C:
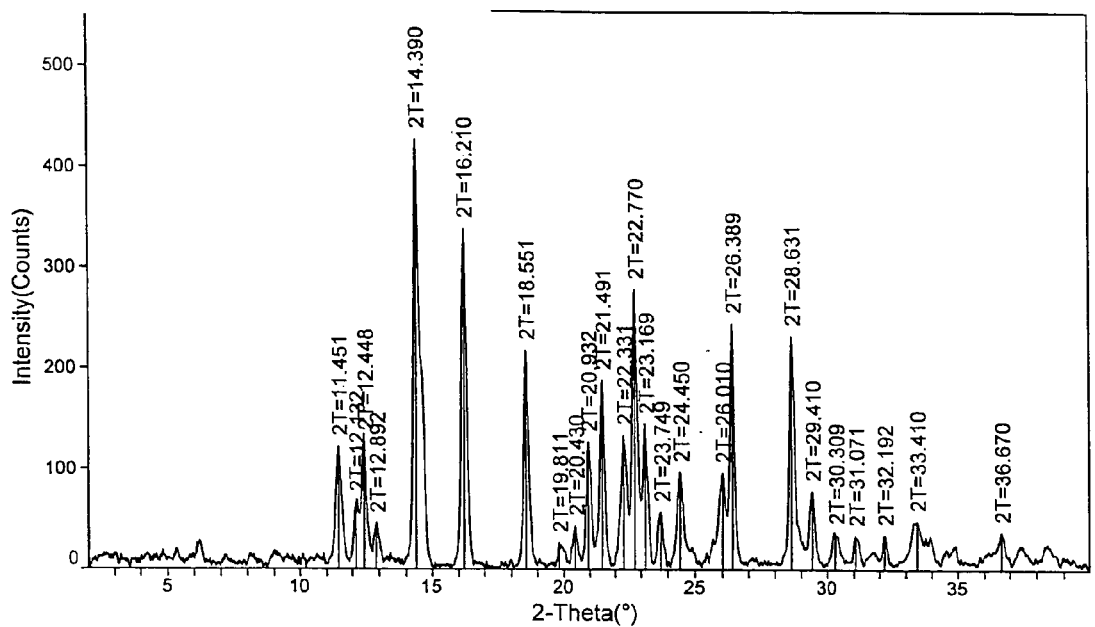

Sertraline L-tartrate Form A can be characterized by any one, any two, any three, any four, any five, or any six or more of the peaks in the PXRD diffractogram in FIG. 14A including, but not limited to, 4.03, 10.07, 11.31, 12.18, 13.63, 14.97, 16.77, 18.41, 20.49, 22.07, 22.89, 24.43, and 26.11 degrees 2-theta. Sertraline L-tartrate Form B can be characterized by any one, any two, any three, any four, any five, or any six or more of the peaks in the PXRD diffractogram in FIG. 14C including, but not limited to, 11.45, 12.45, 14.39, 16.21, 18.55, 20.93, 21.49, 22.77, 24.45, 26.39, and 28.63 degrees 2-theta.

Figure 14D:
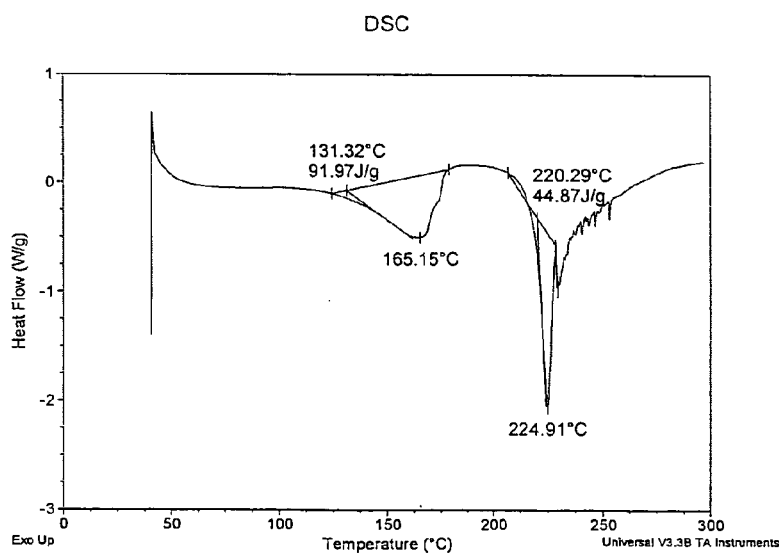

DSC analyses was completed on Forms A and B of sertraline L-tartrate salt. Form A showed an endothermic transition at about 204 degrees C. (See FIG. 14B). Form B showed two endothermic transitions, one at about 165 degrees C. and another at about 225 degrees C. (See FIG. 14D).

Sertraline L-tartrate form A was crystallized from water, ethanol, 2-propanol, tetrahydrofuran, and ethanol:iso-butanol. Sertraline L-tartrate form B was crystallized from acetonitrile:isopropyl acetate, isobutanol:ethanol, ethanol, iso-butanol:isopropyl acetate, and acetonitrile:propylene glycol.

Sertraline Maleate Salt

Several polymorphs of sertraline maleate salt have been discovered. Forms A–D each yield distinctive PXRD diffractograms. Form A can be characterized by PXRD peaks at 3.71, 10.33, 14.93, 18.39, and 25.69 degrees 2-theta. Form B can be characterized by PXRD peaks at 10.85, 18.51, 20.25, and 21.85 degrees 2-theta. Form C can be characterized by PXRD peaks at 10.07, 16.04, 20.34, and 22.34 degrees 2-theta. Form D can be characterized by PXRD peaks at 11.18, 15.85, 21.13, 22.4, and 23.07 degrees 2-theta.

Figure 15A:
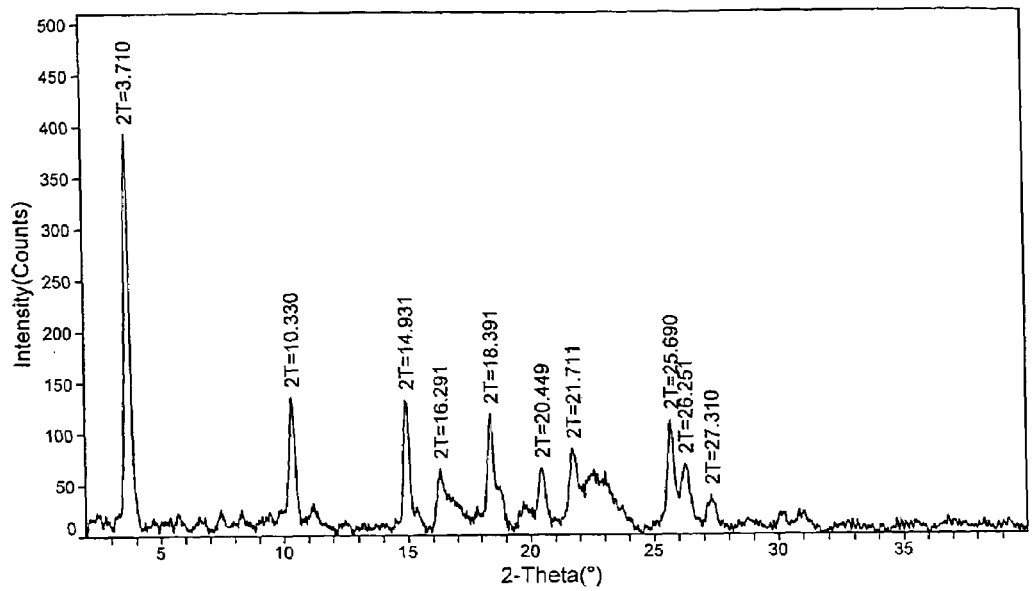
Figure 15B:
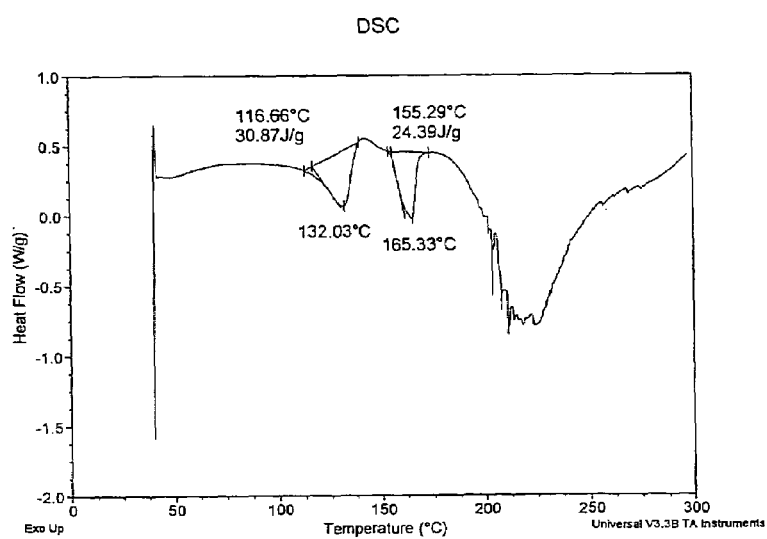
Figure 15C:
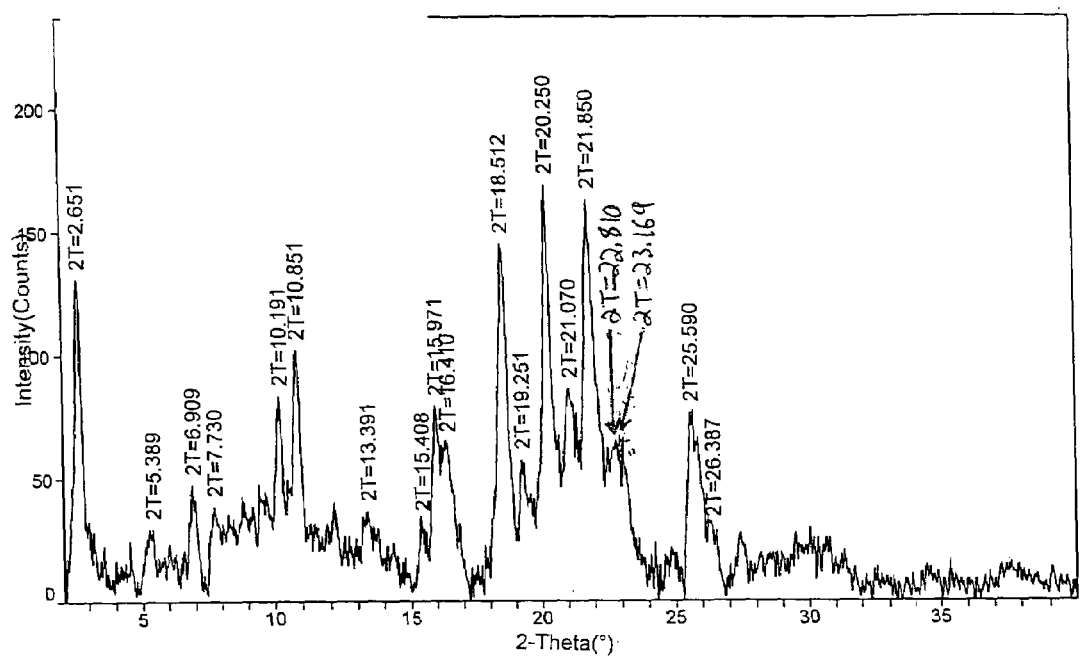

Sertraline maleate Form A can be characterized by any one, any two, any three, any four, any five, or any six or more of the peaks in the PXRD diffractogram in FIG. 15A including, but not limited to, 3.71, 10.33, 14.93, 16.29, 18.39, 20.45, 21.71, 25.69, and 26.25 degrees 2-theta. Sertraline maleate Form B can be characterized by any one, any two, any three, any four, any five, or any six or more of the peaks in the PXRD diffractogram in FIG. 15C including, but not limited to, 2.65, 10.19, 10.85, 15.97, 18.51, 20.25, 21.85, and 25.59 degrees 2-theta. Sertraline maleate Form C can be characterized by any one, any two, any three, any four, any five, or any six or more of the peaks in the PXRD diffractogram in FIG. 15D including, but not limited to, 10.07, 16.04, 20.34, 22.34, 23.40, 24.20, 25.19, 28.53, and 29.27 degrees 2-theta. Sertraline maleate Form D can be characterized by any one, any two, any three, any four, any five, or any six or more of the peaks in the PXRD diffractogram in FIG. 15E including, but not limited to, 5.57, 11.18, 15.23, 15.85, 17.19, 18.47, 21.13, 22.59, 25.22, 26.60, 27.50, and 30.23 degrees 2-theta.

TABLE IV

PXRD Data for Sertraline Maleate Forms C and D

Figure 15D:
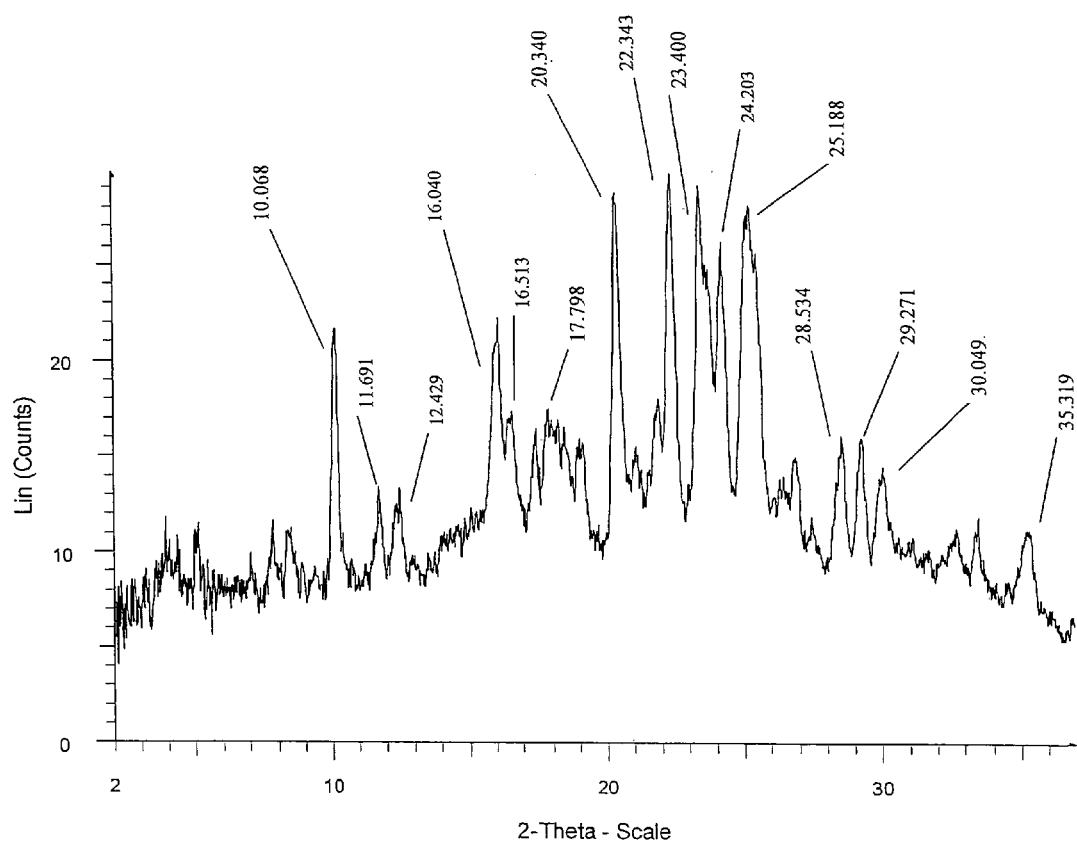
Figure 15E:
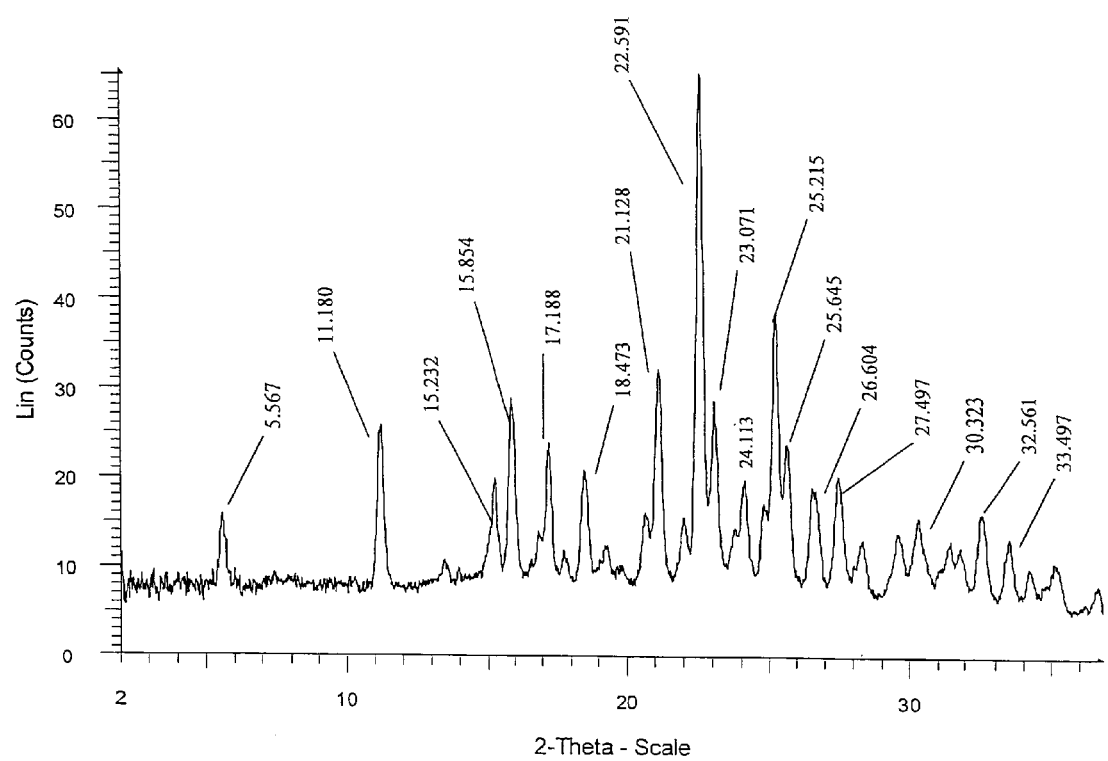

| FIG. 15D | | FIG. 15E | |
|---|---|---|---|
| Angle 2-theta degrees | Intensity percent | Angle 2-theta degrees | Intensity percent |
| 5.004 | 36.7 | 5.567 | 23.9 |
| 7.833 | 39.0 | 11.180 | 39.3 |
| 8.370 | 37.0 | 13.452 | 16.3 |
| 10.068 | 72.6 | 15.232 | 30.4 |
| 11.691 | 44.8 | 15.854 | 44.0 |
| 12.429 | 44.6 | 16.833 | 21.7 |
| 16.040 | 73.8 | 17.188 | 36.4 |
| 16.513 | 57.4 | 17.754 | 17.9 |
| 17.385 | 53.5 | 18.473 | 31.9 |
| 17.798 | 58.4 | 19.263 | 18.7 |
| 18.194 | 56.9 | 20.677 | 24.3 |
| 18.444 | 54.8 | 21.128 | 49.2 |
| 19.055 | 52.7 | 22.027 | 23.8 |
| 20.340 | 96.4 | 22.591 | 100.0 |
| 21.852 | 60.4 | 23.071 | 44.0 |
| 22.343 | 100.0 | 23.806 | 21.7 |
| 23.400 | 97.8 | 24.113 | 30.4 |
| 23.662 | 81.7 | 24.837 | 25.3 |
| 24.203 | 88.0 | 25.215 | 58.9 |
| 25.188 | 94.3 | 25.645 | 36.4 |
| 25.412 | 84.6 | 26.604 | 28.6 |
| 26.854 | 50.3 | 27.497 | 31.1 |
| 28.534 | 53.9 | 28.323 | 19.9 |
| 29.271 | 53.5 | 29.637 | 21.3 |
| 30.049 | 48.5 | 30.323 | 23.9 |
| 33.451 | 38.9 | 31.454 | 19.5 |
| 35.319 | 37.5 | 31.854 | 18.8 |
| | | 32.561 | 24.7 |
| | | 33.497 | 20.4 |
| | | 34.255 | 15.1 |
| | | 35.192 | 16.2 |
| | | 36.764 | 12.5 |

DSC analysis was completed on Form A of the sertraline maleate salt. Two endothermic transitions were shown, one at about 132 degrees C. and another at about 165 degrees C. (See FIG. 15B).

Sertraline maleate Form A was crystallized from 2-propanol:ethanol and 32:13 acetonitrile:2-propanol. Sertraline maleate Form B was crystallized from 2-propanol:tetrahydrofuran and ethanol. Sertraline maleate Forms C and D were crystallized from acetonitrile.

Sertraline HCl Acetic Acid Solvate 47.2 mg sertraline HCl was suspended in 1.0 mL glacial acetic acid. The suspension was gently warmed to 60 degrees C., causing the solid to completely dissolve. The solution was then allowed to cool to room temperature. After 16 hours, a white crystalline material formed. The solid was collected via filtration and allowed to air dry over night. Subsequent analysis showed the solid was a 1:1 acetic acid solvate of sertraline HCl.

Figure 16A:
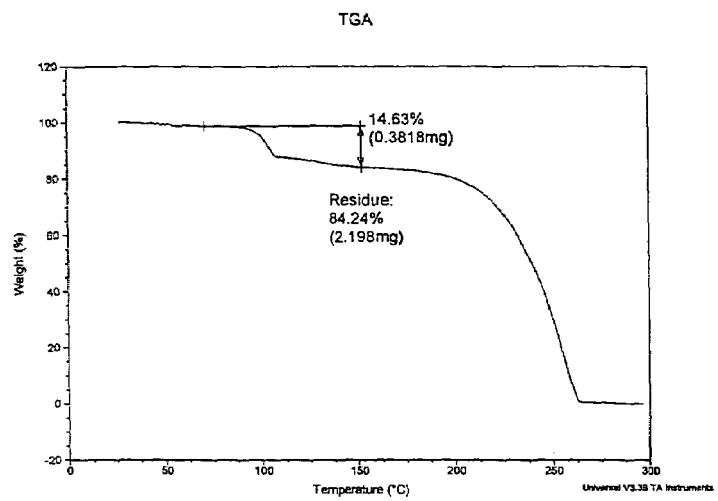

Thermogravimetric analysis (TGA) of sertraline HCl acetic acid solvate shows a significant loss of mass (about 14.6 percent) at about 85 degrees C. which is consistent with 1 molar equivalent of acetic acid as compared to sertraline HCl (FIG. 16A).

Figure 16B:
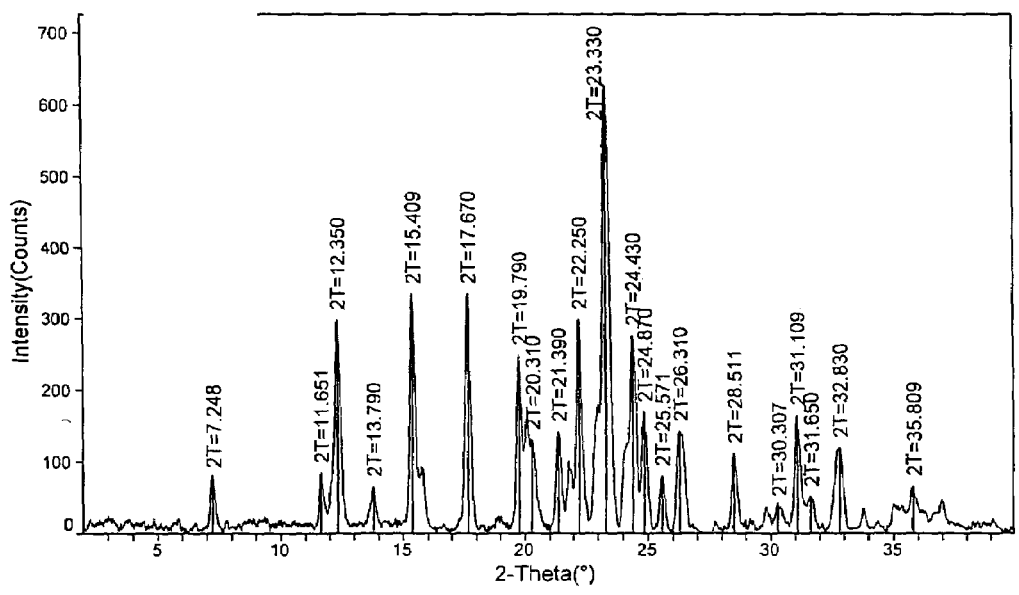

PXRD also shows the presence of acetic acid as compared to sertraline HCl (FIG. 16B). The diffractogram comprises peaks with 2-theta angles of 7.25, 12.35, 15.41, 17.67, 19.79, 22.25, 23.33, 24.43, 28.51, 31.11, and 32.83 degrees where any one or any combination of two, three, four, five, six, seven, eight, nine, or ten or more peaks of FIG. 16B can be used to characterize sertraline HCl acetic acid solvate.

Figure 16C:
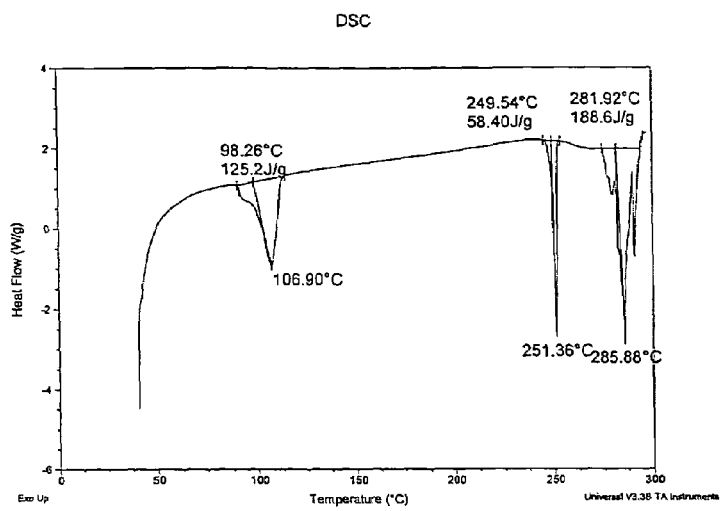
Figure 16D:
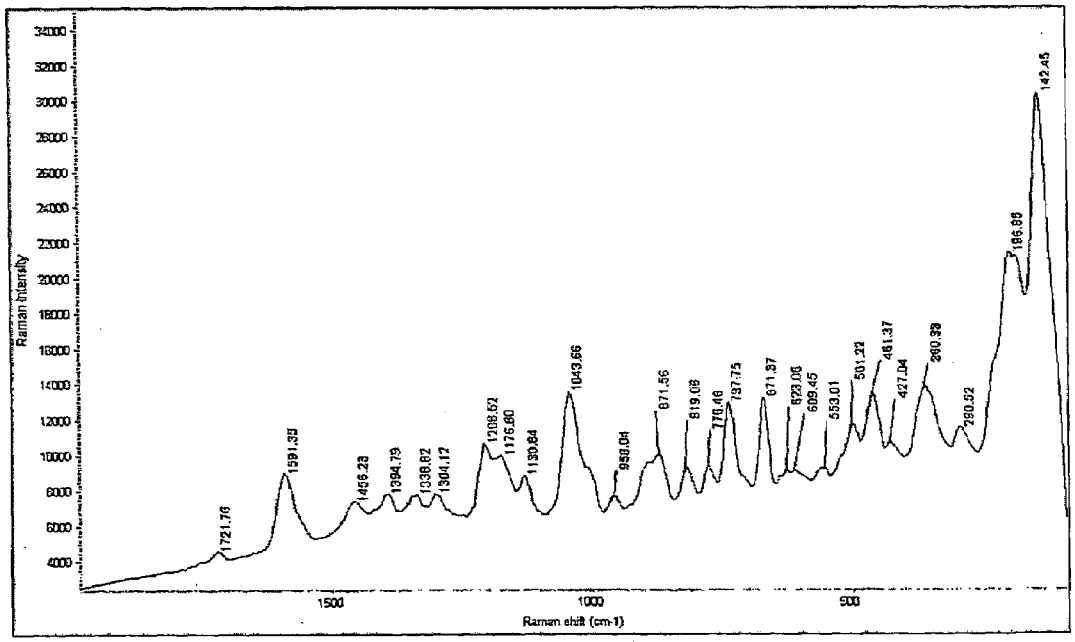

Differential scanning calorimetry (DSC) of sertraline HCl acetic acid solvate shows several endothermic transitions at about 107, 251, and 286 degrees C. (FIG. 16C). Raman spectroscopy was also used to analyze the solvate and several Raman shifts were detected. FIG. 6D illustrates the Raman spectrum of sertraline HCl acetic acid solvate comprising characteristic absorptions in $cm^{-1}$ at about 1591, 1209, 1044, 872, 738, 671, 461, and 360. Any one, or any combination of these absorptions or any others in the Raman spectrum can be used to characterize the sertraline HCl acetic acid solvate.

Sertraline HCl Ethyl Acetate Hemi-Solvate

Sertraline free base was dissolved in 0.5 mL toluene with 2 mL ethyl acetate added after dissolution. 10 microliters of concentrated HCl in 2 mL ethyl acetate was added dropwise over 15 minutes. A clear gel formed. A small amount of mandelic acid was added and the gel was vortexed and left to stir overnight. Over a period of 24 hours, the gel cleared and white crystalline solid formed. Subsequent analysis showed the solid was an ethyl acetate hemi-solvate of sertraline HCl.

Figure 17A:
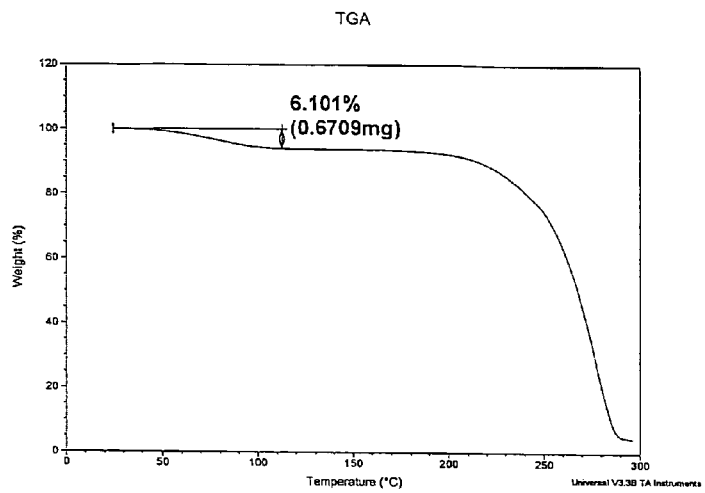
Figure 17B:
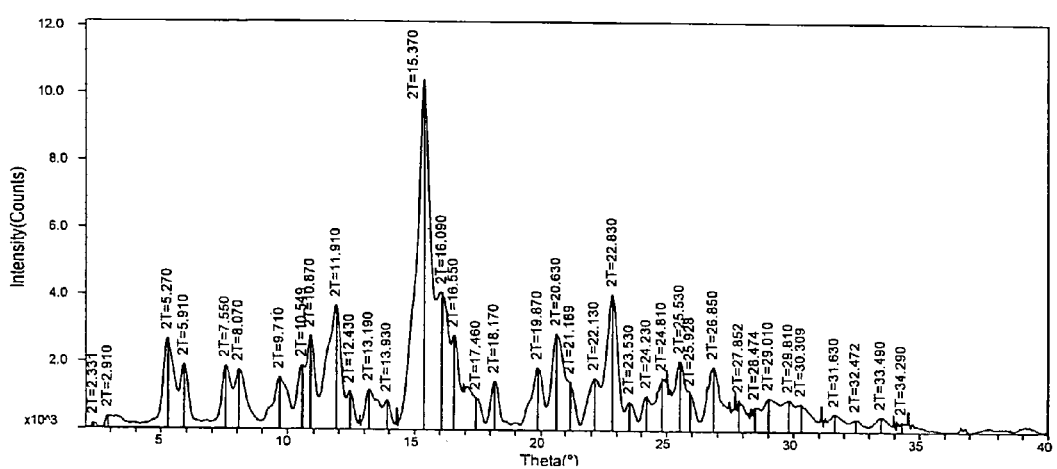

TGA of sertraline HCl ethyl acetate hemi-solvate shows a measurable loss of mass between about 50 and 100 degrees C. This is consistent with a hemi-solvate due to the loss of less than 1 equivalent of ethyl acetate (about 6.1 percent) as compared to sertraline HCl (FIG. 17A). Powder x-ray diffraction also shows clear distinction from that of sertraline HCl. The diffractogram of sertraline HCl ethyl acetate hemi-solvate changes as the sample dries. Under air-drying conditions, several days are needed to desolvate the sertraline HCl ethyl acetate hemi-solvate. FIG. 17B shows a diffractogram of sertraline HCl ethyl acetate hemi-solvate after air-drying for less than 30 minutes. FIG. 17B comprises peaks with 2-theta angles of 5.27, 5.91, 7.55, 8.07, 10.87, 11.91, 15.37, 16.03, 20.63, and 22.83 degrees where any one or any combination of two, three, four, five, six, seven, eight, nine, or ten or more peaks of the figure can be used to characterize sertraline HCl ethyl acetate hemi-solvate.

Figure 17C:
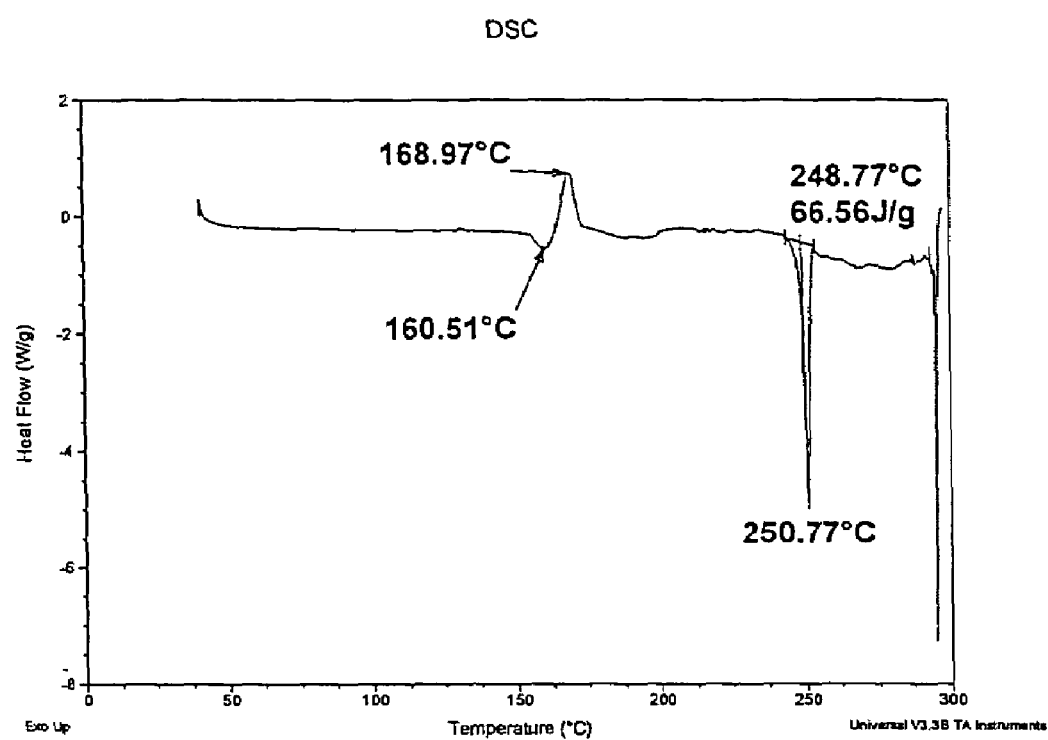

Differential scanning calorimetry (DSC) of the material shows an exothermic transition at about 251 degrees C. (FIG. 17C).

What is claimed is:

1. Sertraline hydrobromide.

2. The sertraline hydrobromide of claim 1, wherein said sertraline hydrobromide is characterized by a powder x-ray diffraction pattern comprising peaks at 7.0, 17.9, and 21.7 degrees 2-theta.

3. The sertraline hydrobromide of claim 1, wherein said sertraline hydrobromide is characterized by a powder x-ray diffraction pattern comprising peaks at 16.1, 21.2, and 24.0 degrees 2-theta.

4. The sertraline hydrobromide of claim 1, wherein said sertraline hydrobromide is characterized by a powder x-ray diffraction pattern comprising peaks at 7.0, 17.9, and 35.2 degrees 2-theta.

5. The sertraline hydrobromide of claim 1, wherein said sertraline hydrobromide is characterized by a powder x-ray diffraction pattern comprising peaks at 7.0, 16.1, 17.9. 21.2, and 24.0.

6. The sertraline hydrobromide of claim 1, wherein said sertraline hydrobromide is characterized by an endothermic transition at 266 degrees C.

7. A pharmaceutical composition comprising the sertraline hydrobromide of claim 1.

* * * * *